US007381479B2

(12) United States Patent
Lamansky et al.

(10) Patent No.: US 7,381,479 B2
(45) Date of Patent: *Jun. 3, 2008

(54) ORGANOMETALLIC COMPOUNDS AND EMISSION-SHIFTING ORGANIC ELECTROPHOSPHORESCENCE

(75) Inventors: Sergey Lamansky, Maplewood, MN (US); Mark E. Thompson, Anaheim, CA (US); Vadim Adamovich, Los Angeles, CA (US); Peter I. Djurovich, Long Beach, CA (US); Chihaya Adachi, Hokkaido (JP); Marc A. Baldo, Princeton, NJ (US); Stephen R. Forrest, Princeton, NJ (US); Raymond Kwong, Plainsboro, NJ (US)

(73) Assignees: The University of Southern California, Los Angeles, CA (US); The Trustees of Princeton University, Princeton, NJ (US); Universal Display Corporation, Ewing, NJ (US)

( * ) Notice: Subject to any disclaimer, the term of this patent is extended or adjusted under 35 U.S.C. 154(b) by 91 days.

This patent is subject to a terminal disclaimer.

(21) Appl. No.: 11/122,160

(22) Filed: May 3, 2005

(65) Prior Publication Data
US 2005/0214576 A1    Sep. 29, 2005

Related U.S. Application Data

(63) Continuation of application No. 09/978,455, filed on Oct. 16, 2001, now Pat. No. 6,939,624, which is a continuation-in-part of application No. 09/637,766, filed on Aug. 11, 2000, now Pat. No. 6,911,271.

(60) Provisional application No. 60/283,814, filed on Apr. 13, 2001.

(51) Int. Cl.
*H01L 51/54* (2006.01)
*C09K 11/06* (2006.01)
(52) U.S. Cl. .............. 428/690; 428/917; 313/504; 257/40; 257/E51.044; 546/2; 546/4; 546/5; 548/101; 548/103; 548/110; 548/402; 544/225
(58) Field of Classification Search ................ None
See application file for complete search history.

(56) References Cited

U.S. PATENT DOCUMENTS

| | | | |
|---|---|---|---|
| 6,656,608 B1 | 12/2003 | Kita et al. | 428/690 |
| 6,670,645 B2 | 12/2003 | Grushin et al. | 257/98 |
| 6,867,538 B2* | 3/2005 | Adachi et al. | 313/503 |
| 6,936,716 B1* | 8/2005 | Lin | 546/2 |
| 6,939,624 B2* | 9/2005 | Lamansky et al. | 428/690 |
| 2001/0019782 A1 | 9/2001 | Igarashi et al. | 428/690 |
| 2002/0024293 A1 | 2/2002 | Igarashi et al. | 313/483 |
| 2002/0034656 A1 | 3/2002 | Thompson et al. | 428/690 |
| 2002/0121638 A1 | 9/2002 | Grushin et al. | 257/40 |
| 2002/0190250 A1 | 12/2002 | Grushin et al. | 257/40 |

OTHER PUBLICATIONS

U.S. Appl. No. 60/273,284, filed Mar. 2001.*
M. A. Baldo, et al., "Highly efficient phosphorescent emission from organic electroluminescent devices," Nature, Sep. 1998, vol. 395, pp. 151-154.
M.A. Baldo, et al., "Very high-efficiency green organic light-emitting devices based on electrophosphorescence", Applied Physics Letters, vol. 75, No. 1, pp. 4-6, Jul. 5, 1999.
C. Adachi, et al., "High-efficiency organic electrophosphorescent devices with tris(2-phenylpyridine) iridium doped into electron-transporting materials", App. Phys. Lett., vol. 77, No. 6, pp. 904-906, (Aug. 7, 2000).
C. Adachi, et al. "High-efficiency red electrophosphorescence devices", App. Phys. Lett., vol. 78, No. 11, pp. 1622-1624 (Mar. 12, 2001).
C. Adachi, et al., "High efficiency organic light emitting diodes using electrophosphorescene", Am. Phys. Soc., Series II, vol. 46, No. I, Part II, p. 863 (Mar. 2001).
M.A. Baldo, et al., "Excitonic singlet-triplet ratio in a semiconducting organic thin film", Phys. Rev., B vol. 60, No. 20, pp. 14422-14428 (Nov. 15, 1999).
R.H. Friend, et al., "Electroluminescence in conjugated polymers", Nature (London), vol. 397, pp. 121-128 (Jan. 14, 1999).
Y. Cao, et al., "Improved quantum efficiency for electroluminescence in semiconducting polymers", Nature (London), vol. 397, pp. 414-417 (Feb. 4, 1999).
M.A. Baldo, et al., "Transient analysis of organic electrophosphorescence: I. Transient analysis of triplet energy transfer", Phys. Rev. B vol. 62, No. 16, pp. 10958-10966 (Oct. 15, 2000).
W.E. Ford, et al., "Reversible triplet-triplet energy transfer within a covalently linked bichromophoric molecule", J. Phys. Chem., 96, pp. 2917-2920 (1992).
A. Harriman, et al., "A ruthenium (II) tris(2,2'-bipyridine) derivative possessing a triplet lifetime of 42us" R. Chem. Commun., pp. 735-736 (1999).
Gary L. Miessler, et al., Inorganic Chemistry, 2nd Edition, Prentice-Hall (1998), pp. 1-3, 422-424.
O. Lohse, et al., "The Palladium Catalysed suzuki coupling of 2- and 4-chloropyridines", Synlett, 1999, No. 1, pp. 45-48.
Q.G. Wu, et al., "Blue-luminescent/electroluminescent Zn(II) compounds of 7-azaindole and N-(2-Pyridyl)-7-azaindole:", Inorg. Chem., 39, pp. 5248-5254 (2000).

(Continued)

*Primary Examiner*—Marie Yamnitzky
(74) *Attorney, Agent, or Firm*—Kenyon & Kenyon LLP

(57) ABSTRACT

Emissive phosphorescent organometallic compounds are described that produce improved electroluminescence, particularly in the blue region of the visible spectrum. Organic light emitting devices employing such emissive phosphorescent organometallic compounds are also described. Also described is an organic light emitting layer including a host material having a lowest triplet excited state having a decay rate of less than about 1 per second; a guest material dispersed in the host material, the guest material having a lowest triplet excited state having a radiative decay rate of greater than about $1 \times 10^5$ or about $1 \times 10^6$ per second and wherein the energy level of the lowest triplet excited state of the host material is lower than the energy level of the lowest triplet excited state of the guest material.

9 Claims, 49 Drawing Sheets

OTHER PUBLICATIONS

Y. Ma, et al., "A ligand-stabilized tetrameric zinc (II) cluster with high-efficiency emission from both singlet and triplet excited slates for electroluminescent devices", Adv. Mat., 12, No. 6, pp. 433-435 (2000).

A.W. Grice, et al., "High brightness and efficiency blue light-emitting polymer diodes", Appl. Phys. Lett., vol. 73, No. 5, pp. 629-931 (Aug. 3, 1998).

Hosokawa et al., "Highly efficient blue electroluminescence from a distyrylarylene emitting layer with a new dopant," 67 Appl. Phys. Lett, 3853-3855 (Dec. 1995).

C. Hosokawa, et al., "Organic multi-color electroluminescence display with fine pixels", Synth. Met., 91, pp. 3-7 (1997).

K.A. King, et al., "Excited State properties of a triply ortho-metalated Iridium (III) complex", J. Am. Chem. Soc., 107, pp. 1431-1432 (1985).

S. Lamansky, et al., "Synthesis and characterization of phosphorescent cyclometalated iridium complexes" Inorganic Chemistry, 40, pp. 1704-1711 (2001).

C. Adachi, et al., "Electroluminescence mechanisms in organic light emitting devices employing a europium chelate doped in a wide energy gap bipolar conducting host", J. Appl. Phys., vol. 87, No. 11, pp. 8049-8055, Jun. 1, 2000.

M.A. Baldo, et al., "Transient analysis of organic electrophosphorescence: I. Transient analysis of triplet-triplet annihilation" Phys. Rev. B vol. 62, No. 16, pp. 10967-10977 (Oct. 15, 2000).

C. Adachi, et al., "Efficient electrophosphorescence using a doped ambipolar conductive molecular organic thin film", Organic Electronics, 2, pp. 37-43 (2001).

G.W.V. Cave et al., "C-H Activation Induced by Water. Monocyclometalated to Dicyclometalated: CNC Tridentate Platinum Complexes", Organometallics 2000, vol. 19, No. 7, pp. 1355-1364.

D.F. O'Brien, et al., "Improved energy transfer in electrophosphorescent devices", Applied Physics Letters, vol. 74, No. 3, pp. 442-444, (Jan. 18, 1999).

T. Tsutsui et al., "High quantum efficiency in organic light-emitting devices with iridium-complex as a triplet emissive center", Japanese. J. Appl. Phys., Part 2, No. 12B, vol. 38, pp. L1502-1504 (Dec. 15, 1999).

M. J. Yang et al., "Use of Poly(9-vinylcarbazole) as host material for Iridium complexes in high-efficiency organic light emitting devices", Japanese J. Appl. Phys., Part 2, No. 8A, vol. 39, pp. L828-829 (Aug. 1, 2000).

C. L. Lee et al., "Polymer phosphorescent light-emitting devices doped with tris(2-phenylpyridine) Iridium as a triplet emitter", Appl. Phys. Lett., vol. 77, No. 15, pp. 2280-2282 (Oct. 9, 2000).

Shirota et al., "Multilayered organic electroluminescent device using a novel starburst molecule, 4, 4', 4"-tris(3-methylphenylphenylamino) triphenylamine, as a hole transport material", Appl. Phys. Lett., vol. 65, No. 7, pp. 807-809 (Aug. 15, 1994).

M. A. Baldo, et al., "High-efficiency fluorescent organic light-emitting devices using a phosphorescent sensitizer", Nature, vol. 403, pp. 750-753, Feb. 17, 2000.

Von Zelewsky, et al., "Tailor Made Coordination Compounds for Photochemical purposes", Coordination Chemistry Reviews, 132 (1994) pp. 75-85.

Y. Kunugi, et al., "A Vapochromic LED", J. Am. Chem. Soc., vol. 120, No. 3, pp. 589-590, 1998.

S. Lamansky, et al., "Highly Phosphorescent Bis-Cyclometalated Iridium Complexes: Synthesis, Photophysical Characterization, and Use in Organic Light Emitting Diodes", Journal of the American Chemical Society, vol. 123, No. 18, pp. 4304-4312, 2001.

M. Maestri, et al., "Photochemistry and Luminescence of Cyclometallated Complexes", Advances in Photochemistry, vol. 17, pp. 1-68, 1992.

B.N. Cockburn, et al., "Reactivity of Co-ordinated Ligands. Part XV. Formation of Complexes containing Grouop V Donor Atoms and Metal-Carbon $\infty$-bonds", Journal of the Chemical Society, Dalton Transactions, vol. 4 (1973), pp. 404-410.

Lamansky et al., Optical Properties of Pt (II) Cyclometalated Complexes in Polymer Matrices, Preparation and Potential Uses in OLEDs, Abstracts of Papers, Part 1, 217th ACS National Meeting, Anaheim, CA (Mar. 21-25, 1999).

Chemistry.ORG, The Website of the American Chemical Society, Internet Schedule of 217th ACS National Meeting, (Mar. 21-25, 1999); printed on Jul. 22, 2003 at <http://chemistry.org/portal/PersonalScheduler/SearchResults.isp?refineMode=Y&advSearch=0>.

Y. Ma, et al., "Electroluminescence from triplet metal-ligand charge-transfer excited state of transition metal complexes", Synthetic Metals 94 (1998), pp. 245-248.

H.F. Wittmann, et al., "Optical spectroscopy of platinum and palladium containing poly-ynes", J. Chem. Phys., vol. 101, No. 4, pp. 2693-2698, Aug. 15, 1994.

M.A. Baldo, et al., "Phosphorescent materials for application to organic light emitting devices", Pure Appl. Chem., vol. 71, No. 11, pp. 2095-2106, 1999.

G. DiMarco, et al., "A Luminescent Iridium(III) Cyclometallated Complex Immobilized in a Polymeric Matrix as a Solid-State Oxygen Sensor", Advanced Materials, vol. 8, pp. 576-580, Jul. 1996.

J.N. Demas, et al., "Design and Applications of Highly Luminescent Transition Metal complexes", Analytical Chemistry, vol. 63, No. 17, pp. 829-837, Sep. 1, 1991.

K. Vinodgopal, et al., "Photochemistry of Ru(bpy)2(dcbpy)2+ on Al2O3 and TiO2 Surfaces. An Insight into the Mechanism of Photosensitization", J. Phys. Chem. 1995, 99, pp. 10883-10889.

R. Holmlin et al., "Os(phen)2dppz2+ in Photoinduced DNA-Mediated Electron Transfer Reactions", J. Am. Chem. Soc. 1996, 118, pp. 5236-5244.

* cited by examiner

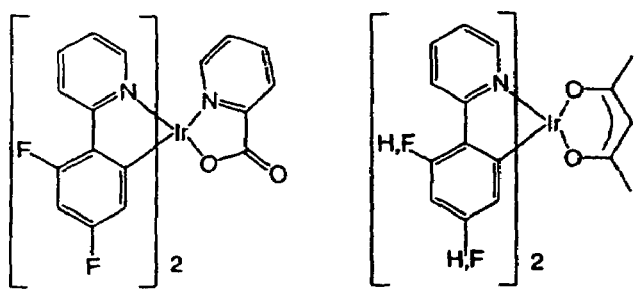
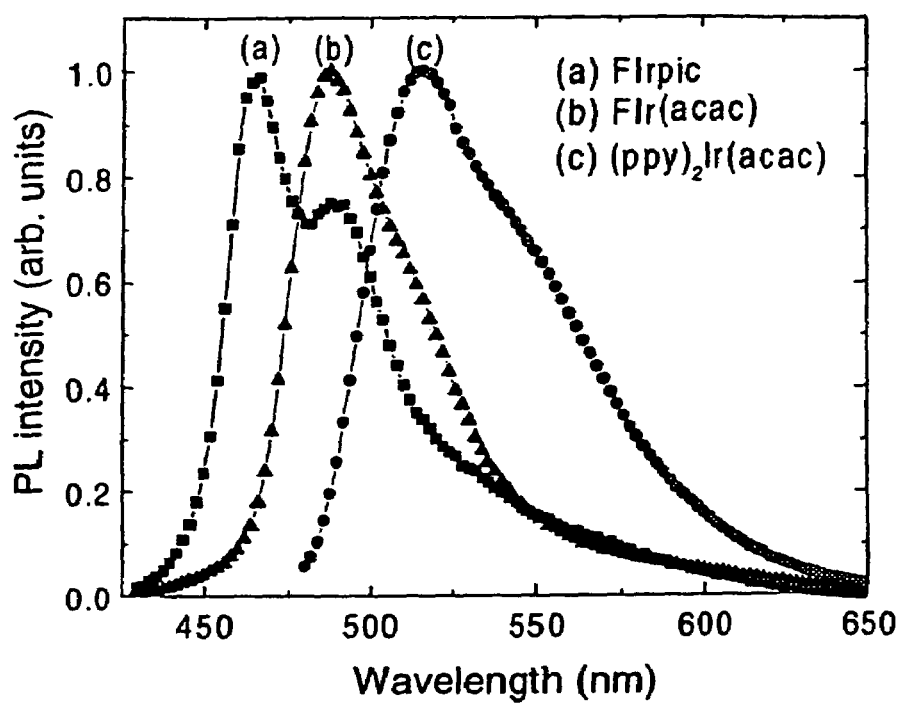
Figure 1a: C. Adachi, et. al.

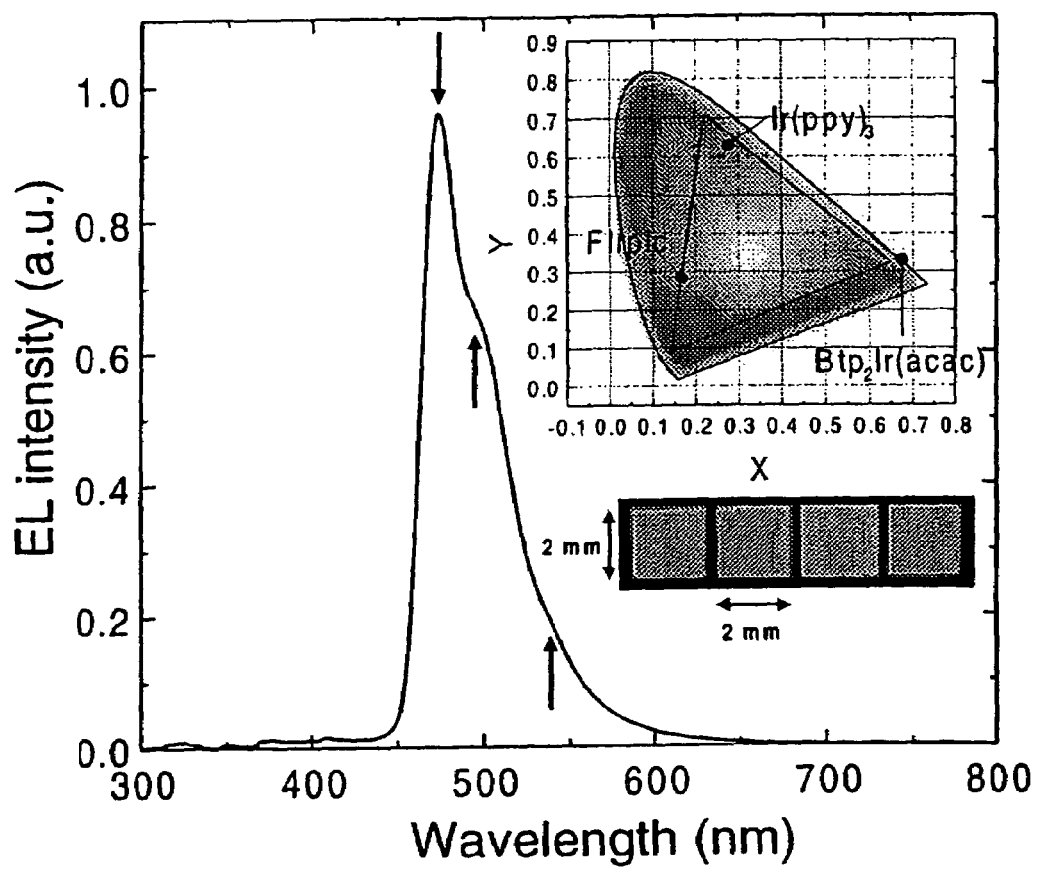
Figure 1b: C. Adachi, et. al.

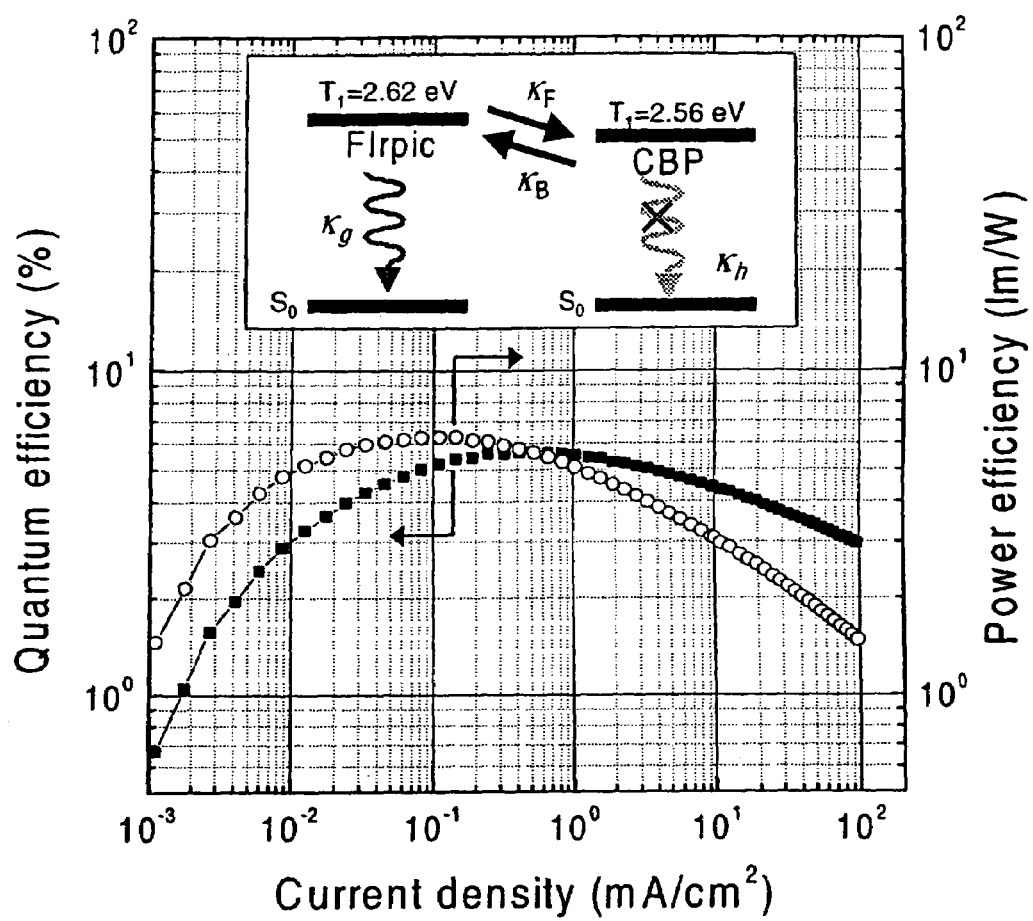
Figure 2: C. Adachi, et.al.

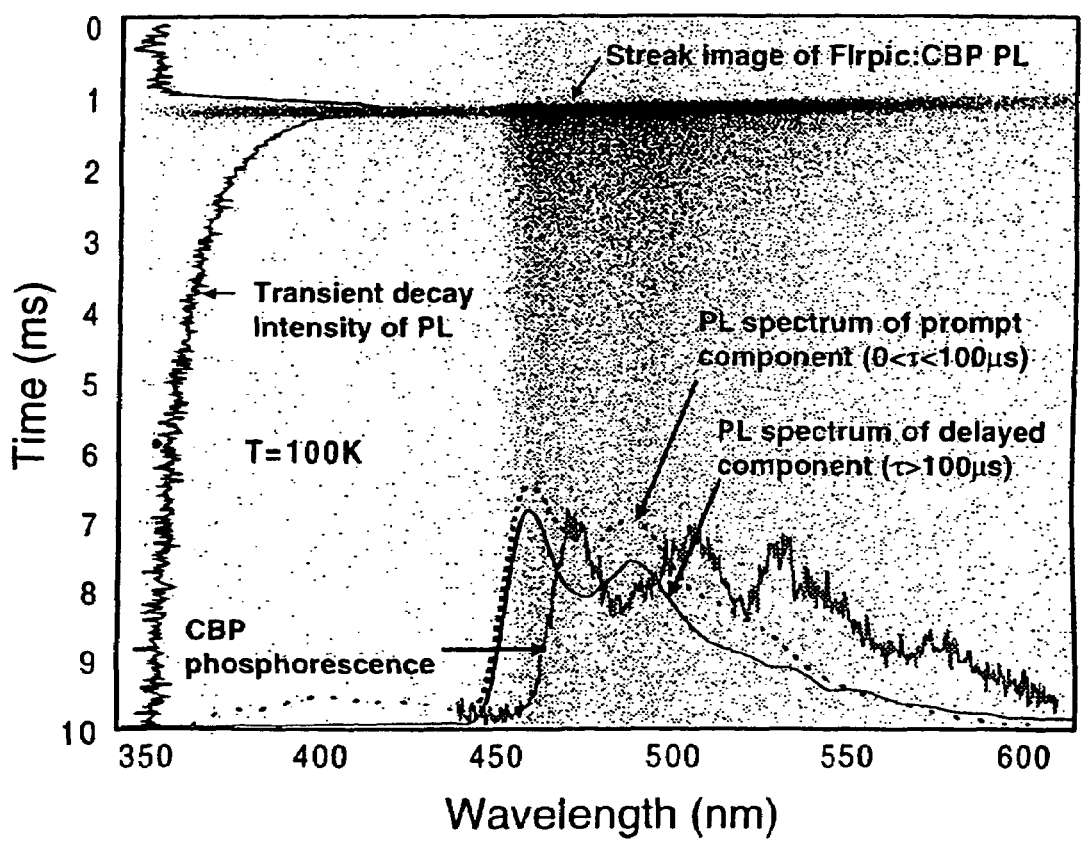
Figure 3: C. Adachi, et. al.

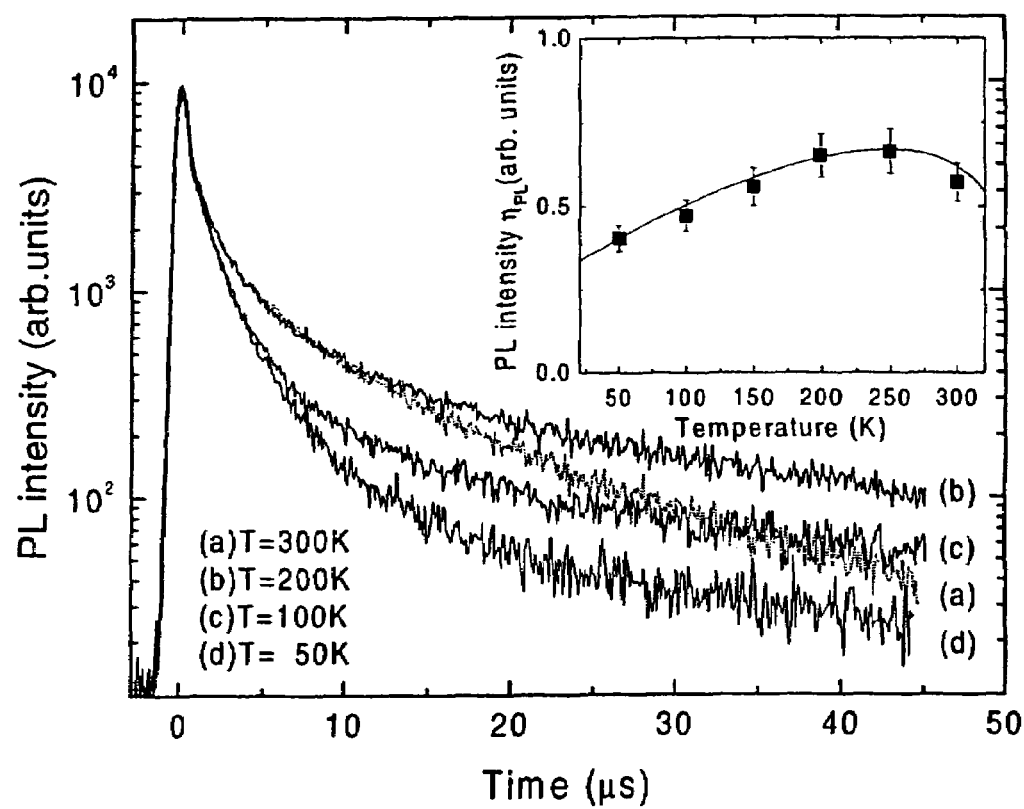
Figure 4: C. Adachi, et.al.

Generic Mono-Anionic, Bidentate, Carbon-Coordination Ligands-I
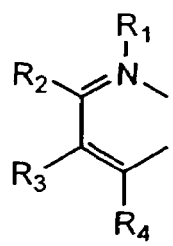
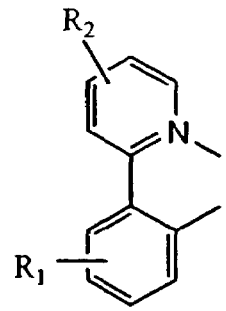
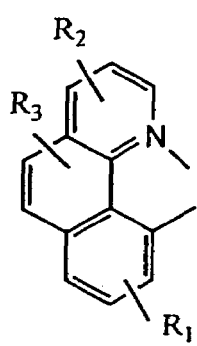
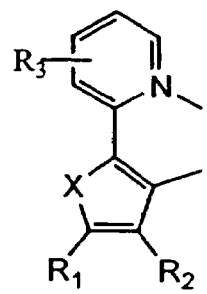
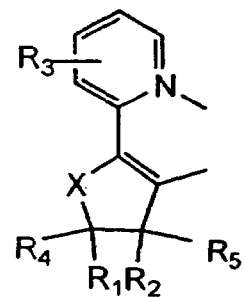
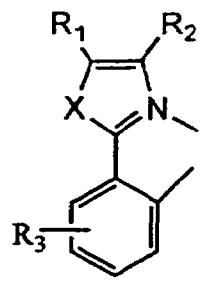
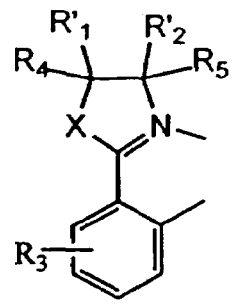
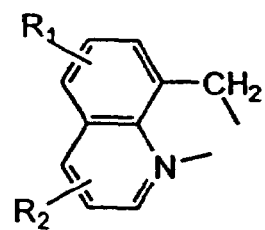
UDC Proprietary and Confidential
Figure 5a Generic Mono-Anionic, Bidentate, Carbon-Coordination Ligands-II Generic Mono-Anionic, Bidentate, Carbon-Coordination Ligands-III Specific Mono-Anionic, Bidentate, Carbon-Coordination Ligands-I UDC Proprietary and Confidential Generic Non-Mono-Anionic, Bidentate, Carbon-Coordination Ligands-I Generic Non-Mono-Anionic, Bidentate, Carbon-Coordination Ligands-II Specific Non-Mono-Anionic, Bidentate, Carbon-Coordination Ligands UDC Proprietary and Confidential

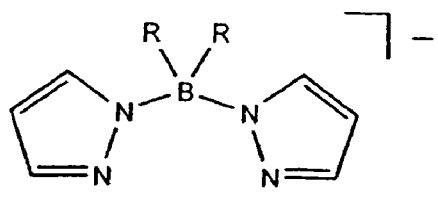
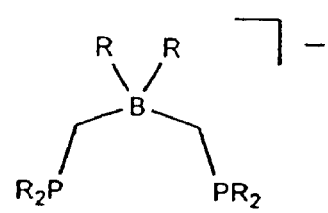
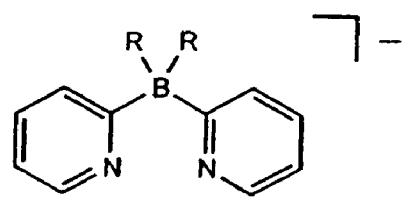
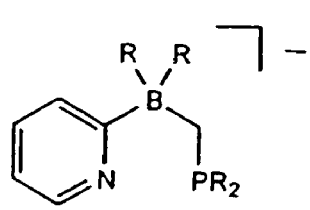
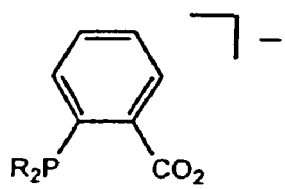
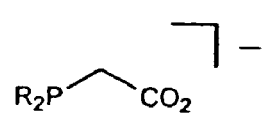
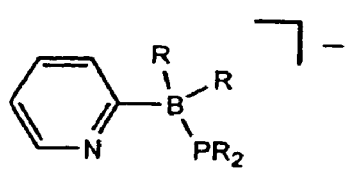
X=CH, N
E=O,S,Se,Te
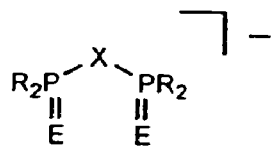
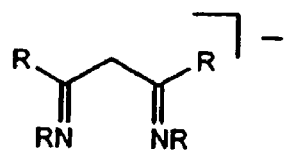
Figure 8a

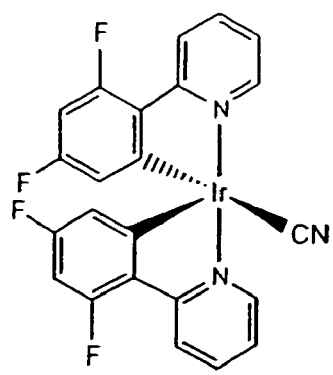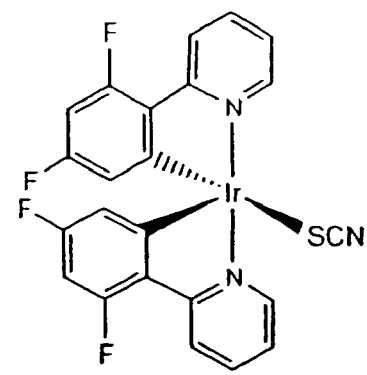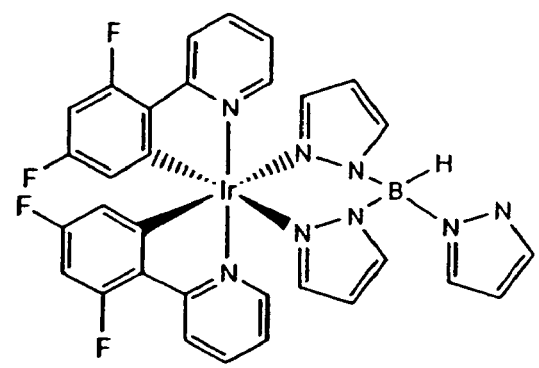
Figure 8d (ppy)Pt(acac)   (tpy)Pt(acac)   (bzq)Pt(acac)   (4,6-F$_2$ppy)Pt(acac)

(btp)Pt(acac)   (4,5-F$_2$ppy)Pt(acac)   (4,5-F$_2$ppy)Pt(pico)

FIG. 17
PRB 62
HOSTS
(a) TPD 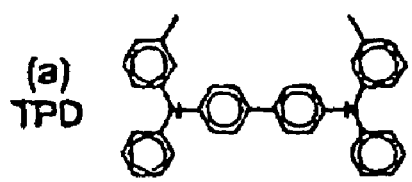
(b) BCP 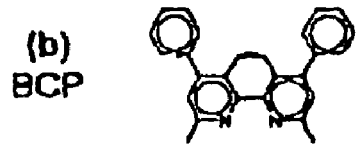
(c) CBP 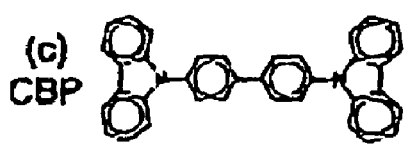
(d) Alq$_3$ 
GUESTS
(e) Ir(ppy)$_3$ 
(f) PtOEP 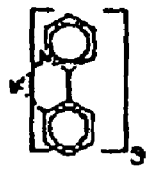
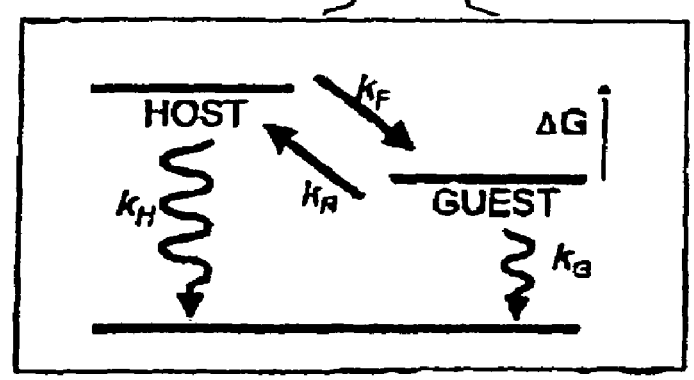

ORGANOMETALLIC COMPOUNDS AND EMISSION-SHIFTING ORGANIC ELECTROPHOSPHORESCENCE

CROSS-REFERENCE TO RELATED APPLICATIONS

This application is a continuation of U.S. Ser. No. 09/978,455, filed Oct. 16, 2001, now U.S. Pat. No. 6,939,624, which is a continuation-in-part of U.S. Ser. No. 09/637,766, filed Aug. 11, 2000, now U.S. Pat. No. 6,911,271, and also claims the benefit, under 35 U.S.C. § 119(e), of U.S. Provisional Application No. 60/283,814, filed on Apr. 13, 2001.

GOVERNMENT RIGHTS

This invention was made with Government support under Contract No. F33615-94-1-1414 awarded by DARPA. The government has certain rights in this invention.

RESEARCH AGREEMENTS

The claimed invention was made by, on behalf of, and/or in connection with one or more of the following parties to a joint university-corporation research agreement: Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention is directed to phosphorescence based organic light emitting devices that have improved electroluminescent characteristics.

BACKGROUND OF THE INVENTION

The technology of organic light emitting diodes (OLEDs) is undergoing rapid development. OLEDs originally utilized the electroluminescence produced from electrically excited molecules that emitted light from their singlet states. Such radiative emission from a singlet excited state is referred to as fluorescence. More recent work has demonstrated that higher power efficiency OLEDs can be made using molecules that emit light from their triplet state, defined as phosphorescence.

Such electrophosphorescence makes it possible for phosphorescent OLEDs to have substantially higher quantum efficiencies than are possible for OLEDs that only produce fluorescence. This is based on the understanding that the excitons created in an OLED are produced, according to simple statistical arguments as well as experimental measurements, approximately 75% as triplet excitons and 25% as singlet excitons. The triplet excitons more readily transfer their energy to triplet excited states that can produce phosphorescence whereas the singlet excitons typically transfer their energy to singlet excited states that can produce fluorescence. Since the lowest emissive singlet excited state of an organic molecule is typically at a slightly higher energy than the lowest triplet excited state, the singlet excited state may relax, by an intersystem crossing process, to the emissive triplet excited state. This means that all the exciton excitation energy may be converted into triplet state excitation energy, which then becomes available as phosphorescent emission. Thus, electrophosphorescent OLEDs have a theoretical quantum efficiency of 100%, since all the exciton excitation energy can become available as electrophosphorescence.

As a consequence, since the discovery that phosphorescent materials could be used in an OLED, Baldo et al., "*Highly Efficient Phosphorescent Emission from Organic Electroluminescent Devices*", Nature, vol. 395, 151-154, 1998, there is now much interest in finding more efficient electrophosphorescent materials.

Typically phosphorescent emission from organic molecules is less common than fluorescent emission. However, phosphorescence can be observed from organic molecules under an appropriate set of conditions. Organic molecules coordinated to lanthanide elements often phosphoresce from excited states localized on the lanthanide metal. The europium diketonate complexes illustrate one group of these types of species. Organic phosphorescence is also often observed in molecules containing heteroatoms with unshared pairs of electrons at very low temperatures. Benzophenone and 2,2'-bipyridine are such molecules. Phosphorescence can be enhanced over fluorescence by confining, preferably through bonding, the organic molecule in close proximity to an atom of high atomic number. This phenomenon, called the heavy atom effect, is created by a mechanism known as spin-orbit coupling. A related phosphorescent transition is a metal-to-ligand charge transfer (MLCT) that is observed in molecules such as tris(2-phenylpyridine)iridium(III).

However, molecules that phosphoresce from MLCT states typically emit light that is of lower energy than that observed from the unbound organic ligand. This lowering of emission energy makes it difficult to develop organic molecules that phosphoresce in the technologically useful blue and green Colors of the visible spectrum where the unperturbed phosphorescence typically occurs.

It would be desirable if more efficient electrophosphorescent materials could be found, particularly materials that produce their emission in the blue region of the spectrum.

The realization of highly efficient blue, green and red electrophosphorescence is a requirement for portable full color displays and white lighting applications with low power consumption. Recently, high-efficiency green and red organic electrophosphorescent devices have been demonstrated which harvest both singlet and triplet excitons, leading to internal quantum efficiencies ($\eta_{int}$) approaching 100%. See Baldo, M. A., O'Brien, D. F., You, Y., Shoustikov, A., Sibley, S., Thompson, M. E., and Forrest, S. R., Nature (London), 395, 151-154 (1998); Baldo, M. A., Lamansky, S., Burrows, P. E., Thompson, M. E., and Forrest, S. R., Appl. Phys. Lett., 75, 4-6 (1999); Adachi, C., Baldo, M. A., and Forrest, S. R., App. Phys. Lett., 77, 904-906, (2000); Adachi, C., Lamansky, S., Baldo, M. A., Kwong, R. C., Thompson, M. E., and Forrest, S. R., App. Phys. Lett., 78, 1622-1624 (2001); and Adachi, C., Baldo, M. A., Thompson, M. E., and Forrest, S. R., Bull. Am. Phys. Soc., 46, 863 (2001). Using a green phosphor, fac tris(2-phenylpyridine)iridium (Ir(ppy)$_3$), in particular, an external quantum efficiency ($\eta_{ext}$) of (17.6±0.5) % corresponding to an internal quantum efficiency of >85%, was realized using a wide energy gap host material, 3-phenyl-4-(1'-naphthyl)-5-phenyl-1,2,4-triazole (TAZ). See Adachi, C., Baldo, M. A., Thompson, M. E., and Forrest, S. R., Bull. Am. Phys. Soc., 46, 863 (2001). Most recently, high-efficiency ($\eta_{ext}$= (7.0±0.5) %) red electrophosphorescence was demonstrated employing bis(2-(2'-benzo[4,5-a]thienyl)pyridinato-N,C$^3$) iridium (acetylacetonate) [Btp$_2$Ir(acac)]. See Adachi, C., Lamansky, S., Baldo, M. A., Kwong, R. C., Thompson, M. E., and Forrest, S. R., App. Phys. Lett., 78, 1622-1624 (2001).

In each of these latter cases, high efficiencies are obtained by energy transfer from both the host singlet and triplet states to the phosphor triplet, or via direct trapping of charge on the phosphor, thereby harvesting up to 100% of the excited states. This is a significant improvement over what can be expected using fluorescence in either small molecule or polymer organic light emitting devices (OLEDs). See Baldo, M. A., O'Brien, D. F., Thompson, M. E., and Forrest, S. R., Phys. Rev., B 60, 14422-14428 (1999); Friend, R. H., Gymer, R. W., Holmes, A. B., Burroughes, J. H., Marks, R. N., Taliani, C., Bradley, D. D. C., Dos Santos, D. A., Bredas, J. L., Logdlund, M., Salaneck, W. R., Nature (London), 397, 121-128 (1999); and Cao, Y, Parker, I. D., Yu, G., Zhang, C., and Heeger, A. J., Nature (London), 397, 414-417 (1999). In either case, these transfers entail a resonant, exothermic process. As the triplet energy of the phosphor increases, it becomes less likely to find an appropriate host with a suitably high energy triplet state. See Baldo, M. A., and Forrest, S. R., Phys. Rev. B 62, 10958-10966 (2000). The very large excitonic energies required of the host also suggest that this material layer may not have appropriate energy level alignments with other materials used in an OLED structure, hence resulting in a further reduction in efficiency. To eliminate this competition between the conductive and energy transfer properties of the host, a route to efficient blue electrophosphorescence may involve the endothermic energy transfer from a near resonant excited state of the host to the higher triplet energy of the phosphor. See Baldo, M. A., and Forrest, S. R., Phys. Rev. B 62, 10958-10966 (2000); Ford, W. E., Rodgers, M. A. J., J. Phys. Chem., 96, 2917-2920 (1992); and Harriman, A.; Hissler, M.; Khatyr, A.; Ziessel, R. *Chem. Commun.*, 735-736 (1999). Provided that the energy required in the transfer is not significantly greater than the thermal energy, this process can be very efficient.

Organic light emitting devices (OLEDs), which make use of thin film materials that emit light when excited by electric current, are expected to become an increasingly popular form of flat panel display technology. This is because OLEDs have a wide variety of potential applications, including cellphones, personal digital assistants (PDAs), computer displays, informational displays in vehicles, television monitors, as well as light sources for general illumination. Due to their bright colors, wide viewing angle, compatibility with full motion video, broad temperature ranges, thin and conformable form factor, low power requirements and the potential for low cost manufacturing processes, OLEDs are seen as a future replacement technology for cathode ray tubes (CRTs) and liquid crystal displays (LCDs), which currently dominate the growing $40 billion annual electronic display market. Due to their high luminous efficiencies, electrophosphorescent OLEDs are seen as having the potential to replace incandescent, and perhaps even fluorescent, lamps for certain types of applications.

Light emission from OLEDs is typically via fluorescence or phosphorescence. As used herein, the term "phosphorescence" refers to emission from a triplet excited state of an organic molecule and the term fluorescence refers to emission from a singlet excited state of an organic molecule.

Successful utilization of phosphorescence holds enormous promise for organic electroluminescent devices. For example, an advantage of phosphorescence is that all excitons (formed by the recombination of holes and electrons in an EL), which are formed either as a singlet or triplet excited state, may participate in luminescence. This is because the lowest singlet excited state of an organic molecule is typically at a slightly higher energy than the lowest triplet excited state. This means that, for typical phosphorescent organometallic compounds, the lowest singlet excited state may rapidly decay to the lowest triplet excited state from which the phosphorescence is produced. In contrast, only a small percentage (about 25%) of excitons in fluorescent devices are capable of producing the fluorescent luminescence that is obtained from a singlet excited state. The remaining excitons in a fluorescent device, which are produced in the lowest triplet excited state of an organic molecule, are typically not capable of being converted into the energetically unfavorable higher singlet excited states from which the fluorescence is produced. This energy, thus, becomes lost to radiationless decay processes that heat-up the device.

SUMMARY OF THE INVENTION

The present invention is directed to emissive phosphorescent organometallic compounds that produce improved electroluminescence, organic light emitting devices employing such emissive phosphorescent organometallic compounds, and methods of fabricating such organic light emitting devices.

Specific embodiments of the present invention are directed to OLEDs using emissive phosphorescent organometallic compounds that produce improved electrophosphorescence in the blue region of the visible spectrum.

The present invention is directed, in addition, to a method of selecting organometallic compounds that have improved electroluminescent properties, for example, in the blue region of the visible spectrum.

The present invention is also directed to an organic light emitting layer including a host material and a guest material dispersed in the host material, the guest material having a lowest triplet excited state having a radiative decay rate of greater than about $1 \times 10^5$ or about $1 \times 10^6$ per second and wherein the energy level of the lowest triplet excited state of the host material is lower than the energy level of the lowest triplet excited state of the guest material. The sum of the radiative and non-radiative decay rates of the host triplet is preferably not greater than about $5 \times 10^3$/sec, and more preferably, not greater than about $1 \times 10^3$/sec.

The present invention is also directed to an organic light emitting layer including a host material having a lowest triplet excited state having a decay rate of less than about 1 per second; a guest material dispersed in the host material, the guest material having a lowest triplet excited state having a radiative decay rate of greater than about $1 \times 10^5$ or about $1 \times 10^6$ per second and wherein the energy level of the lowest triplet excited state of the host material is lower than the energy level of the lowest triplet excited state of the guest material.

BRIEF DESCRIPTION OF THE DRAWINGS

For the purpose of further illustrating the invention, representative embodiments are shown in the accompanying figures, it being understood that the invention is not intended to be limited to the precise arrangements and instrumentalities shown.

FIG. 1a shows photoluminescent (PL) spectra in a dilute ($10^{-5}$M) chloroform solution of three different iridium-based phosphors: Iridium(III)bis(4,6-di-fluorophenyl)-pyridinato-N, $C^{2'}$) picolinate (FIrpic) (curve a); bis(4,6-difluorophenyl)-pyridinato-N, C$^{2'}$)iridium(acetylacetonate) [FIr(acac)] (curve b); and bis(2-phenylpyridinato-N,C$^{2'}$)iridium(acetylacetonate) [ppy$_2$Ir(acac)] (curve c); as well as the molecular structures of these iridium complexes: FIrpic (structure a); FIr(acac) (structure b); and ppy$_2$Ir(acac) (structure c).

FIG. 1*b* shows shows the electroluminescence spectra of the following OLED structure: ITO/CuPc (10 nm)/α-NPD (30 nm)/CBP host doped with 6% FIrpic (30 nm)/BAlq (30 nm)/LiF (1 nm)/Al (100 nm).

FIG. 2 shows external electroluminescent quantum ($\eta_{ext}$: filled squares) and power ($\eta_P$: open Circles) efficiencies as functions of current density for the following OLED structure: ITO/CuPc (10 nm)/α-NPD(30 nm)/CBP host doped with 6% FIrpic (30 nm)/BAlq (30 nm)/LiF (1 nm)/Al (100 nm). The inset to FIG. 2 shows an energy level diagram of triplet levels of a CBP host and a FIrpic guest.

FIG. 3 shows a streak image of the transient decay of a 6%-FIrpic:CBP film (100 nm thick) on a Si substrate under nitrogen pulse excitation (~500 ps) at T=100 K. Also shown is the CBP phosphorescence spectrum obtained at 10 K.

FIG. 4 shows the transient photoluminescence decay characteristics of a 100 nm thick 6%-FIrpic:CBP film on a Si substrate under nitrogen pulse excitation (~500 ps) at T=50 K, 100 K, 200 K and 300 K. The inset to FIG. 4 shows the temperature dependence of the relative photoluminescence (PL) efficiency ($\eta_{PL}$) of FIrpic doped into CBP.

FIGS. 5*a*, 5*b* and 5*c* show generic representative examples of the at least one mono-anionic, bidentate, carbon-coordination ligand of the present invention.

FIGS. 8*a* through 8*d* show the chemical structures of the phosphorescent organometallic compounds from FIGS. 7*a* through 7*r*, along with some of the ligands comprising these compounds.

FIG. 17 shows the molecular structures of some materials studied for the present invention and a view of the triplet dynamics in a guest-host system of the present invention.

DETAILED DESCRIPTION

The present invention will now be described in detail for specific preferred embodiments of the invention. These embodiments are intended only as illustrative examples and the invention is not to be limited thereto.

The phosphorescent organometallic compounds of the present invention are comprised of: (a) a heavy transition metal such as Ir, but not limited to Ir, which produces efficient phosphorescent emission at room temperature from a mixture of MLCT and π-π* ligand states; (b) wherein the metal is bound to at least one mono-anionic, bidentate, carbon-coordination ligand substituted with electron donating and/or electron withdrawing substituents that shift the emission, relative to the un-substituted ligand, to either the blue, green or red region of the visible spectrum; and (c) wherein the metal is bound to at least one non-mono-anionic, bidentate, carbon-coordination ligand, which may be substituted or un-substituted, that causes the emission to have a well defined vibronic structure.

A carbon-coordination ligand is a ligand that is bound to the metal atom via a carbon-metal bond. In view of what one skilled in the art might view as a strict definition of organometallic compounds, such as described in Inorganic Chemistry, by Gary L. Miessler and Donald A. Tarr, 2nd edition, Prentice Hall, 1999, the compounds of the present invention are referred to herein as organometallic compounds since these compounds include a metal-carbon bond.

The phosphorescent organometallic compounds of the present invention have at least one carbon-coordination ligand wherein the at least one carbon-coordination ligand is a mono-anionic ligand. That is, the metal atom is bound to only one carbon atom of the at least one carbon-coordination ligand. Furthermore, the at least one mono-anionic, carbon-coordination ligand of the present invention is a bidentate ligand. A bidentate ligand has two points at which it attaches to a central atom, in this case, the metal atom. Thus, the phosphorescent organometallic compounds of the present invention have at least one mono-anionic, bidentate, carbon-coordination ligand.

Figure 5B:
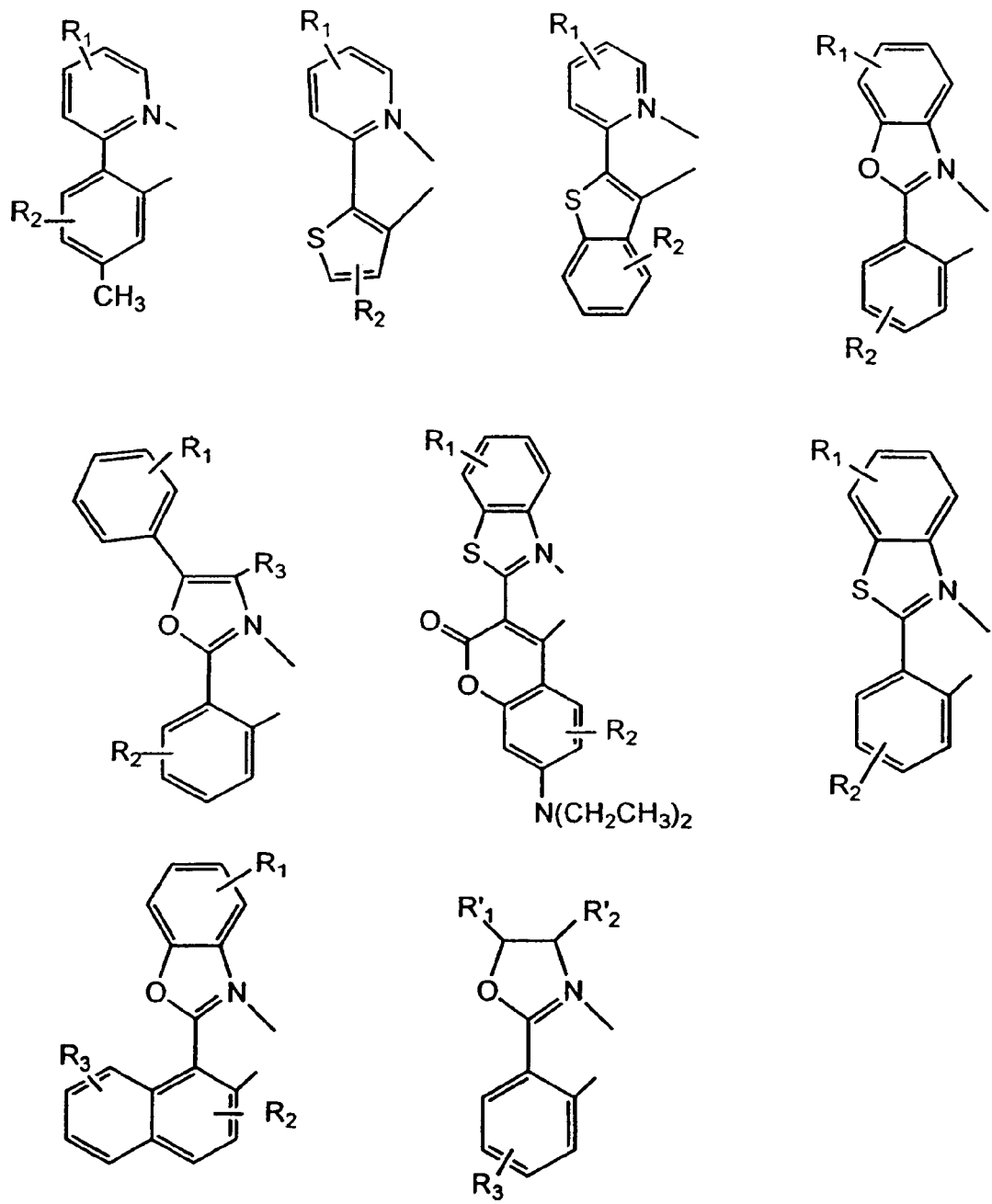
Figure 5C:
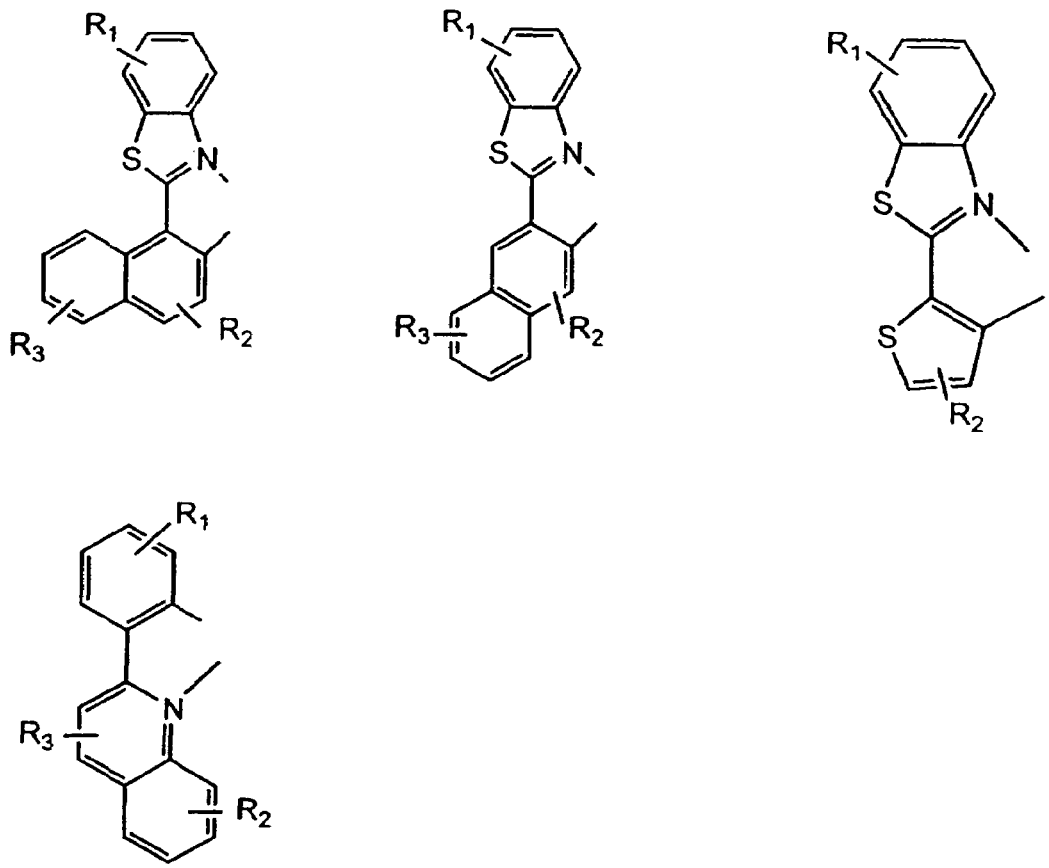
Figure 5D:
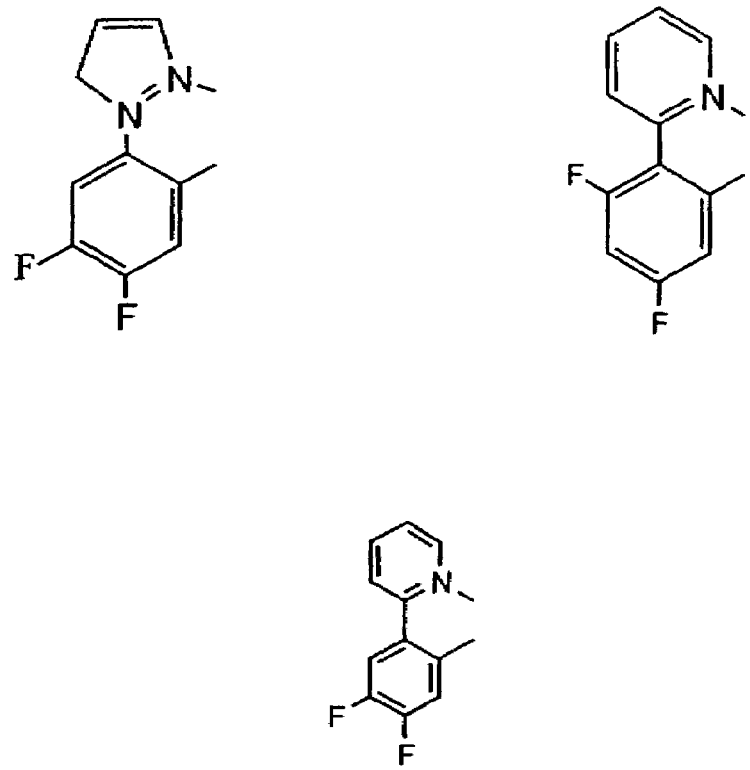
FIG. 5*d* shows three specific examples of the at least one mono-anionic, bidentate, carbon-coordination ligand of the present invention with specific substituents.

The at least one mono-anionic, bidentate, carbon-coordination ligand of the present invention is substituted with electron donating and/or electron withdrawing substituents that shift the emission, relative to the un-substituted ligand, to either the blue, green or red region of the visible spectrum. The particular substituents used on particular ligands will depend upon the desired shift in emission. Generic representative examples of the at least one mono-anionic, bidentate, carbon-coordination ligand of the present invention are listed in FIGS. 5a, 5b and 5c. In addition, two specific examples of the at least one mono-anionic, bidentate, carbon-coordination ligand of the present invention with specific substituents are listed in FIG. 5d. As can be seen in FIGS. 5a, 5b and 5c, the at least one mono-anionic, bidentate, carbon-coordination ligand of the present invention can form a cyclometallated ring that includes the organometallic carbon-metal bond and a dative bond between the metal atom and a nitrogen, sulfur or oxygen group. The carbon atom that is bound to the metal may be present as part of a substituted or unsubstituted, saturated hydrocarbon; a substituted or unsubstituted, aromatic system, for example, phenylene or naphthalene compounds; or a substituted or unsubstituted heterocyclic system, which might include, for example, substituted or unsubstituted thiophenes, furans, pyridines and pyrroles. The group in the cyclometallated ring that forms a dative bond with the metal atom may be independently selected also to include a substituted or unsubstituted, saturated hydrocarbon; a substituted or unsubstituted, aromatic system, for example, phenylene or naphthalene compounds; or a substituted or unsubstituted heterocyclic system, which might include, for example, thiophenes, furans, pyridines and pyrroles. One of these aforementioned groups must be substituted, however, because the at least one mono-anionic, bidentate, carbon-coordination ligand of the present invention is substituted with electron donating and/or electron withdrawing substituents that shift the emission relative to the un-substituted ligand.

The preferred metals of the present invention are metals that can provide strong spin-orbit coupling of the metal atom with the at least one mono-anionic, bidentate, carbon-coordination ligand. Such metals include, in particular, the heavy metals having an atomic number of at least 72, such as Os, Ir, Pt and Au, with Ir and Pt being particularly preferred metals.

Figure 6A:
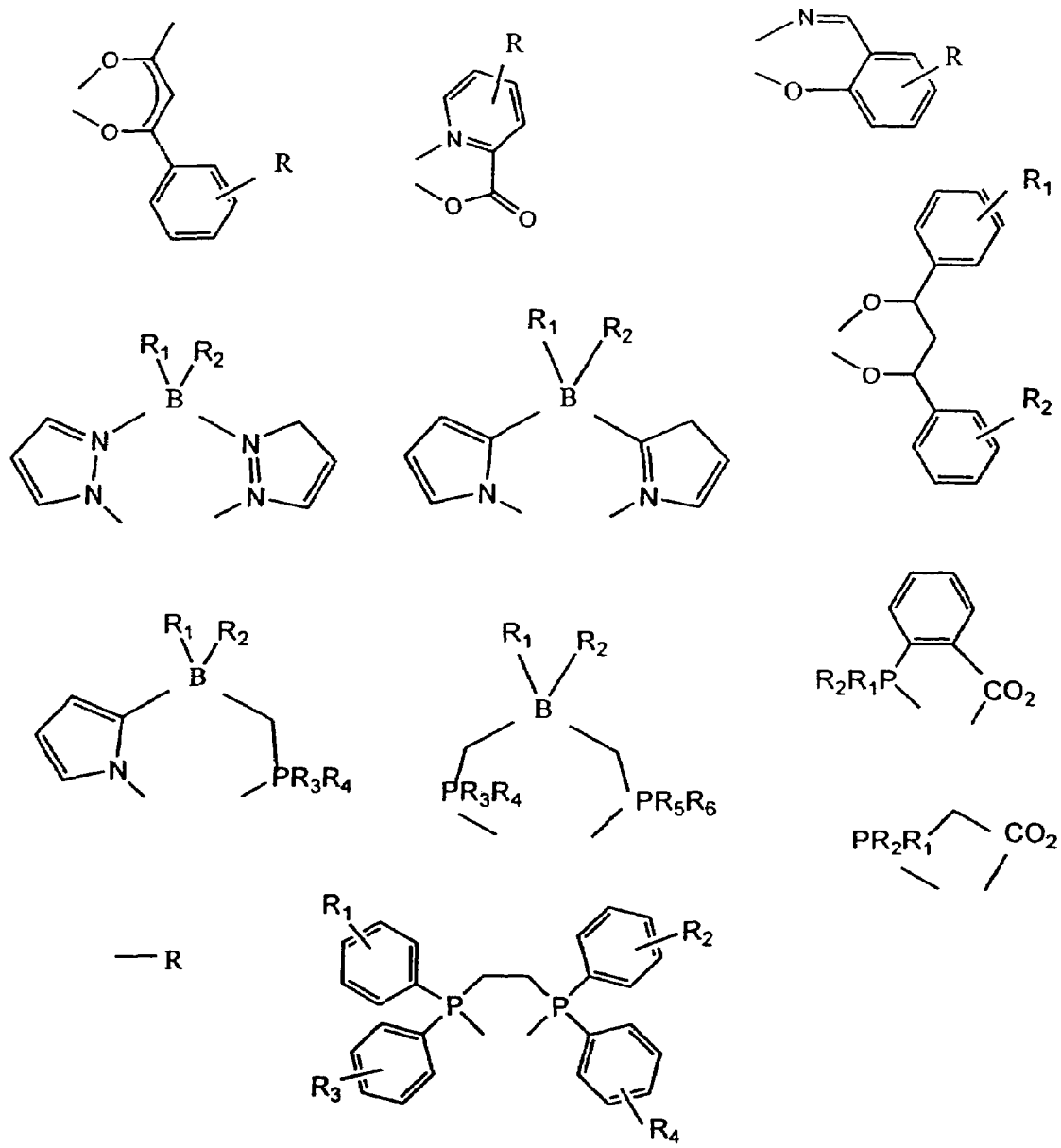
FIGS. 6*a* and 6*b* show generic representative examples of the at least one non-mono-anionic, bidentate, carbon-coordination ligand of the present invention.
Figure 6B:
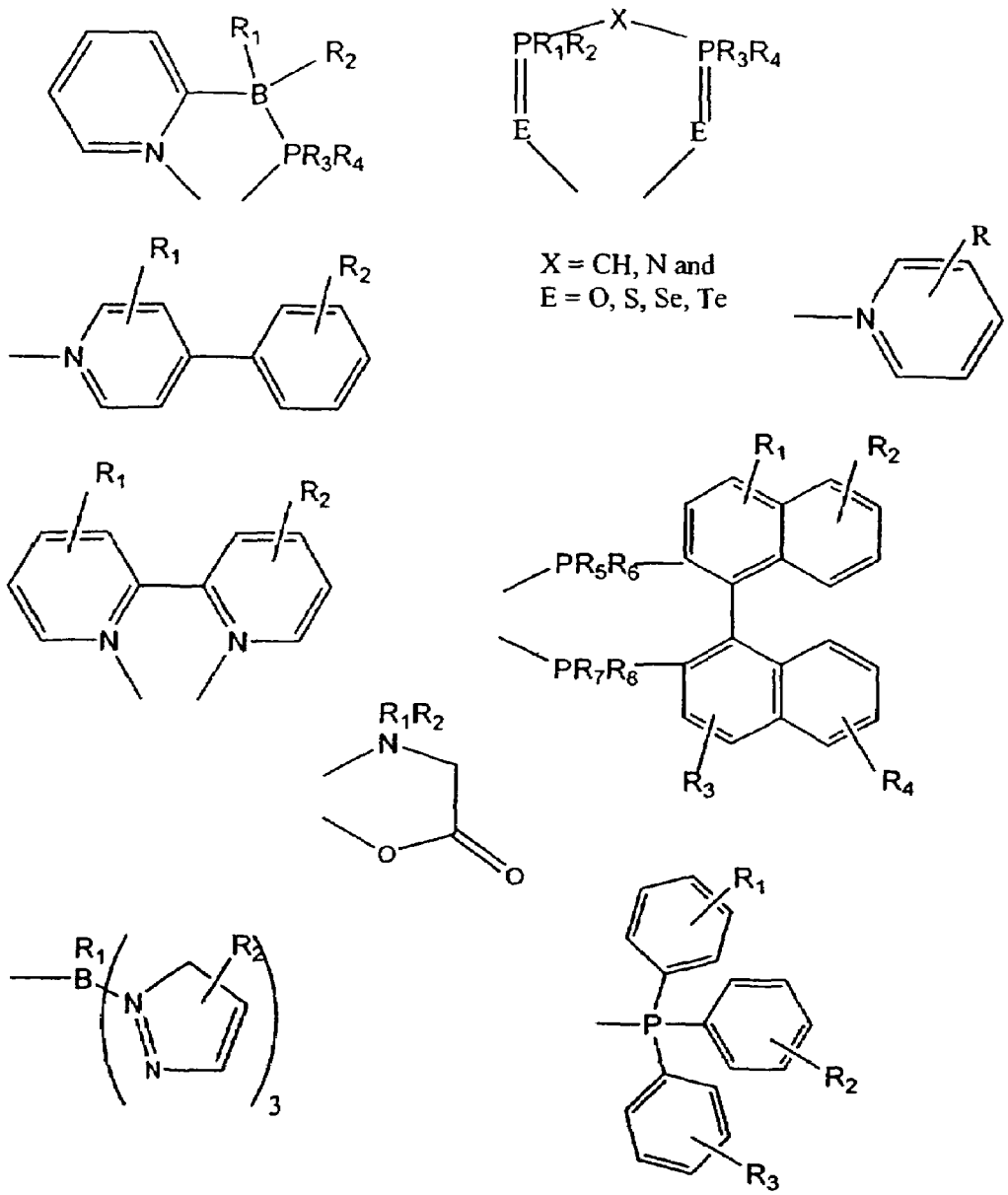
Figure 6C:
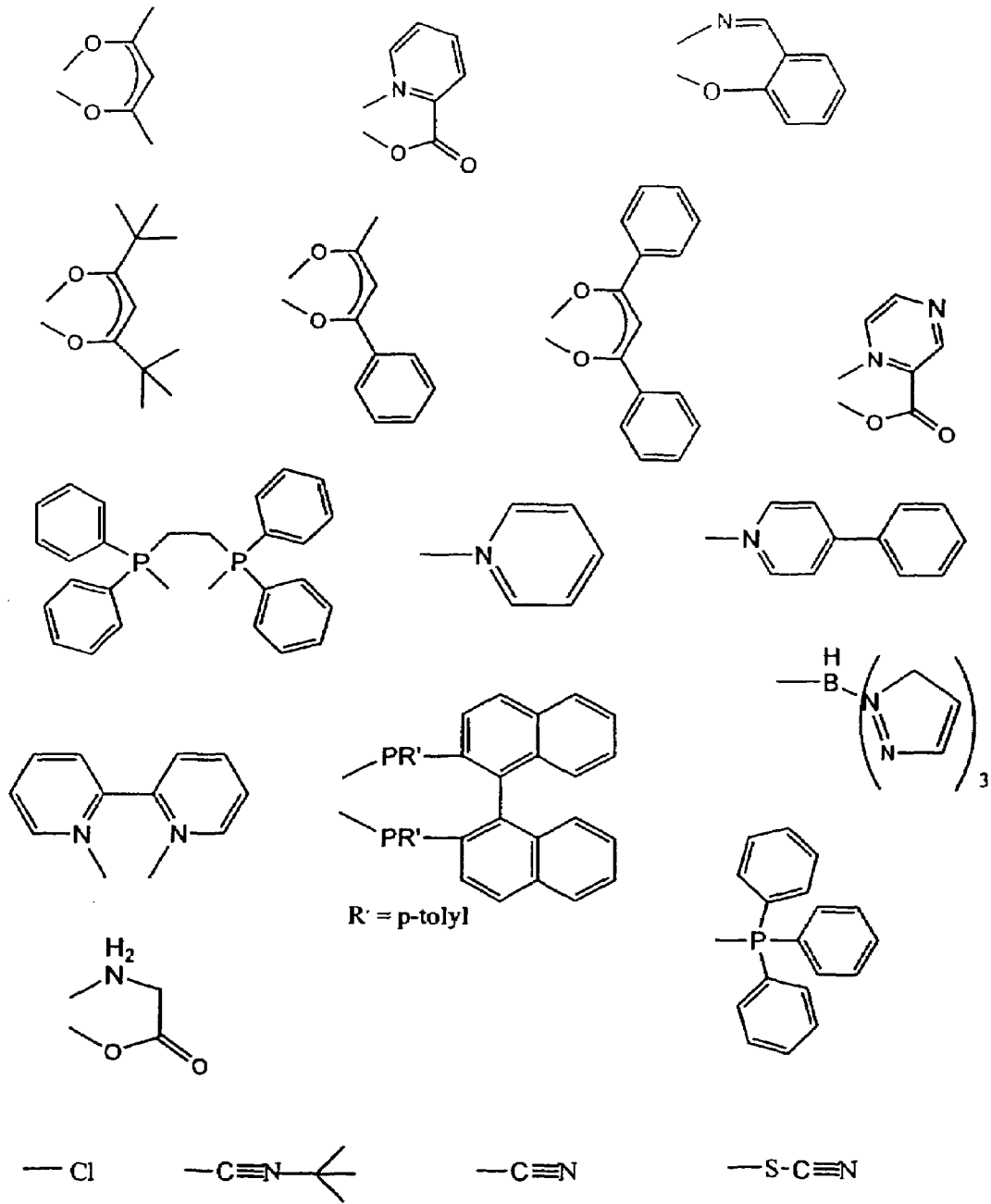
FIG. 6*c* shows specific examples of the at least one non-mono-anionic, bidentate, carbon-coordination ligand of the present invention with specific substituents.

In addition to being bound to at least one mono-anionic, bidentate, carbon-coordination ligand, the metal atom of the organometallic compounds of the present invention is also bound to at least one non-mono-anionic, bidentate, carbon-coordination ligand. The at least one non-mono-anionic, bidentate, carbon-coordination ligand of the present invention is either not mono-anionic, not bidentate, not a carbon-coordination ligand, or some combination thereof. The at least one non-mono-anionic, bidentate, carbon-coordination ligand causes the emission to have a well defined vibronic structure, and generic representative examples thereof are listed in FIGS. 6a and 6b. In addition, specific examples of the at least one non-mono-anionic, bidentate, carbon-coordination ligand of the present invention with specific substituents are listed in FIG. 6c.

In one embodiment of the organometallic compounds of the present invention, the organometallic compound includes, in particular, a metal atom bound to a single carbon-coordination ligand, wherein the carbon-coordination ligand is a mono-anionic carbon-coordination ligand. In particular, the metal atom is bound to only one carbon atom of the carbon-coordination ligand. Thus, while the organometallic compounds that are used in the OLEDs of the present invention include more than one ligand, in this embodiment of the present invention only one ligand is a carbon-coordination ligand. Thus, in this embodiment of the present invention the organometallic compounds include only one carbon-metal bond.

In this same embodiment of the present invention, the carbon-coordination ligand is preferably selected from those ligands that exhibit strong charge transfer absorption characteristics, for example, a molar absorptivity of at least 1,000 L/mole-cm, preferably, at least about 2,000-4,000 L/mole-cm. Such absorption bands involve transfer of electrons from molecular orbitals that are primarily ligand in character to orbitals that are primarily metal in character or, alternatively, from orbitals that are primarily metal in character to molecular orbitals that are primarily ligand in character. Miessler and Tarr. Such an excitation mechanism results in a charge transfer transition that may be designated as a ligand-to-metal charge transfer (LMCT) or as a metal-to-ligand charge transfer (MLCT), respectively. The former may be characterized as a partial reduction of the metal atom and the latter as a partial oxidation of the metal atom.

Selection of a carbon-coordination ligand to give a high molar absorptivity of the organometallic compound results in an organometallic compound that is capable of providing highly efficient electroluminescence when used in an OLED. However, rather than functioning as strongly absorbing species in the OLED, such organometallic compounds have highly emissive excited states that are produced when a voltage is applied across the OLED. The high molar absorptivities of such ligands may be used to select ligands that produce highly efficient electroluminescence in an OLED. Such ligands may be selected to have empty pi-symmetry orbitals on the ligands that become acceptor orbitals upon absorption of light.

In this same embodiment of the present invention, the ligand is preferably selected, in particular, so as to give a strong metal-to-ligand charge transfer (MLCT) absorption band. Such ligands are selected to have empty anti-bonding $\pi^*$ orbitals on the ligands that become acceptor orbitals upon absorption of light. As representative embodiments of the present invention, the carbon-coordination ligand may be selected from the class of materials such as described, for example, in comprehensive Coordination chemistry, Vols. 1-7, G. Wilkinson, Ed., Pergamon Press, 1987.

In this same embodiment of the present invention, in addition to being bound to a single mono-anionic carbon-coordination ligand, the metal atom of the organometallic compound is also bound to one or more additional ligands, each of which are all non-carbon-coordination ligands. A non-carbon-coordination ligand is one that does not form any metal-carbon bonds with the metal atom of the organometallic compound. Preferably, in this same embodiment of the present invention, a metal to ligand charge transfer complex (MLCT) is employed, where the non-carbon-coordination ligands are preferably ligands having a strong electrophilic character such that the ligands draw electrons away from the metal atom. Representative non-carbon-coordination ligands may also be selected, for example, from Comprehensive Coordination chemistry, Vols. 1-7, G. Wilkinson, Ed., Pergamon Press, 1987.

Without intending to be limited to the theory of how the present invention works, it is believed that the improved electroluminescent properties that are observed for the OLEDs of the present invention may be attributed to a combination of factors. For example, it is believed that selection of heavy metals that are capable of forming metal-to-ligand charge transfer (MLCT) states with carbon-coordination ligands that have empty $\pi^*$ orbitals, such phosphorescent materials produce highly efficient electro-phosphorescent OLEDs. The electroluminescence from representative organometallic compounds of the present invention shows a vibronic fine structure that indicates that the emission is from an excited state that has a wave function represented by a mixture of the MLCT state of the organo-metallic compound and the excited triplet state of the carbon-coordination ligand. Since the radiative emission is from a triplet excited state, the emission is referred to as phosphorescence.

It is further believed a higher energy radiative emission may be achieved by including electron-withdrawing groups on the carbon-coordination ligand and/or by selecting the non-carbon-coordination ligand to have a strong electron withdrawing character. Without being limited to the precise theory of how the higher energy radiative emissive may be achieved, it is believed that the electron-withdrawing groups tend to remove electron density from the highest occupied molecular orbitals (HOMO) that include the ligand and the metal atom, thus altering the relative energy levels of the ground state and the excited state such that the overall MLCT transition energy from the ground state to the excited state increases. The preferred organometallic compounds for certain embodiments of the present invention include, thus, strong electron-withdrawing groups on the carbon-coordination ligand and/or non-carbon-coordination ligands having a strong electron-withdrawing character.

Another aspect of the present invention relates to the discovery that OLEDs incorporating emissive organometal-lic compounds having a single mono-anionic carbon-coordination ligand have substantially higher external quantum efficiencies than compounds with bis-substituted carbon-coordination ligands. For example, the compound having the chemical structure [(ppy)Pt(acac)] was found to produce strong photophosphorescence at room temperature. In contrast, a compound having the structure [Pt(Ppy)$_2$] was found not to produce any visible photophosphoresce at room temperature.

Figure 7A:
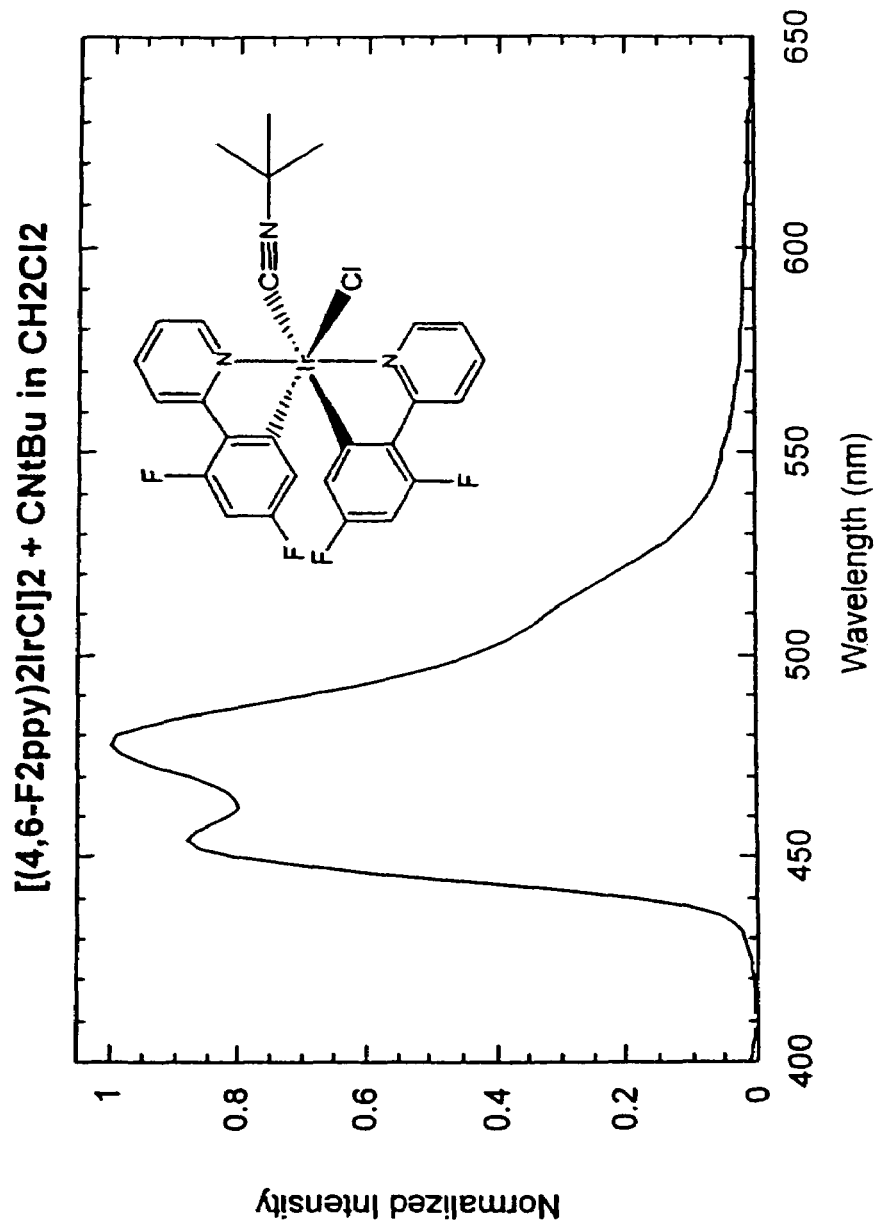
FIGS. 7*a* through 7*r* show representative examples of the phosphorescent organometallic compounds of the present invention, along with their emission spectra.
Figure 7B:
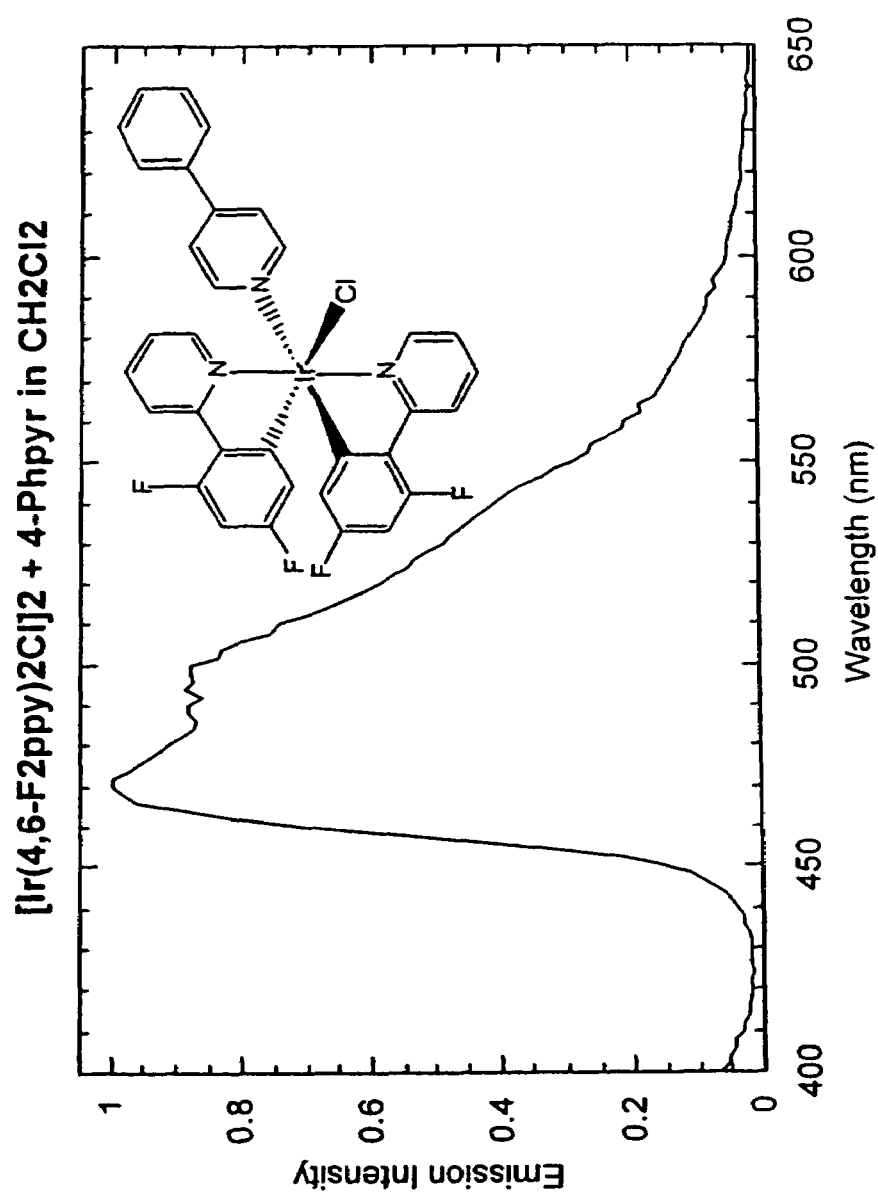
Figure 7C:
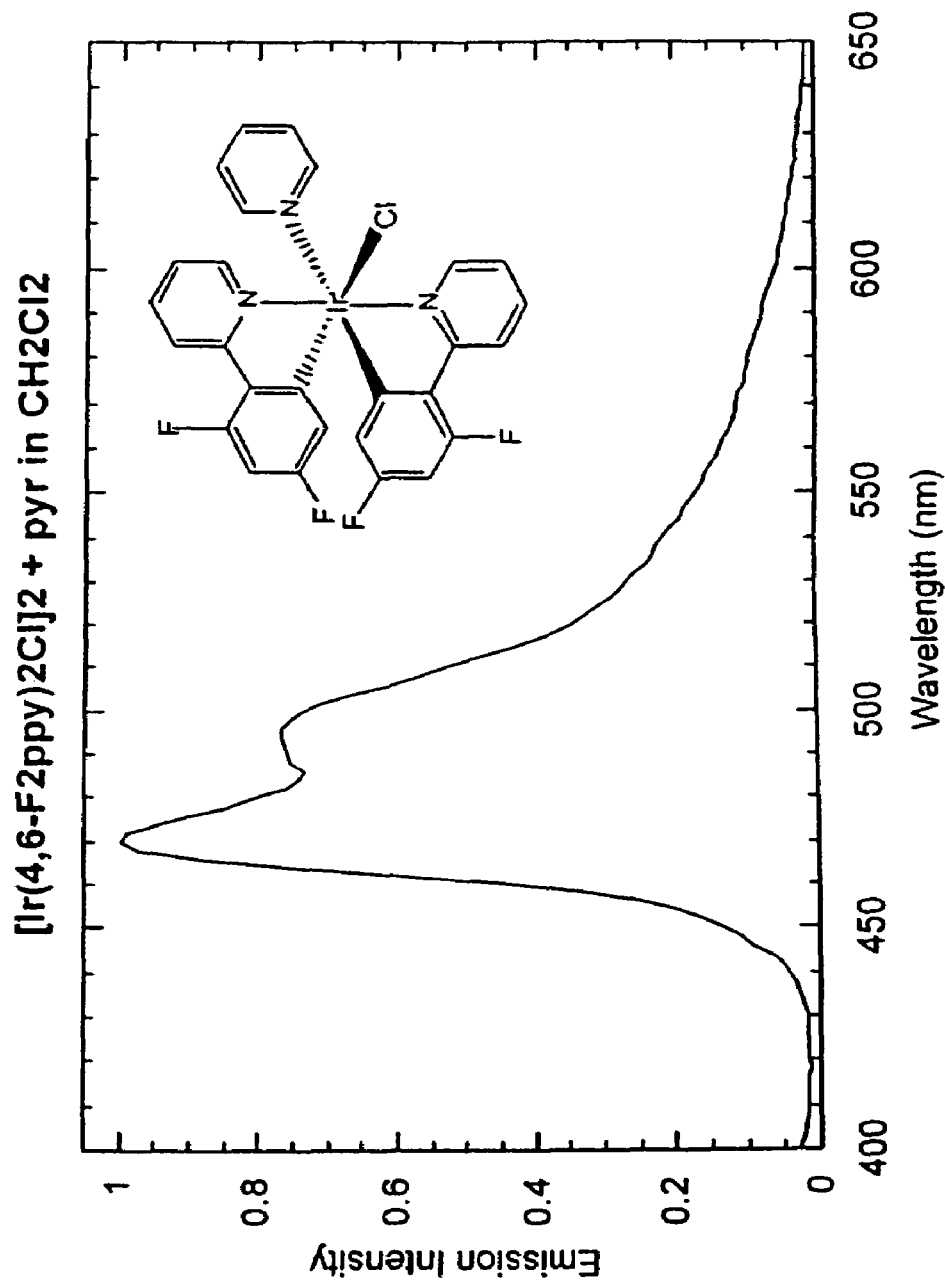
Figure 7D:
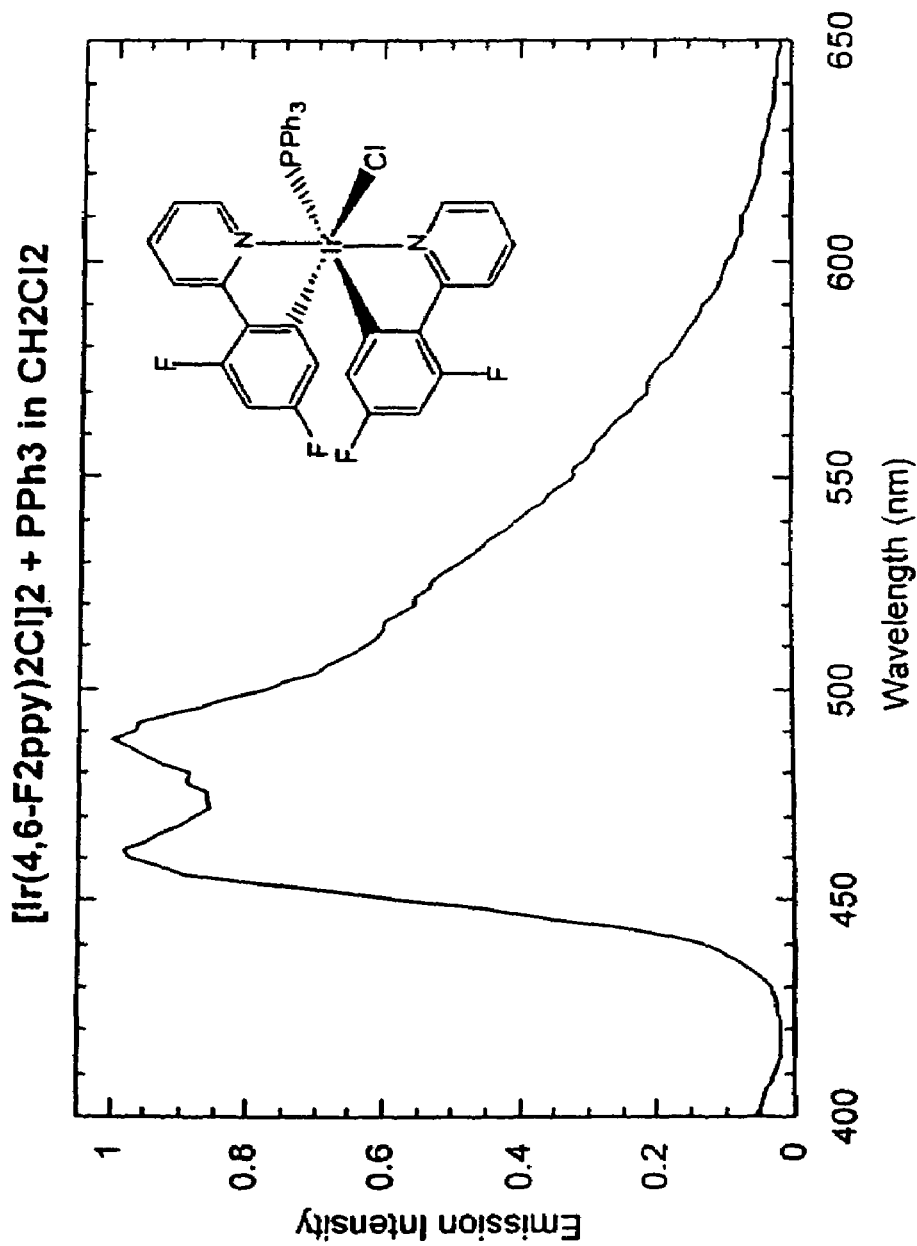
Figure 7E:
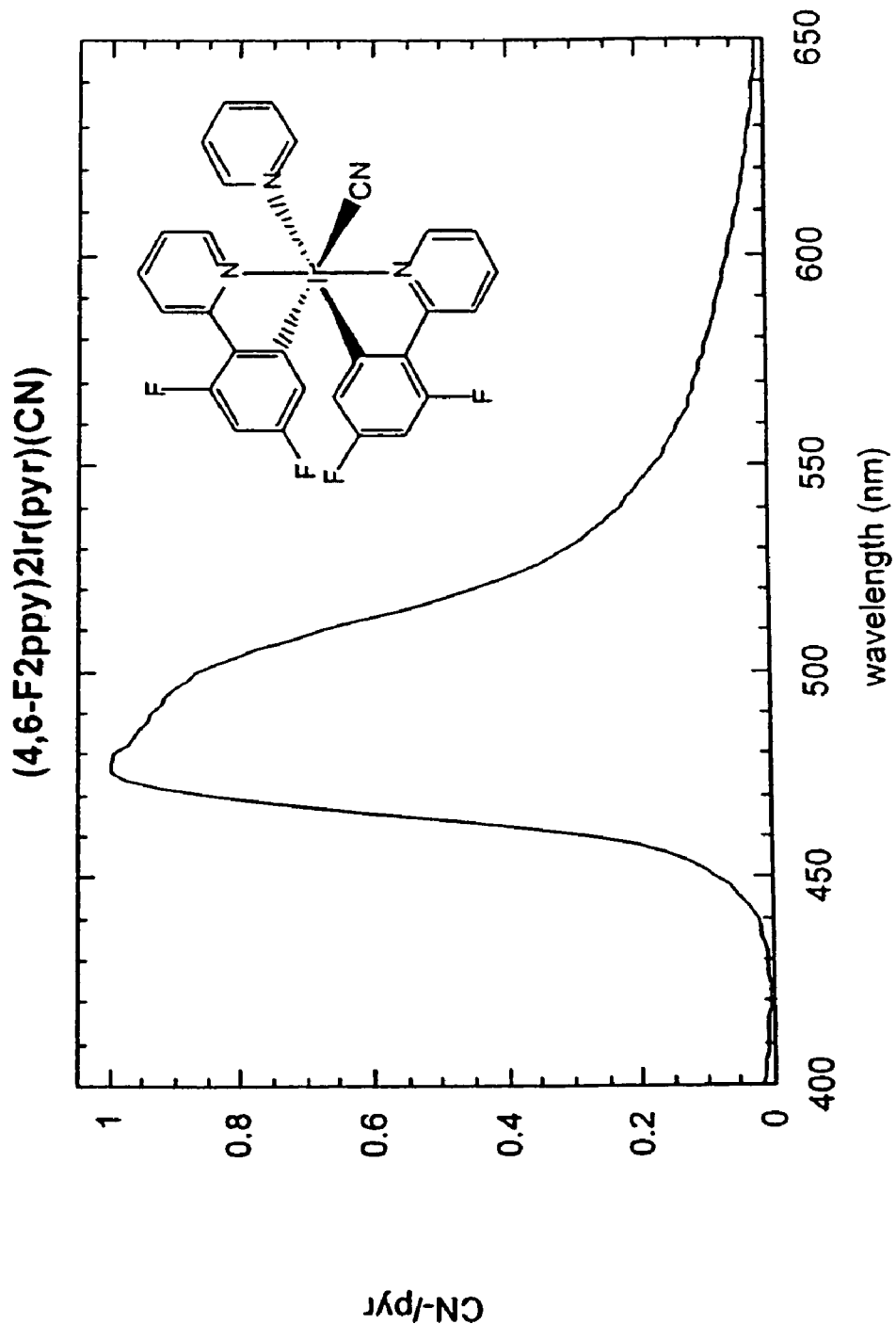
Figure 7F:
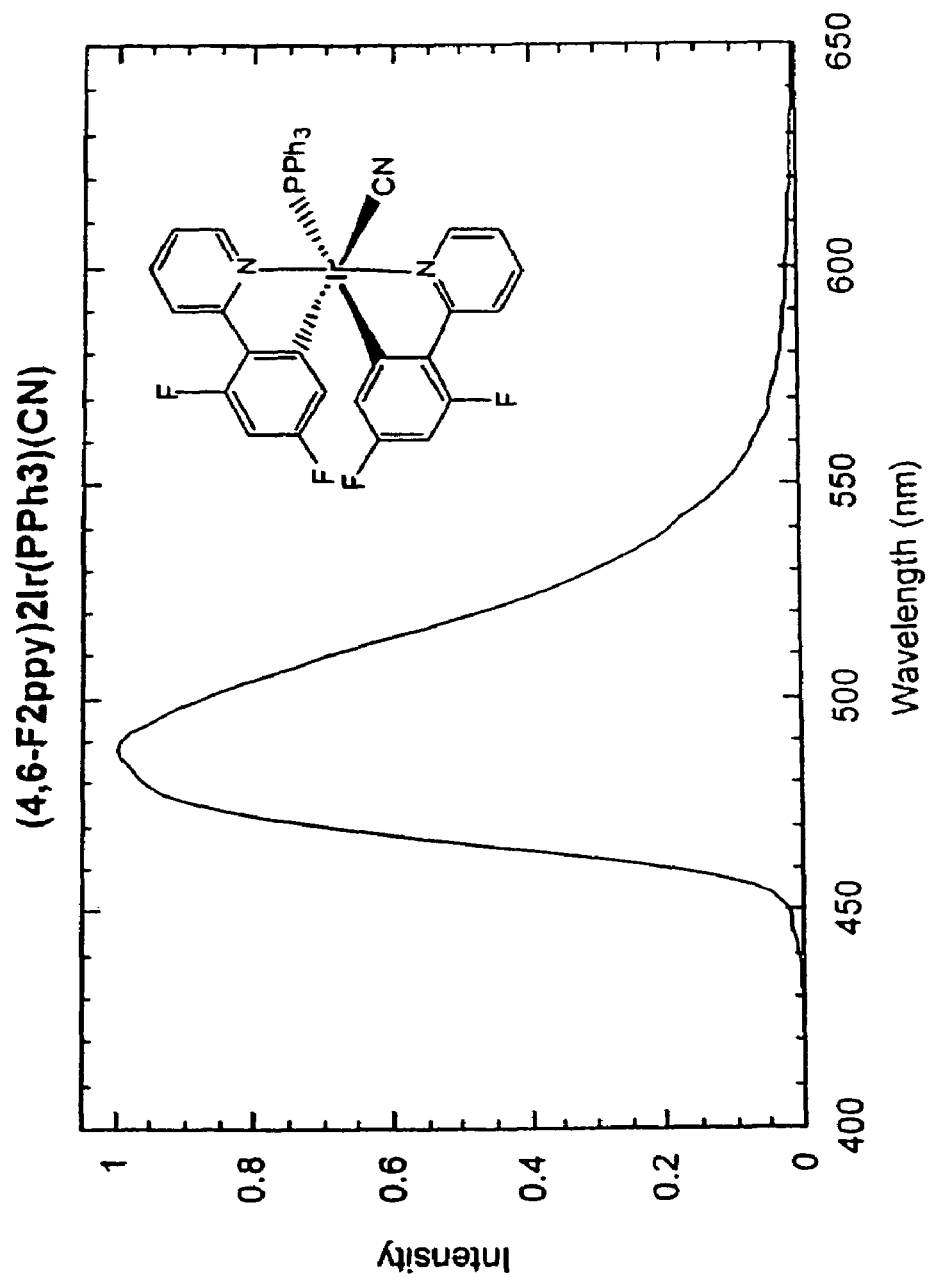
Figure 7G:
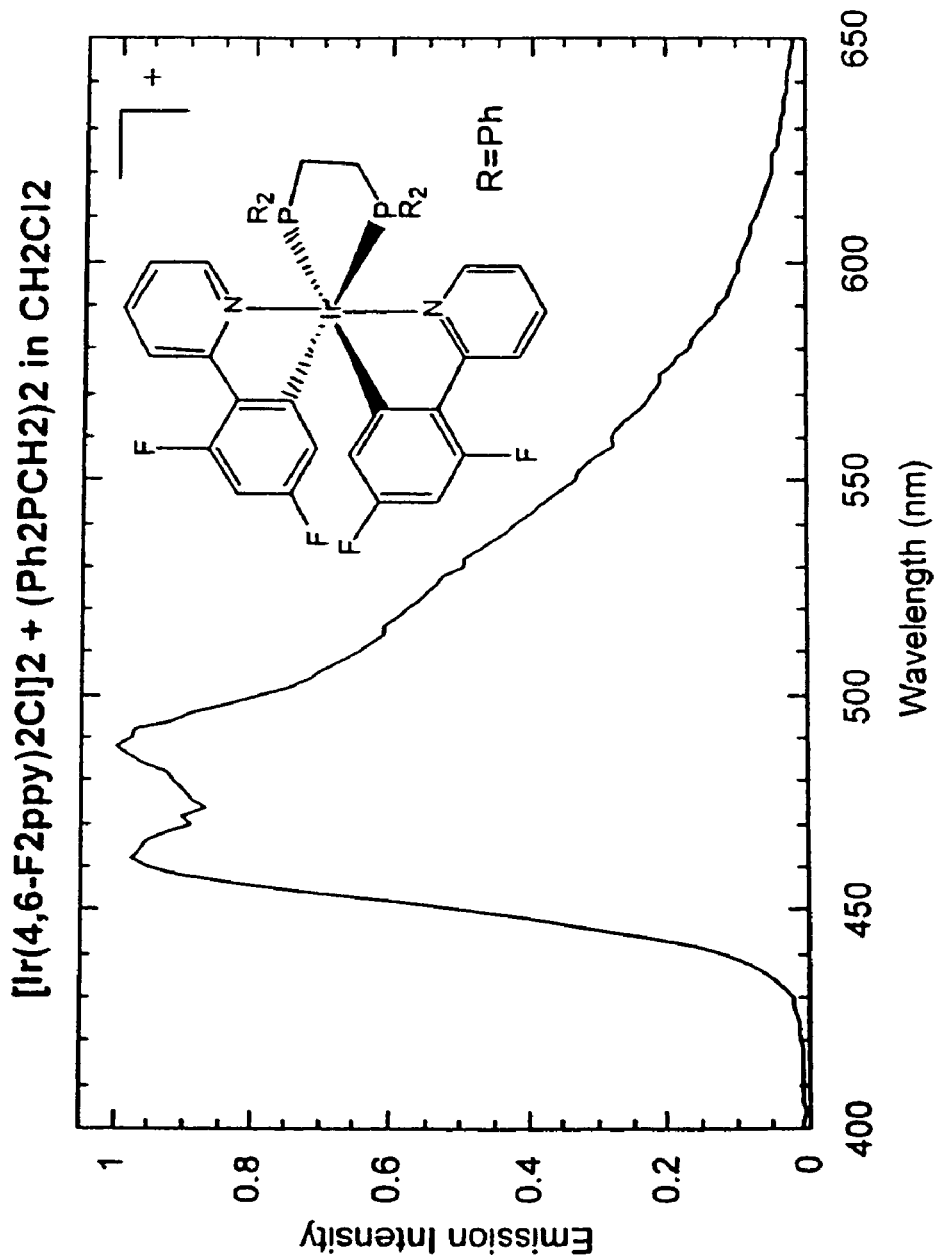
Figure 7H:
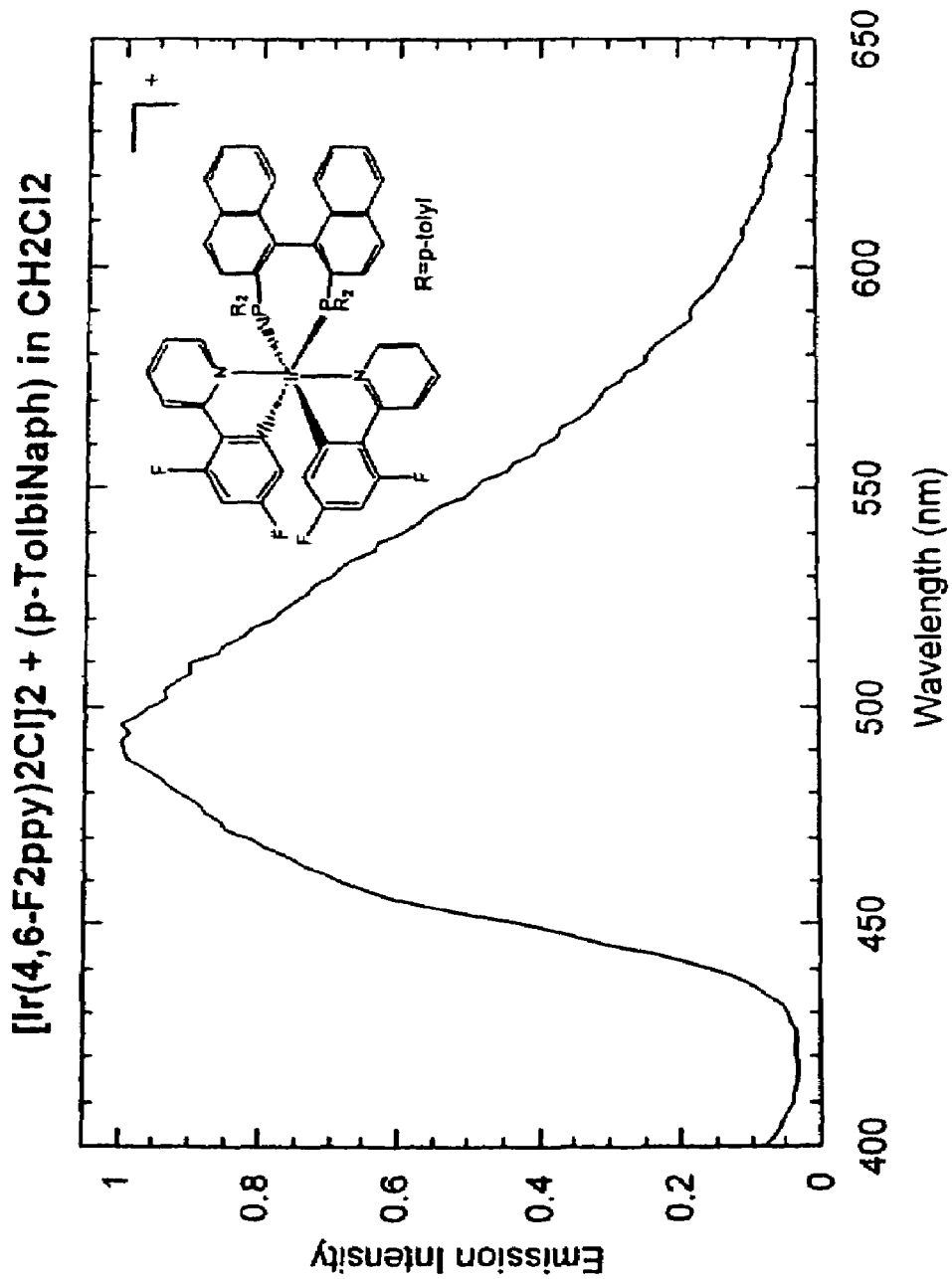
Figure 7I:
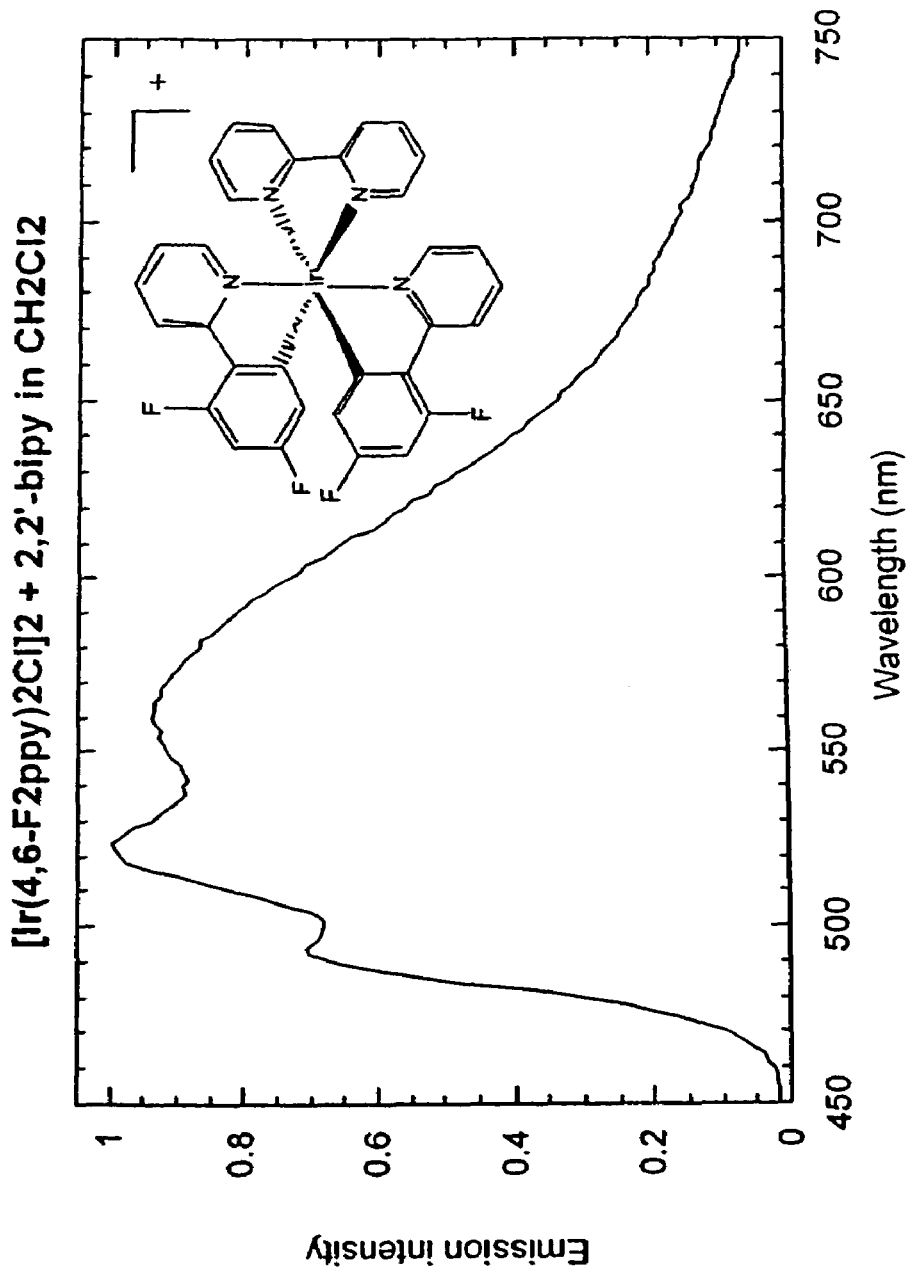
Figure 7J:
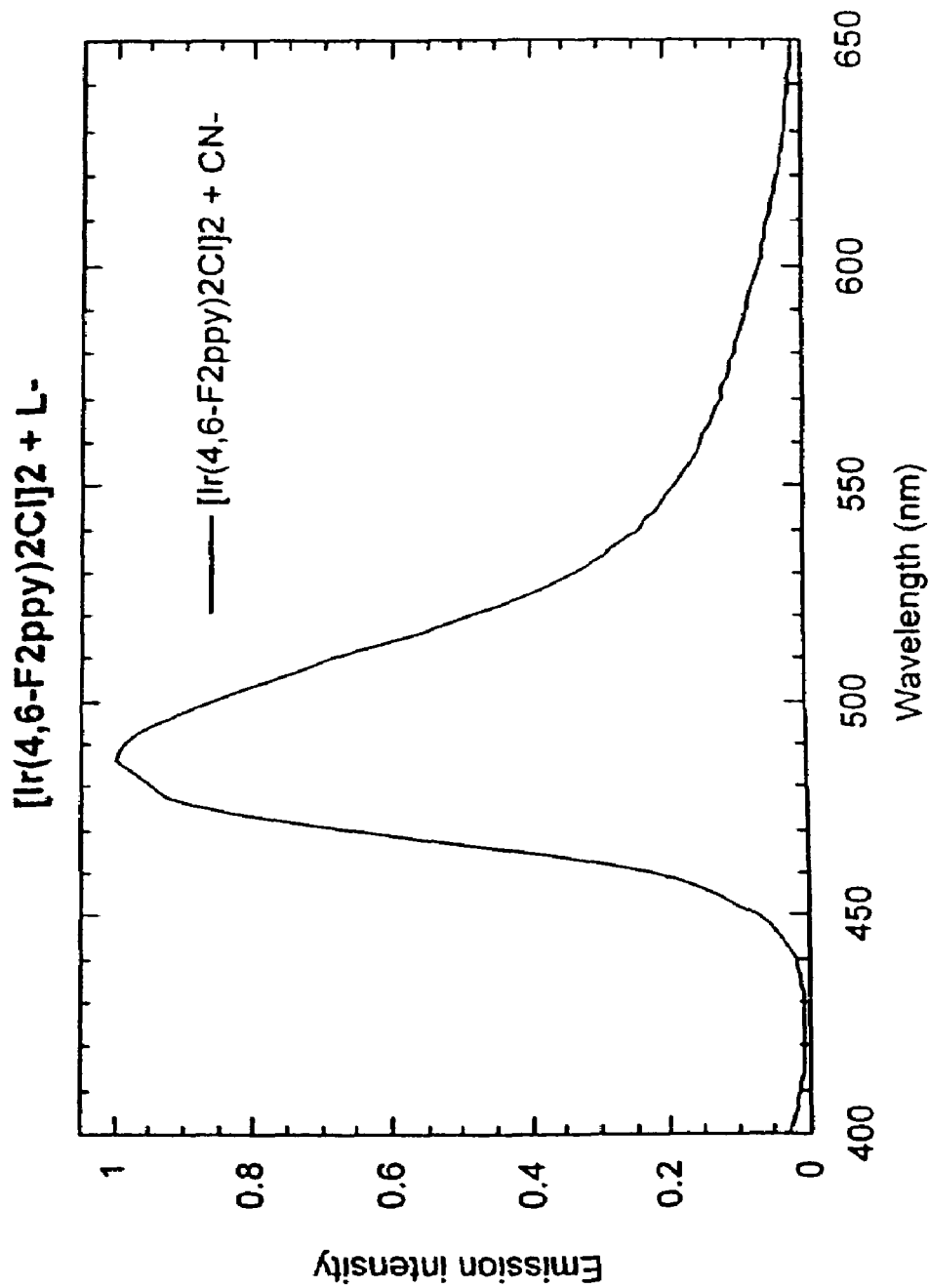
Figure 7K:
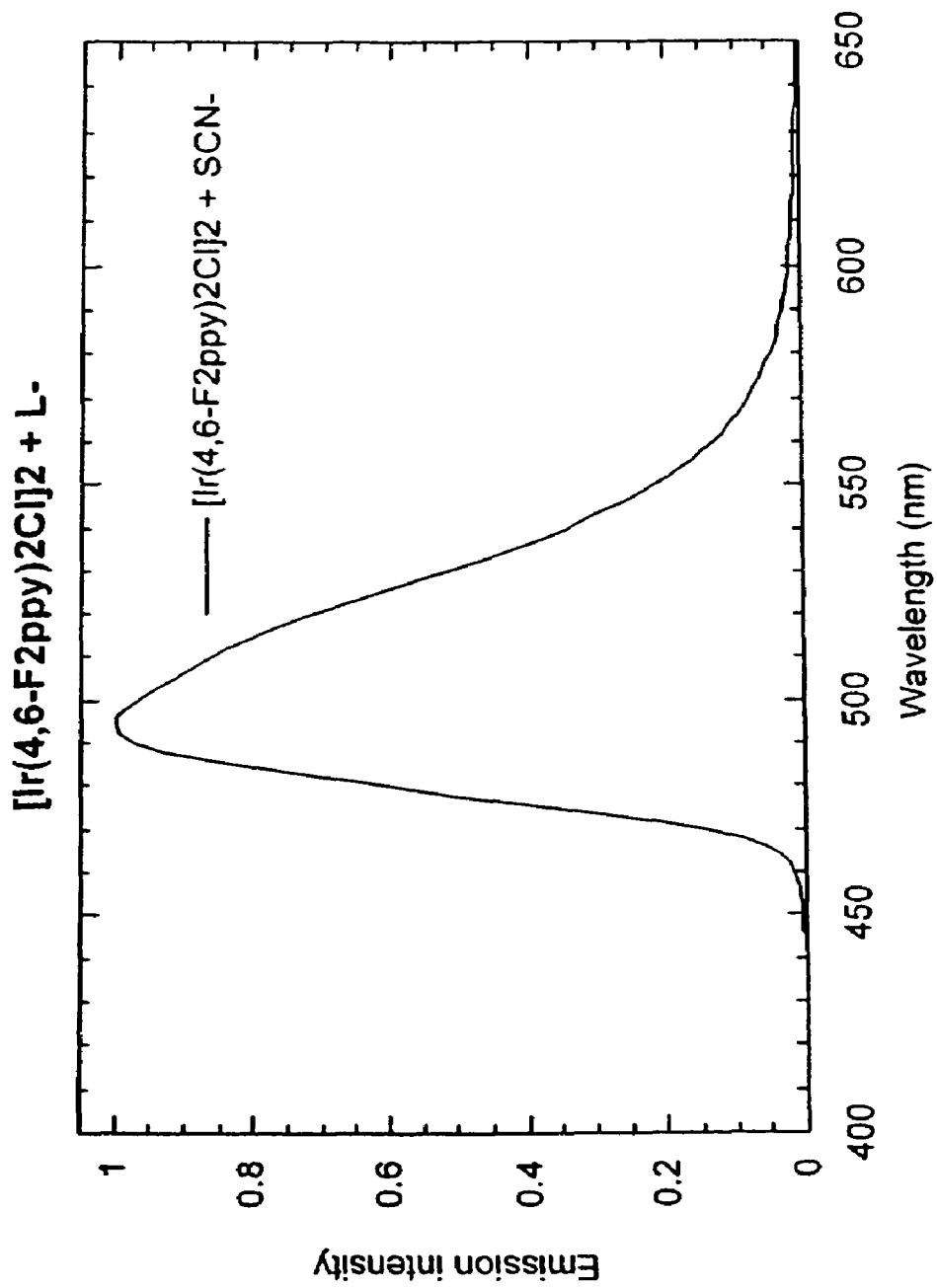
Figure 7L:
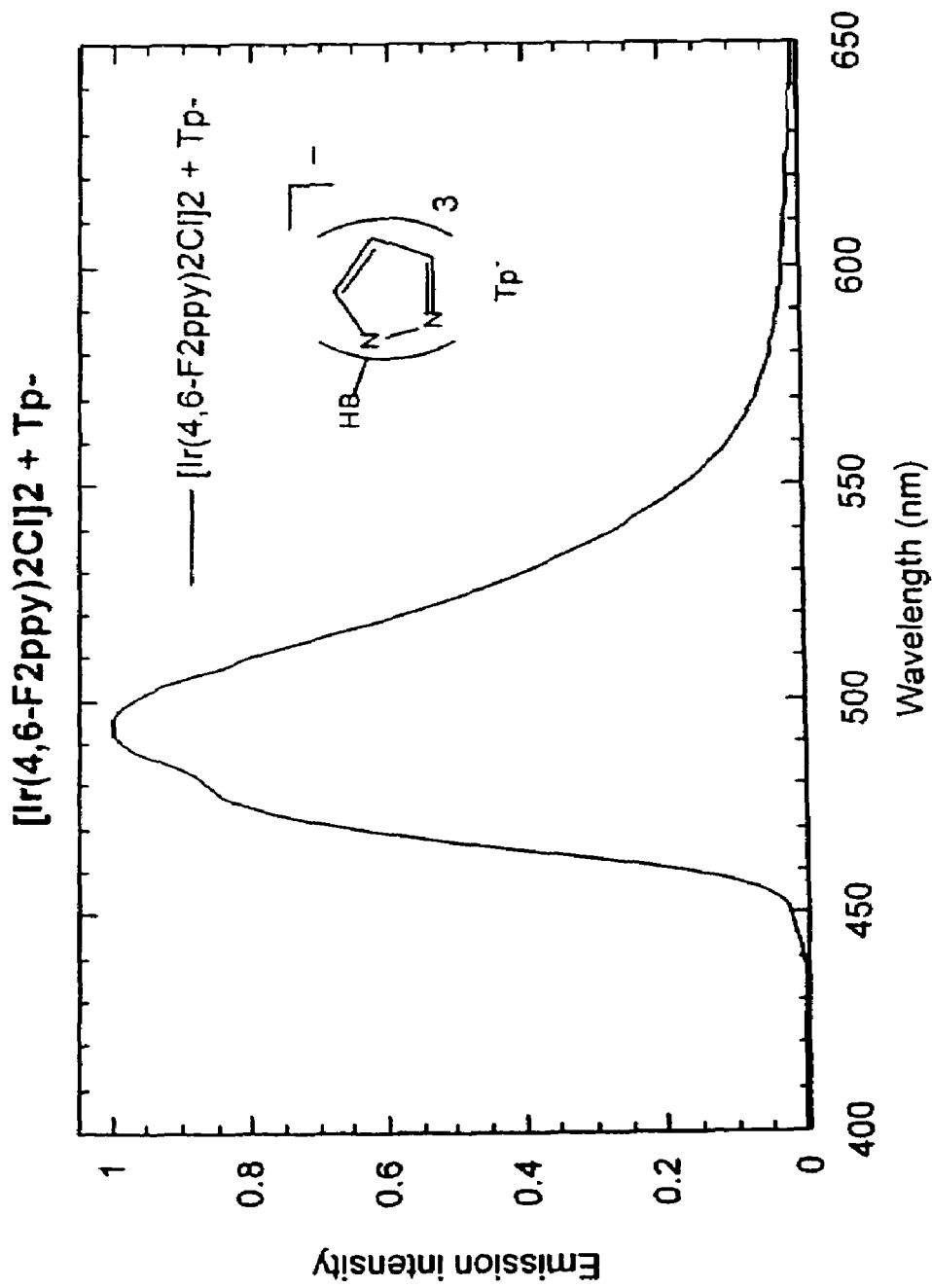
Figure 7M:
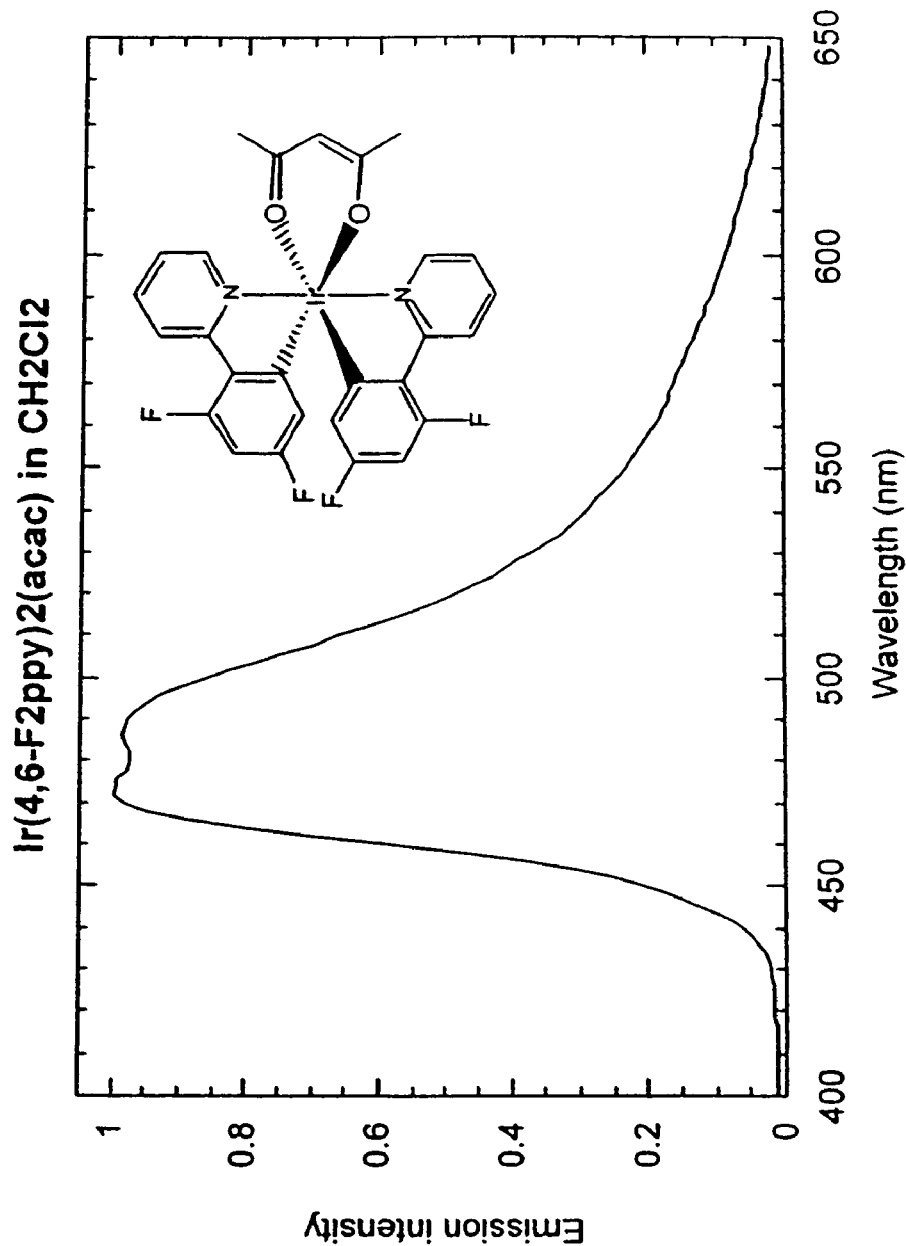
Figure 7N:
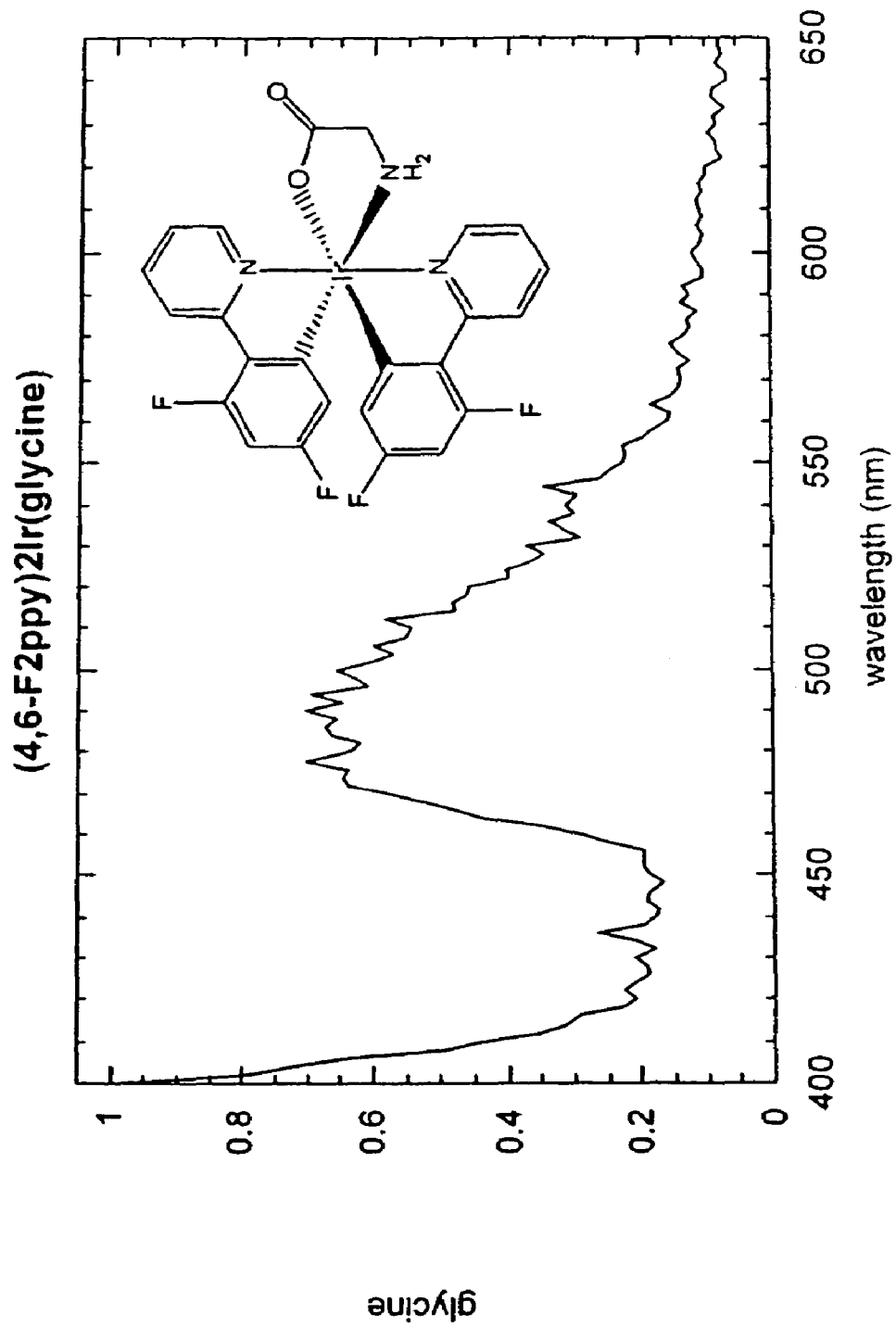
Figure 7O:
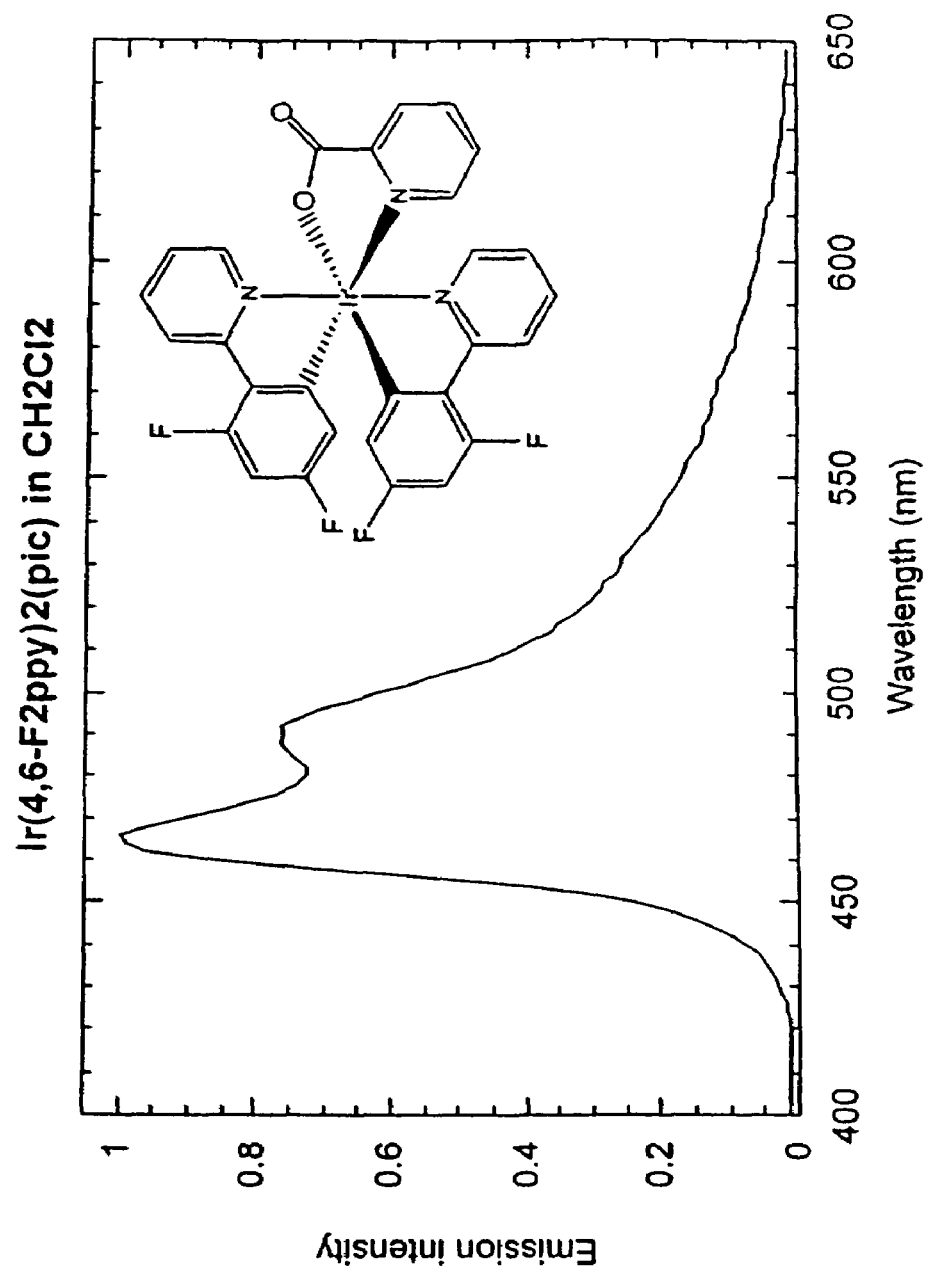
Figure 7P:
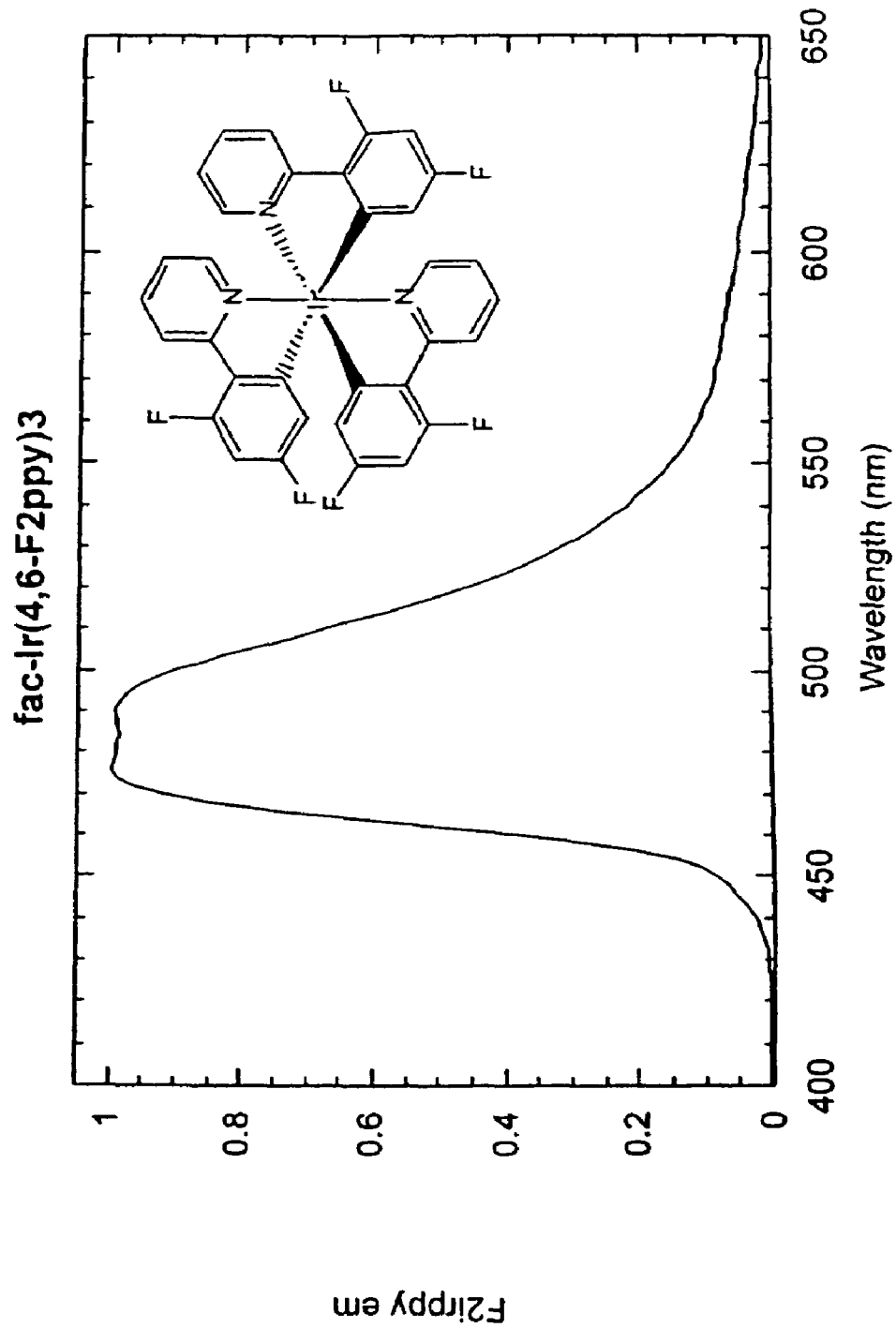
Figure 79:
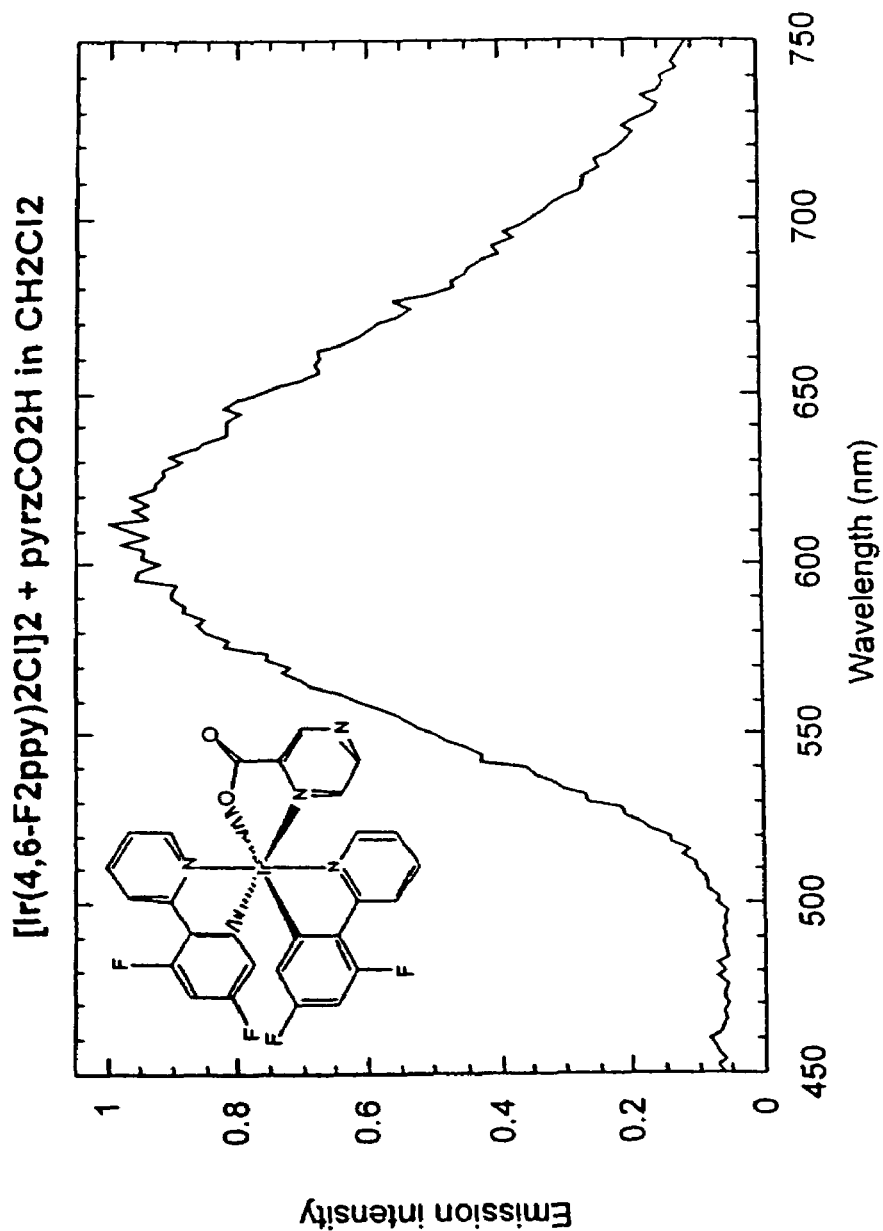
Figure 7R:
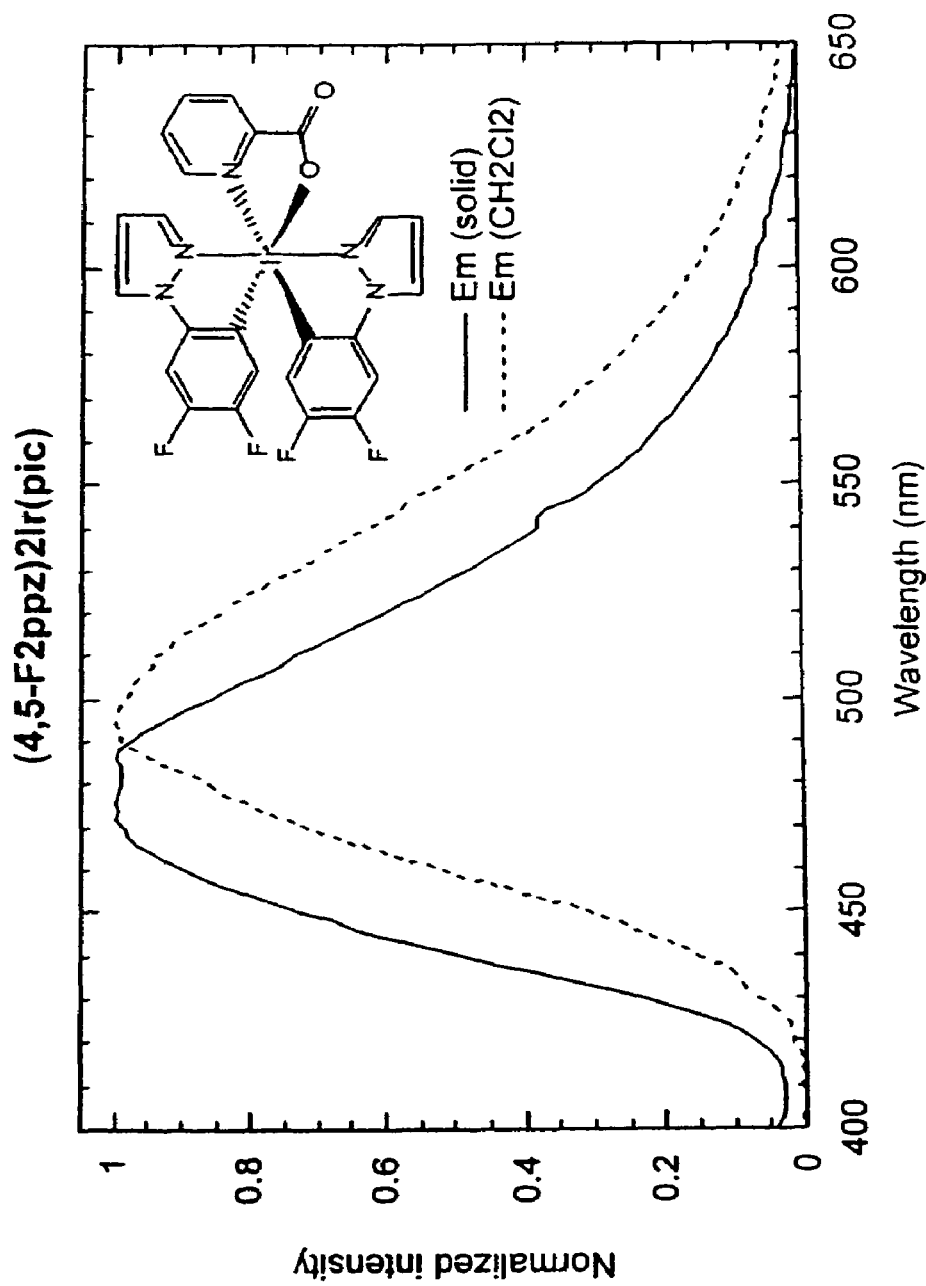
Figure 8B:
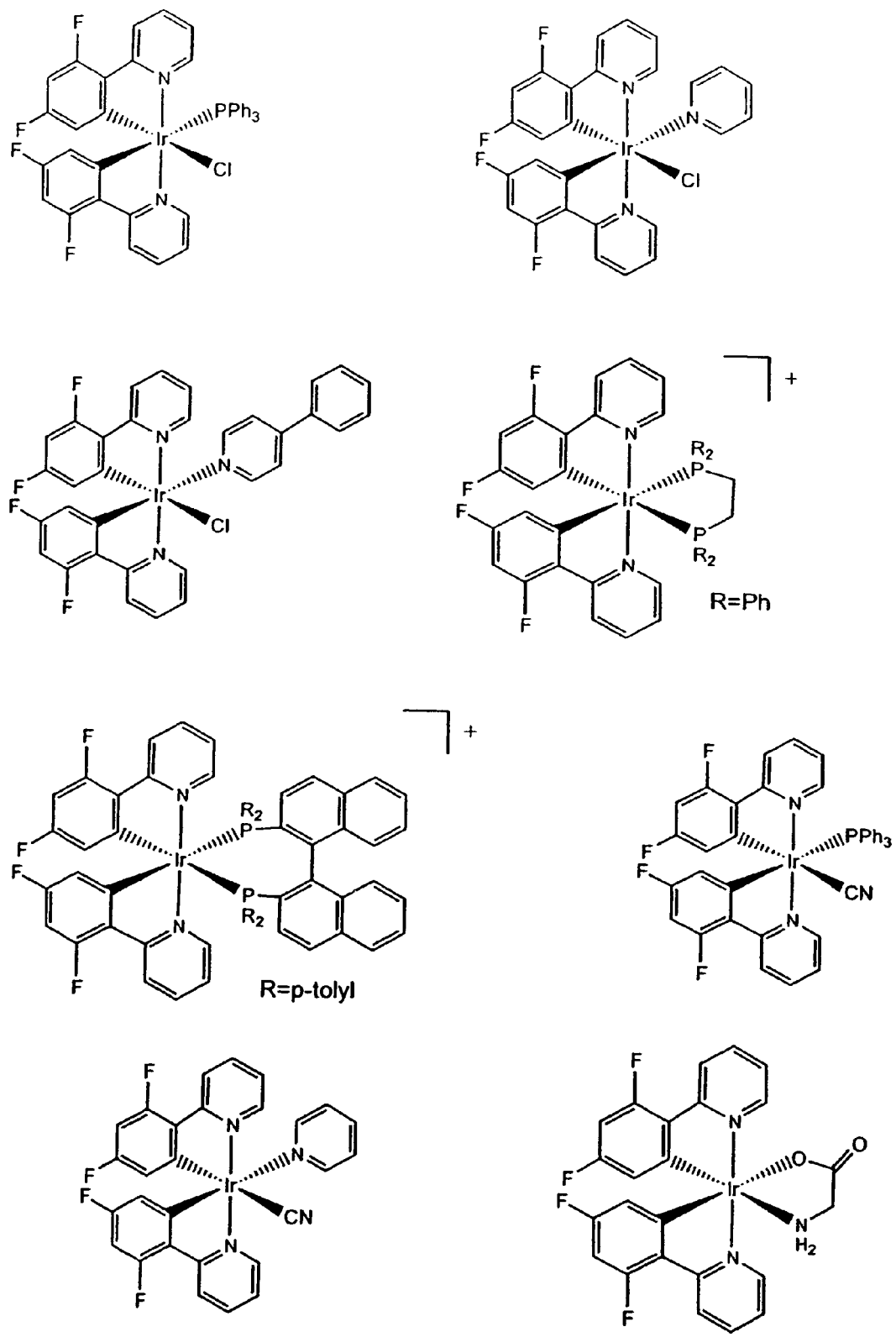
Figure 8C:
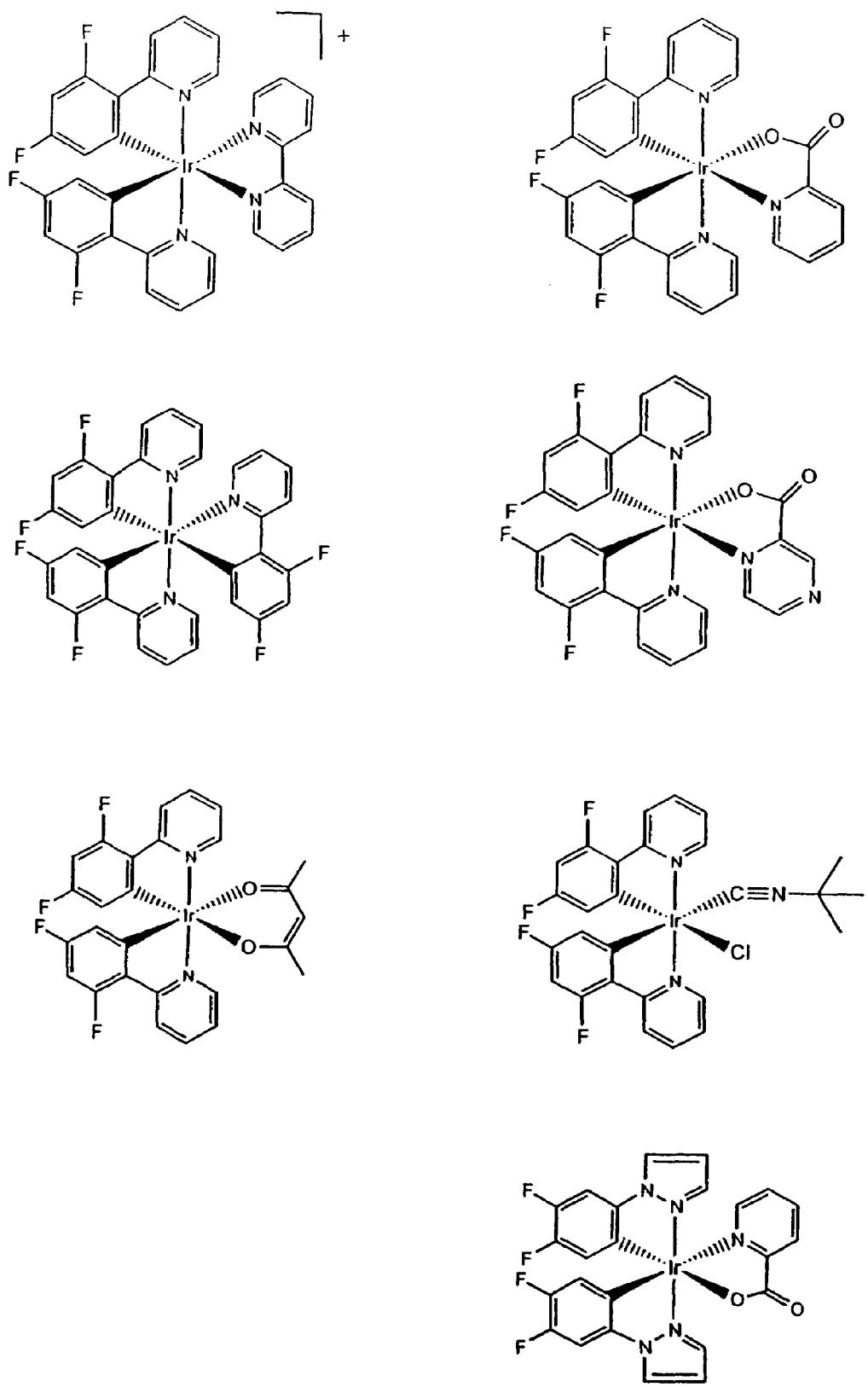

The phosphorescent organometallic compounds of the present invention have at least one mono-anionic, bidentate, carbon-coordination ligand and at least one non-mono-anionic, bidentate, carbon-coordination ligand bound to a heavy transition metal, such as Ir. For example, representative embodiments of the phosphorescent organometallic compounds of the present invention may be illustrated by combining at least one of the mono-anionic, bidentate, carbon-coordination ligands of FIGS. 5a, 5b, 5c and 5d, at least one of the non-mono-anionic, bidentate, carbon-coordination ligands of FIGS. 6a, 6b and 6c, and a heavy transition metal, such as Ir. Representative examples of the phosphorescent organometallic compounds of the present invention, along with their emission spectra, are shown in FIGS. 7a-7r, it being understood that the present invention is not intended to be limited to the representative examples shown.

The preparation of these representative examples of the phosphorescent organometallic compounds of the present invention shown in FIGS. 7a-7r was accomplished as follows.

Synthesis of 2-(4,6-difluorophenyl)pyridine

The 2-(4,6-difluorophenyl)pyridine ligand precursor was prepared by Suzuki coupling of 4,6-difluorophenylboronic acid (Frontier Chemical) with 2-bromopyridine (Aldrich) in 1,2-dimethoxyethane using a Pd(OAc)$_2$/PPh$_3$ catalyst and K$_2$CO$_3$ base as per. Synlett, 1999, 1, 45-48.

Synthesis of fac-tris(2-(4,6-difluorophenyl)pyridi-nato-N,C$^{2'}$) Iridium (III)

The Ir(acac)$_3$ complex was treated with 6 eq of 2-(4,6-difluorophenyl)pyridine in glycerol at 180° C. under inert gas atmosphere for 16 hours. After cooling down to room temperature, water was added to the reaction mixture in order to precipitate the crude product. the solvent was removed under reduced pressure and the crude yellow product was washed with methanol to remove any unreacted picolinic acid. The crude product was flash chromatographed using a silica:dichloromethane column to yield ca. 75% of the pure yellow fac-tris(2-(4,6-difluorophenyl)py-ridinato-N,C$^{2'}$) iridium (III) after solvent evaporation and drying.

Synthesis of [(2-(4,6-difluorophenyl)pyridyl)$_2$IrCl]$_2$

All procedures involving IrCl$_3$.H$_2$O or any other Ir(III) species were carried out in inert gas atmosphere in spite of the air stability of the compounds, the main concern being their oxidative stability and stability of intermediate complexes at high temperatures used in the reactions. The cyclometalated Ir(III) µ-chloro bridged dimer of a general formula C—N$_2$Ir(µ-Cl)$_2$IrC—N$_2$ was synthesized by heating a mixture of IrCl$_3$.nH$_2$O with 4 eq. of 2-(4,6-difluorophenyl) pyridine) in 2-ethoxyethanol at 130° C. for 16 hr. The product was isolated by addition of water followed by filtration and methanol wash. Yield 90%.

Synthesis of Iridium (III) bis(2-(4,6-difluorophenyl) pyridinato-N,C$^{2'}$)(picolinate)

The [(2-(4,6-difluorophenyl)pyridyl)$_2$IrCl]$_2$ complex was treated with 2 eq of picolinic acid in refluxing 1,2-dichloroethane under inert gas atmosphere for 16 hours. After cooling down to room temperature, the solvent was removed under reduced pressure and the crude yellow product was washed with methanol to remove any unreacted picolinic acid. The crude product was flash chromatographed using a silica:dichloromethane column to yield ca. 75% of the pure yellow (C—N)$_2$Ir(pic) after solvent evaporation and drying.

Synthesis of Iridium (III) bis(2-(4,6-difluorophenyl) pyridinato-N,C$^{2'}$)(acetyl acetonate)

The [(2-(4,6-difluorophenyl)pyridyl)$_2$IrCl]$_2$complex was treated with 5 eq of 2,4-pentadione and 10 eq of Na$_2$CO$_3$ in refluxing 1,2-dichloroethane under inert gas atmosphere for 16 hours. After cooling down to room temperature, the solvent was removed under reduced pressure and the crude yellow product was washed with methanol. The crude product was flash chromatographed using a silica:dichloromethane column to yield ca. 75% of the pure yellow (C—N)$_2$Ir(acac) after solvent evaporation and drying.

Synthesis of Iridium (III) bis(2-(4,6-difluorophenyl) pyridinato-N,C$^{2'}$)(tert-butylisocyanide) chloride The [(2-(4,6-difluorophenyl)pyridyl)$_2$IrCl]$_2$complex (ca. 0.002 g) was treated with
an excess of tert-butylisocyanide in 2 mL CH$_2$Cl$_2$ solution for 16 hours.

Synthesis of Iridium (III) bis(2-(4,6-difluorophenyl) pyridinato-N,C$^{2'}$)(triphenylphosphine) chloride The [(2-(4,6-difluorophenyl)pyridyl)$_2$IrCl]$_2$complex (ca. 0.002 g) was treated with an excess of triphenylphosphine in 2 mL CH$_2$Cl$_2$ solution for 16 hours.

Synthesis of Iridium (III) bis(2-(4,6-difluorophenyl) pyridinato-N,C$^{2'}$)(pyridine) chloride The [(2-(4,6-difluorophenyl)pyridyl)$_2$IrCl]$_2$complex (ca. 0.002 g) was treated with
an excess of pyridine in 2 mL CH$_2$Cl$_2$ solution for 16 hours.

Synthesis of Iridium (III) bis(2-(4,6-difluorophenyl) pyridinato-N,C$^{2'}$)(4-phenylpyridine) chloride The [(2-(4,6-difluorophenyl)pyridyl)$_2$IrCl]$_2$complex (ca. 0.002 g) was treated with an excess of 4-phenylpyridine in 2 mL CH$_2$Cl$_2$ solution for 16 hours.

Synthesis of Iridium (III) bis(2-(4,6-difluorophenyl) pyridinato-N,C$^{2'}$)(1,2-bis(diphenylphosphino)ethane) chloride The [(2-(4,6-difluorophenyl)pyridyl)$_2$IrCl]$_2$complex (ca. 0.002 g) was treated with an excess of 1,2-bis(diphenylphosphino)ethane in 2 mL CH$_2$Cl$_2$ solution for 16 hours.

Synthesis of Iridium (III) bis(2-(4,6-difluorophenyl) pyridinato-N,C$^{2'}$)((R)-(+)-2,2'-bis(di-p-tolylphosphino)-1,1'-binaphthyl) chloride The [(2-(4,6-difluorophenyl)pyridyl)$_2$IrCl]$_2$complex (ca. 0.002 g) was treated with an excess of (R)-(+)-2,2'-bis(di-p-tolylphosphino)-1,1'-binaphthyl in 2 mL CH$_2$Cl$_2$ solution for 16 hours.

Synthesis of Iridium (III) bis(2-(4,6-difluorophenyl) pyridinato-N,C$^{2'}$)(2,2'-bipyridine) chloride The [(2-(4,6-difluorophenyl)pyridyl)$_2$IrCl]$_2$complex (ca. 0.002 g) was treated with
an excess of 2,2'-bipyridine in 2 mL CH$_2$Cl$_2$ solution for 16 hours.

Synthesis of Iridium (III) bis(2-(4,6-difluorophenyl) pyridinato-N,C$^{2'}$)(glycine)

The [(2-(4,6-difluorophenyl)pyridyl)$_2$IrCl]$_2$complex (ca. 0.002 g) was treated with an excess of glycine in 2 mL CH$_2$Cl$_2$ solution for 16 hours.

Synthesis of Iridium (III) bis(2-(4,6-difluorophenyl) pyridinato-N,C$^{2'}$)(pyrazinecarboxylate)

The [(2-(4,6-difluorophenyl)pyridyl)$_2$IrCl]$_2$complex (ca. 0.002 g) was treated with an excess of pyrazinecarboxylic acid in 2 mL CH$_2$Cl$_2$ solution for 16 hours.

Synthesis of Iridium (III) bis(2-(4,6-difluorophenyl) pyridinato-N,C$^{2'}$)(tris(pyrazolyl)borate)

The [(2-(4,6-difluorophenyl)pyridyl)$_2$IrCl]$_2$complex (ca. 0.002 g) was treated with an excess of potassium tris(pyrazolyl)borate in 2 mL CH$_2$Cl$_2$ solution for 16 hours.

Synthesis of Iridium (III) bis(2-(4,6-difluorophenyl) pyridinato-N,C$^{2'}$)(cyanide)

The [(2-(4,6-difluorophenyl)pyridyl)$_2$IrCl]$_2$complex (ca. 0.002 g) was treated with an excess of potassium cyanide in 2 mL acetone solution for 16 hours.

Synthesis of Iridium (III) bis(2-(4,6-difluorophenyl) pyridinato-N,C$^{2'}$)(thiocyanide)

The [(2-(4,6-difluorophenyl)pyridyl)$_2$IrCl]$_2$complex (ca. 0.002 g) was treated with an excess of sodium thiocyanide in 2 mL CH$_2$Cl$_2$ solution for 16 hours.

Synthesis of Iridium (III) bis(2-(4,6-difluorophenyl) pyridinato-N,C$^{2'}$)(triphenylphosphine) cyanide The [(2-(4,6-difluorophenyl)pyridyl)$_2$IrCl]$_2$complex (ca. 0.002 g) was treated with an excess of triphenylphosphine and potassium cyanide in 2 mL CH$_2$Cl$_2$ solution for 16 hours.

Synthesis of Iridium (III) bis(2-(4,6-difluorophenyl) pyridinato-N,C$^{2'}$)(pyridine) cyanide The [(2-(4,6-difluorophenyl)pyridyl)$_2$IrCl]$_2$complex (ca. 0.002 g) was treated with an excess of pyridine and potassium cyanide in 2 mL CH$_2$Cl$_2$ solution for 16 hours.

Synthesis of Iridium (III) bis(1-(4,5-difluorophenyl) pyrazolyl-N,C$^{2'}$)(picolinate)

The cyclometalated Ir(III) μ-chloro bridged dimer of a general formula C—N$_2$Ir(μ-Cl)$_2$IrC—N$_2$ was synthesized by heating a mixture of IrCl$_3$.nH$_2$O with 4 eq. of 1-(4,5-difluorophenyl)pyrazole) in 2-ethoxyethanol at 130° C. for 16 hr. The crude product was isolated by addition of water followed by filtration and methanol wash. The crude [(1-(4,5-difluorophenyl)pyrazolyl)$_2$IrCl]$_2$complex was treated with 2 eq of picolinic acid in refluxing 1,2-dichloroethane under inert gas atmosphere for 16 hours. After cooling down to room temperature, the solvent was removed under reduced pressure and the crude yellow product was washed with methanol to remove any unreacted picolinic acid. The crude product was flash chromatographed using a silica:dichloromethane column to yield the pure colorless (C—N)$_2$Ir(pic) after solvent evaporation and drying.

The chemical structures of the phosphorescent organometallic compounds from FIGS. 7a-7r, along with some of the ligands comprising these compounds are also shown in FIGS. 8a-8d.

One example of a representative embodiment of the present invention is Iridium(III)bis(4,6-di-fluorophenyl)-pyridinato-N,C$^{2'}$) picolinate (FIrpic), which was used as a phosphorescent dopant in an OLED to produce efficient blue electrophosphorescence. The synthesis of FIrpic is as follows. The 2-(4,6-difluorophenyl)pyridine ligand precursor was prepared by Suzuki coupling of 4,6-difluorophenylboronic acid (Frontier Chemical) with 2-bromopyridine (Aldrich) in 1,2-dimethoxyethane using a Pd(OAc)$_2$/PPh$_3$ catalyst and K$_2$CO$_3$ base as per Synlett, 1999, 1, 45-48. Next, [(2-(4,6-difluorophenyl)pyridyl)$_2$IrCl]$_2$ was synthesized. All procedures involving IrCl$_3$.nH$_2$O or any other Ir(III) species were carried out in inert gas atmosphere in spite of the air stability of the compounds, the main concern being their oxidative stability and stability of intermediate complexes at high temperatures used in the reactions. Cyclometallated Ir(III) di-chloro bridged dimers of a general formula C—N$_2$Ir(mu-Cl)$_2$IrC—N$_2$ were synthesized by heating a mixture of IrCl$_3$.nH2O (Next Chimica) with 4 eq. of 2-(4, 6-difluorophenyl)pyridine) in 2-ethoxyethanol (Aldrich Sigma) at 130° C. for 16 hr. The product was isolated by addition of water followed by filtration and methanol wash, resulting in a yield of 90%.

The general procedure for synthesizing (C—N)$_2$Ir(pic) complexes is as follows. The [(C—N)$_2$IrCl]$_2$ complex was treated with 2 eq. of picolinic acid (Aldrich Sigma) in refluxing 1,2-dichloroethane under inert gas atmosphere for 16 hours. After cooling down to room temperature, the solvent was removed under reduced pressure and the crude yellow product was washed with methanol to remove any unreacted picolinic acid. The crude product was flash chromatographed using a silica:dichloromethane column to yield ca. 75% of the pure yellow (C—N)$_2$Ir(pic) after solvent evaporation and drying.

In one representative embodiment of the present invention, we demonstrate blue electrophosphorescence using energy transfer from a conductive organic host to an iridium complex with two 2-(4,6-difluoro-phenyl)pyridine as two mono-anionic, bidentate, carbon-coordination ligands (cyclometallated) and a picolinate ligand as a non-mono-anionic, bidentate, carbon-coordination ligand. See Lamansky, S., Djurovich, P., Murphy, D., Abdel-Razzaq, F., Adachi, C., Burrows, P. E., Forrest, S. R., and Thompson, M. E., J. Am. Chem. Soc., (in press). The introduction of fluorine groups, which are electron withdrawing substituents, results in an increase of the triplet exciton energy and hence a blue shift of the phosphorescence compared with that of Ir(ppy)$_3$. Using Iridium(III)bis(4,6-di-fluorophenyl)-pyridinato-N, C$^{2'}$) picolinate (FIrpic), we obtained a maximum external quantum EL efficiency ($\eta_{ext}$) of (5.7±0.3) % and a luminous power efficiency ($\eta_p$) of (6.3±0.3)lm/W. To our knowledge, this is the first report of efficient blue electrophosphorescence (see Adachi, C., Baldo, M. A., Thompson, M. E., and Forrest, S. R., Material Research Society, Fall Meeting Boston, Mass., 1999; Wu, Q. G., Lavigne, J. A., Tao, Y., D'Iorio, M., and Wang, S. N., Inorg. Chem., 39, 5248-5254 (2000); and Ma, Y. G., Lai, T. S., and Wu, Y, Adv. Mat., 12, 433-435 (2000)) and represents a significant improvement of the efficiencies compared with the best blue fluorescent emitters reported to date. See Grice, A. W., Bradley, D. D. C., Bernius, M. T., Inbasekaran, M., Wu, W. W., and Woo, E. P., Appl. Phys. Lett., 73, 629-931 (1998); Hosokawa, C., Higashi, H., Nakamura, H., and Kusumoto, T., Appl. Phys. Lett., 67, 3853-3855 (1995); and Hosokawa, C., Eida, M., Matsuura, M., Fukuoka, K., Nakamura, H., and Kusumoto, T., Synth. Met., 91, 3-7 (1997).

FIG. 1$a$ shows photoluminescent (PL) spectra in a dilute (10$^{-5}$M) chloroform solution of three different iridium-based phosphors, bis(2-phenylpyridinato-N,C$^{2'}$)iridium (acetylacetonate) [ppy$_2$Ir(acac)] (curve c), bis(4,6-di-fluorophenyl)-pyridinato-N,C$^{2'}$)iridium(acetylacetonate) [FIr(acac)] (curve b), and FIrpic (curve a), demonstrating a spectral shift with ligand modification. FIG. 1$a$ also shows the molecular structures of these iridium complexes: FIrpic (structure a), FIr(acac) (structure b), and ppy$_2$Ir(acac) (structure c). The presence of the heavy metal iridium results in strong spin-orbit coupling and metal ligand charge transfer, allowing for rapid intersystem crossing of excitons into the radiative triplet manifold. See King, K. A., Spellane, P. J. and Watts, R. J., J. Am. Chem. Soc., 107, 1431-1432 (1985); and Lamansky, S.; Djurovich, P.; Murphy, D.; Abdel-Razzaq, F.; Kwong, R.; Tsyba, L; Bortz, M.; Mui, B.; Bau, R.; Mark E. Thompson, M. E. Inorganic Chemistry, 40, 1704-1711 (2001). All three of these complexes give high photoluminescent efficiencies of $\Phi_{pl}$=0.5-0.6 in fluid solution. With the introduction of electron withdrawing fluorine atoms into the 4,6-positions of 2-phenylpyridine, the triplet excited state experiences a blue shift of ~40 nm in the PL peak of FIr(acac), as compared with the green emitting ppy$_2$Ir(acac). Furthermore, replacement of the acetylacetonate ligand (acac) of FIr(acac) with picolinate (i.e., FIrpic) resulted in an additional ~20 nm blue shift.

Organic light emitting devices (OLEDs) were grown on a glass substrate precoated with a ~130 nm thick indium-tin-oxide (ITO) layer with a sheet resistance of ~20 Ω/□. Prior to organic layer deposition, the substrate was degreased with solvents and cleaned for 5 min by exposure to a UV-ozone ambient, after which it was immediately loaded into the evaporation system. With a base pressure of ~4×10$^{-8}$ Torr, the organic and metal cathode layers were grown successively without breaking vacuum using an in vacuuo mask exchange mechanism. First, a 10 nm-thick copper phthalocyanine (CuPc) hole injection layer followed by a 30 nm-thick 4,4'-bis[N-(1-naphthyl)-N-phenyl-amino]biphenyl (α-NPD) hole transport layer (HTL), respectively, were deposited. Next, a 30 nm-thick light-emitting layer (EML) consisting of 6%-FIrpic doped into a 4,4'-N,N'-dicarbazole-biphenyl (CBP) host was prepared via thermal co-deposition. Finally, a 30 nm-thick layer of aluminum(III)bis(2-methyl-8-quinolinato)4-phenylphenolate (BAlq) was used to transport and inject electrons into the EML. A shadow mask with rectangular 2 mm×2 mm openings was used to define the cathode consisting of a 1 nm-thick LiF layer, followed by a 100 nm-thick Al layer. After deposition, the device was encapsulated using a UV-epoxy resin under a nitrogen atmosphere with <1 ppm oxygen and water. We found that carrying out the entire layer deposition process under high vacuum is crucial for obtaining high efficiencies. Given that the peak CBP triplet wavelength (see Baldo, M. A., and Forrest, S. R., Phys. Rev. B 62, 10958-10966 (2000)) is λ=484 nm [(2.56±0.10) eV], compared to λ=475 nm [(2.62±0.10) eV] for FIrpic (see spectra in FIG. 3), the endothermic transfer process may be easily interrupted by the presence of nonradiative defect states of intermediate energy. Introduction of oxygen or water may be the source of such defects. Indeed, we have found that breaking vacuum at any point in the fabrication process and exposure to air or purified nitrogen (<1 ppm oxygen and water) results in a decrease in efficiency of at least a factor of two below the values reported here. A similar ambient sensitivity is not observed for green and red electrophosphorescence OLEDs employing conventional exothermic energy transfer mechanisms.

FIG. 1$b$ shows the electroluminescence spectra of the following OLED structure: ITO/CuPc (10 nm)/α-NPD (30 nm)/CBP host doped with 6% FIrpic (30 nm)/BAlq (30 nm)/LiF (1 nm)/Al (100 nm). The EL spectrum has a maximum at the peak wavelength of $\lambda_{max}$=475 nm and additional sub-peaks at $\lambda_{sub}$=495 nm and 540 nm (arrows) which generally agrees with the PL spectral shape. The Commission Internationale de L'Eclairage (CIE) coordinates of (x=0.16, y=0.29) for a FIrpic OLED are shown in the inset of FIG. 1b along with the coordinates of green (Ir(ppy)$_3$)(x=0.28, y=0.62) and red (Btp$_2$Ir(acac))(x=0.67, y=0.33) electrophosphorescence devices. Further tuning of the color purity in the blue through the molecular design of ligands still needs to occur to achieve a closer match to the National Television Standards Committee (NTSC) recommended blue for a video display (lower vertex in the inset).

FIG. 2 shows external electroluminescent quantum ($\eta_{ext}$: filled squares) and power ($\eta_p$: open circles) efficiencies as functions of current density for the following OLED structure: ITO/CuPc (10 nm)/α-NPD(30 nm)/CBP host doped with 6% FIrpic (30 nm)/BAlq (30 nm)/LiF (1 nm)/Al (100 nm). A maximum $\eta_{ext}$=(5.7±0.3) % (corresponding to an internal efficiency of ~30%) and a luminous power efficiency ($\eta_p$) of (6.3±0.3)lm/W are achieved at J=0.5 mA/cm$^2$ and 0.1 mA/cm$^2$, respectively. While the device shows a gradual decrease in $\eta_{ext}$ with increasing current which has previously been attributed to triplet-triplet annihilation (see Adachi, C., Baldo, M. A., and Forrest, S. R., J. Appl. Phys., 87, 8049-8055 (2000); Baldo, M. A., Adachi, C., and Forrest, S. R., Phys. Rev. B 62, 10967-10977 (2000); and Adachi, C., Kwong, R. C., and Forrest, S. R., Organic Electronics, 2, (2001) (in press)), a maximum luminance of 6400 cd/m$^2$ with $\eta_{ext}$=3.0% was obtained even at a high current of J=100 mA/cm$^2$. These values compare favorably with $\eta_{ext}$=2.4% for fluorescent devices with a similar blue color emission spectrum. See Hosokawa, C., Higashi, H., Nakamura, H., and Kusumoto, T., Appl. Phys. Lett., 67, 3853-3855 (1995). The inset to FIG. 2 shows an energy level diagram of triplet levels of a CBP host and a FIrpic guest. Due to the energy lineup of CBP and FIrpic triplet levels, both exothermic and endothermic transfer can be possible. Here, $\kappa_g$ and $\kappa_h$ are the radiative decay rates of triplets on the guest (phosphor) and host molecules, and the rates of exothermic (forward) ($\kappa_F$) and endothermic (reverse) ($\kappa_R$) energy transfers between CBP and FIrpic is also indicated. Since the triplet energy level of a CBP host (2.56±0.10) eV is slightly less than that of FIrpic at (2.62±0.10) eV (inset of FIG. 2), exothermic energy transfer from FIrpic to CBP is inferred. Note that the pronounced roll-off at small J is uncharacteristic of conventional electrophosphorescence. This is indicative of the sensitivity of backward energy transfer to the presence of energy dissipative pathways, reducing the efficiency via nonradiative triplet recombination when the density of triplets is too low to saturate these parasitic mechanisms. In addition, unbalanced hole and electron injection into EML can also account for the roll off.

FIG. 3 shows a streak image of the transient decay of a 6%-FIrpic:CBP film (100 nm thick) on a Si substrate under nitrogen pulse excitation (~500 ps) at T=100 K. Two distinct decay processes, prompt and delayed phosphorescence, are demonstrated along with their photoluminescent spectra: dashed line=prompt and solid line=delayed. Also shown is the CBP phosphorescence spectrum obtained at 10 K. In addition to the prompt phosphorescence of FIrpic, we observe an extremely long decay component lasting for τ~10 ms which follows the CBP triplet lifetime. The prompt phosphorescence has a lifetime somewhat shorter than the solution phosphorescence lifetime of FIrpic (2 μsec). Since the PL spectrum of the slow component coincides with that of FIrpic PL, this supports the conclusion that exothermic energy transfer from FIrpic to CBP occurs. The triplet state then migrates through the CBP host molecules and finally is endothermally transferred back to FIrpic, resulting in the delayed phosphorescence observed. Due to the significant difference of lifetimes of the excited states, $\kappa_h<<\kappa_g$, ($\kappa_h$ and $\kappa_g$ are the radiative decay rates of the triplets on the host and guest molecules, respectively), the triplet exciton decay originates from FIrpic, as desired. Here, the low intensity blue emission centered at $\lambda_{max}$=400 nm in the prompt emission spectrum is due to fluorescence of CBP, with a transient lifetime <<100 ns which is significantly shorter than the transient decay of FIrpic. A similar process has been observed for energy transfer from the pyrene triplet to a Ru MLCT excited state, leading to long Ru-MLCT excited state lifetimes. See Ford, W. E., Rodgers, M. A. J., J. Phys. Chem., 96, 2917-2920 (1992); Harriman, A.; Hissler, M.; Khatyr, A.; Ziessel, R. Chem. Commun., 735-736 (1999).

FIG. 4 shows the transient photoluminescence decay characteristics of a 100 nm thick 6%-FIrpic:CBP film on a Si substrate under nitrogen pulse excitation (~500 ps) at T=50 K, 100 K, 200 K and 300 K. The inset to FIG. 4 shows the temperature dependence of the relative photoluminescence (PL) efficiency ($\eta_{PL}$) of FIrpic doped into CBP. After a slight enhancement of $\eta_{PL}$ as temperature is increased from 50 K to 200 K, it once again decreases at yet higher temperatures. The transient decay characteristics are also temperature dependent. In particular, a significant decrease in the nonexponential decay time was observed at T=50 K and 100 K. The enhancement of $\eta_{PL}$ from T=300 K to 200 K is due to the suppression of nonradiative decay of FIrpic. The decrease of $\eta_{PL}$ below T~200 K, however, is a signature of retardation of the endothermic process of energy transfer from CBP to FIrpic, leading to loss of the radiative triplet excitons. Since we observe no delayed component at T=300 K, energy transfer from CBP to FIrpic is very efficient with thermal assistance. In contrast, the PL intensity of Ir(ppy)$_3$: CBP shows no temperature dependence along with no evidence for such a slow component at low temperature, suggesting the absence of backward energy transfer in that low triplet energy guest system.

As discussed above, we have herein demonstrated efficient blue electrophosphorescence using FIrpic as the phosphor molecule. Due to the comparable energy of the phosphor triplet state relative to that of the 4,4'-N,N'-dicarbazole-biphenyl (CBP) conductive host molecule into which it is doped, the exothermic transfer of energy from phosphor to host, and subsequent endothermic transfer from host back to phosphor is clearly observed. Using this triplet energy transfer process, we force emission from the higher energy, blue triplet state of the phosphor. The existence of endothermic energy transfer is confirmed by the low temperature phosphorescent spectra of CBP and FIrpic, and the appearance of a maximum in the photoluminescent intensity of CBP:FIrpic at T~200 K. Employing this process, a very high maximum external quantum efficiency of (5.7±0.3) % and a luminous power efficiency of (6.3±0.3)lm/W are achieved. The electroluminescent (EL) spectrum has a maximum at a wavelength of $\lambda_{max}$=470 nm with additional peaks at $\lambda_{sub}$=495 nm and 540 nm, leading to the Commission Internationale de L'Eclairage (CIE) coordinates of x=0.16 and y=0.29.

Other representative embodiments of the organometallic compounds of the present invention are aimed at a new class of platinum complexes, which give efficient phosphorescence. The representative complexes have a single organometallic ligand (cyclometallated) and a bidentate coordination ligand (such as acetylacetonate). Several examples of these complexes are given below along with their spectra. The emission spectra from these complexes show vibronic fine structure, consistent with strong ligand π-π* character in the phosphorescent transition. Strong ligand π-π* character is also consistent with the fact that the emission energy is strongly dependent on the identity of the ligand, as shown in the spectra shown below. Emission from these complexes results from a mixture of metal to ligand charge transfer (MLCT) and ligand based transitions. The MLCT is critical to enhance the efficiency of intersystem crossing and phosphorescence. The emission is dominated by the cyclometallated ligand and the MLCT between the Pt ion and that ligand. The emission spectrum is only slightly affected by changing the acetylacetonate ligand (acac) to a picolinic acid (pico), as shown for the (ppy)PtX complexes below. This minor shift most likely occurs due to a shift in the Pt based HOMO level by the pico ligand, leading to a red shift in the MLCT and a corresponding red shift in the emission spectrum.

One of these complexes, i.e. (2-(4,5-$F_2$-phenyl)pyridinato)Pt(acetylacetonate), was used as a phosphorescent dopant in a polymer OLED and gave an emission spectrum identical to the photoluminescence spectrum and an external quantum efficiency of 1.3%.

(ppy)Pt(acac)

(tpy)Pt(acac)

(bzq)Pt(acac)

(4,6-$F_2$ppy)Pt(acac)

(btp)Pt(acac)

-continued (4,5-$F_2$ppy)Pt(acac)

(4,5-$F_2$ppy)Pt(pico)

As representative electrophosphorescent compounds of the present invention, the carbon-coordination ligand forms a cyclometallated ring that includes the organometallic carbon-metal bond and a dative bond between the metal atom and a nitrogen, sulfur or oxygen group, for example, Pt(II)-(2-phenylpyridinato-N,$C^{2'}$)(acetyl acetonate), herein referred to as Pt(ppy)(acac) or (ppy)Pt(acac). The carbon atom that is bound to the metal may be present as part of a substituted or unsubstituted, saturated hydrocarbon; a substituted or unsubstituted, aromatic system, for example, phenylene or naphthalene compounds; or a substituted or unsubstituted heterocyclic system, which might include, for example, substituted or unsubstituted thiophenes, furans, pyridines and pyrroles. The group in the cyclometallated ring that forms a dative bond with the metal atom may be independently selected also to include a substituted or unsubstituted, saturated hydrocarbon; a substituted or unsubstituted, aromatic system, for example, phenylene or naphthalene compounds; or a substituted or unsubstituted heterocyclic system, which might include, for example, thiophenes, furans, pyridines and pyrroles.

The preparation of these representative compounds of the present invention was accomplished as follows. All procedures involving $K_2PtCl_4$ or any other Pt species were carried out in inert gas atmosphere in spite of the air stability of the compounds, the main concern being their oxidative stability and stability of intermediate complexes at high temperatures used in the reactions. NMR spectra were recorded on Bruker AMX 360 MHz or 500 MHz instruments unless specified otherwise. Solid probe MS spectra were taken with Hewlett Packard GC/MS instrument with electron impact ionization and model 5873 mass sensitive detector. High resolution mass spectrometry was done at Frik Chem Laboratories at Princeton University. Elemental analysis data was recorded at the Microanalysis Laboratory at the University of Illinois, Urbana-Champaine.

Pt(II) μ-chlorobridged dimers of the structure [Pt(C—N)(μ-Cl)$_2$Pt(C—N)] containing cyclometalated carbon, nitrogen ligands (C,N) used in the study were prepared according to Cave G. W. V., Fanizzi F. P., Deeth R. J., Errington W., Rourke J. P., Organometallics 2000, 19, 1355.

Figures 9A, 9B, 9C, 9D, 9E, 9F, 9G:
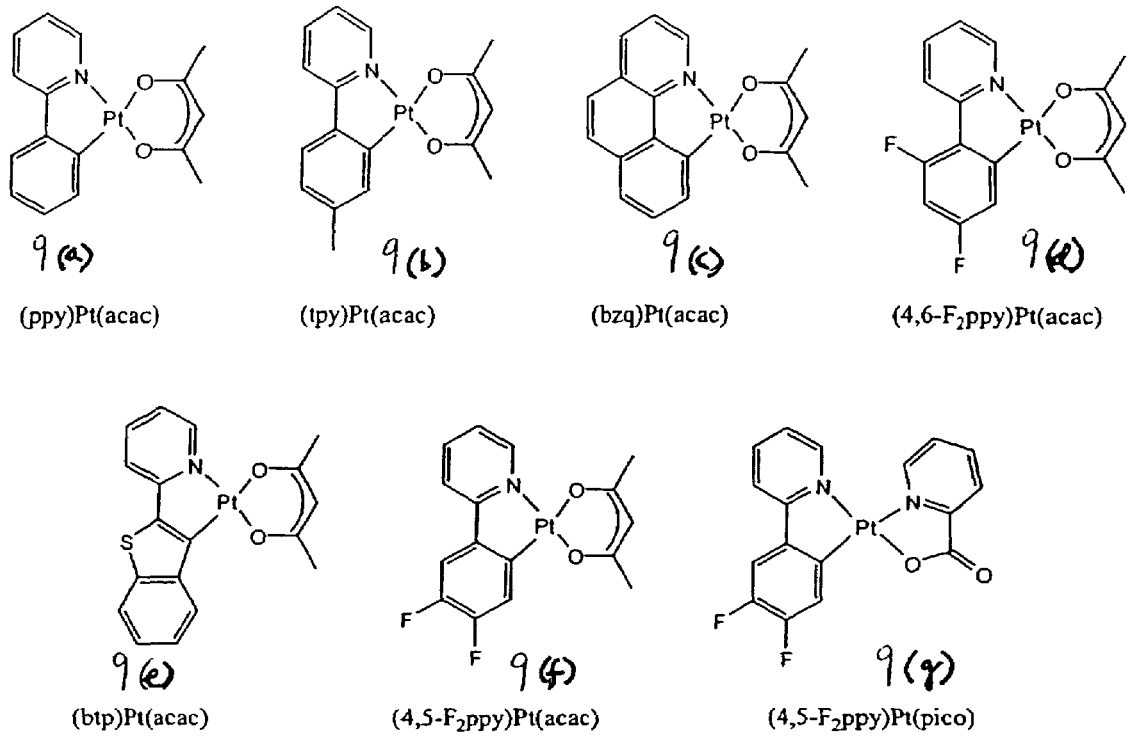
FIGS. 9*a* through 9*g* show the chemical structures of representative organometallic compounds described herein.
Figure 10:
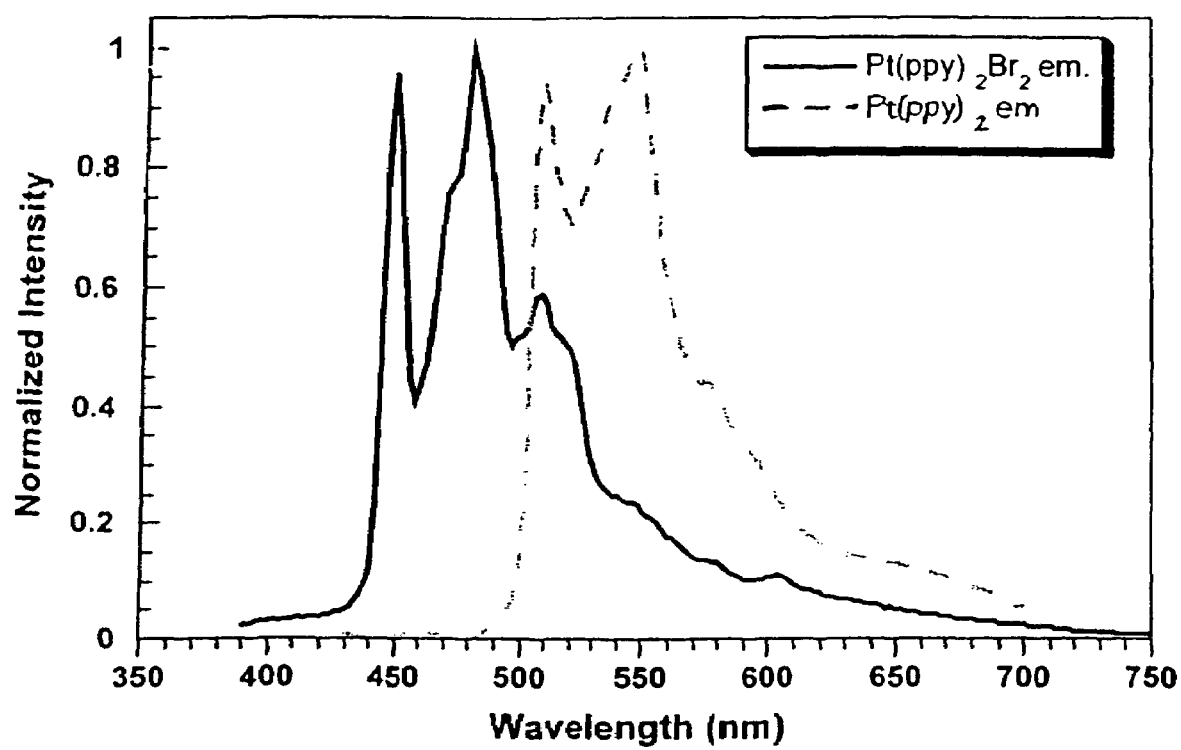
FIG. 10 shows the emission spectrum of both Pt(Ppy)$_2$ and Pt(ppy)$_2$Br$_2$. The former gives green emission, partly from MLCT transitions, and the latter gives blue emission, predominantly from a triplet π-π* transition. The structure observed for the Pt(Ppy)$_2$Br$_2$ spectrum is consistent with ligand-centered emission. The luminescent lifetimes for the two complexes are 4 and 150 microseconds.
Figure 11:
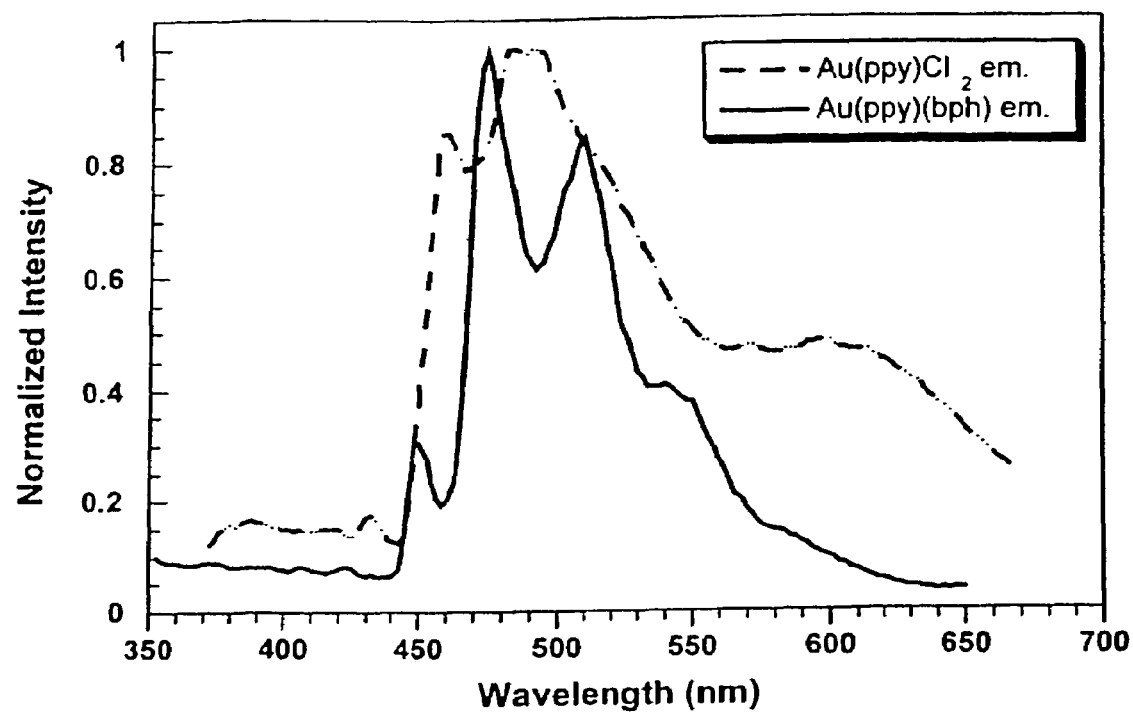
FIG. 11 is a plot showing the emission spectra of (ppy)AuCl$_2$ and (ppy)Au(2,2'biphenylene). Both emit from ligand triplet π-π* transitions.
Figure 12:
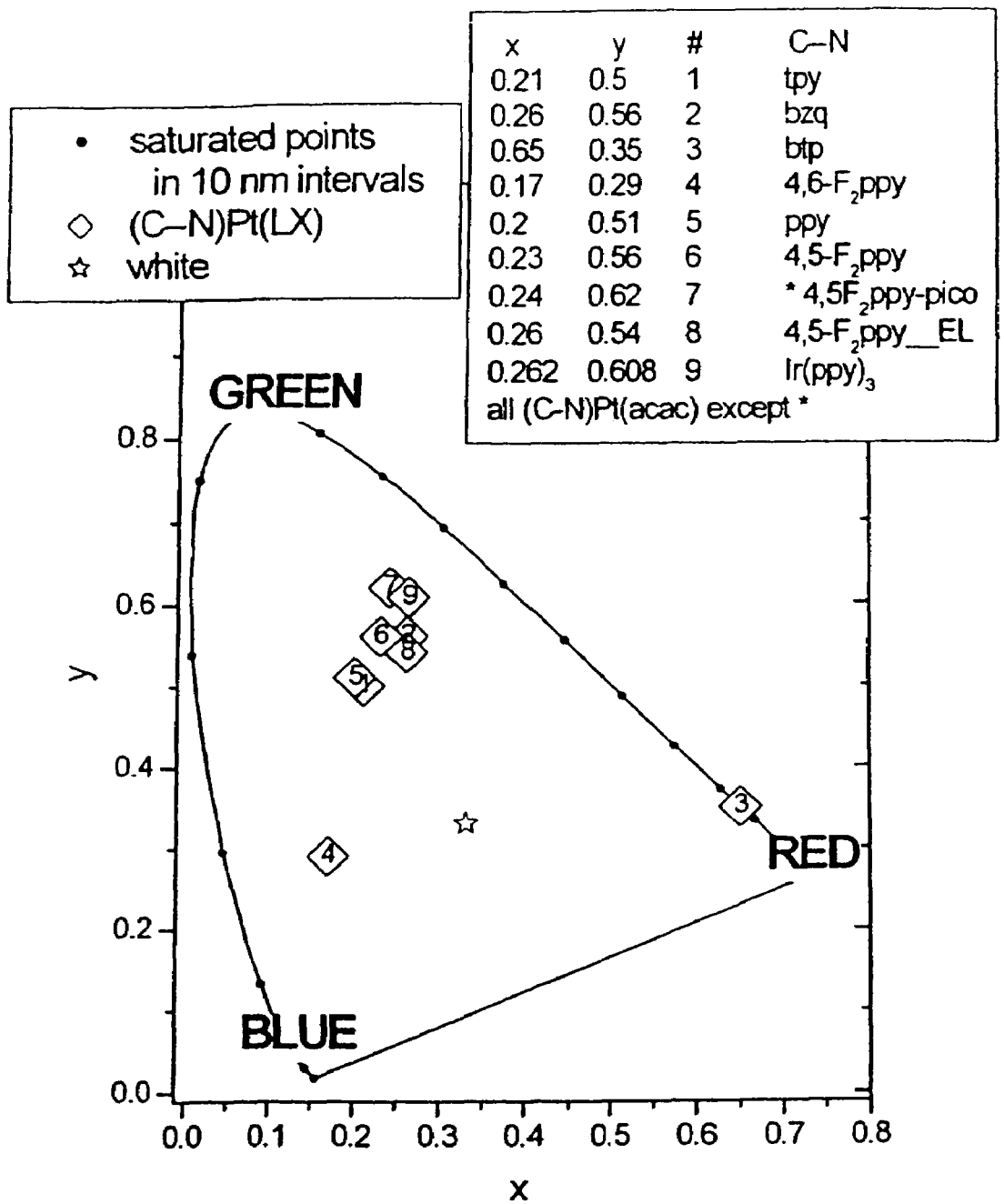
FIG. 12 is a CIE diagram providing the coordinates of (C—N)Pt(acac) complexes. All coordinates are based on solution photoluminescent measurements except for 4,5-F$_2$ppy-EL, which corresponds to the electroluminescent spectrum. The Ir(ppy)$_3$ is an electroluminescent spectrum as well.
Figure 13:
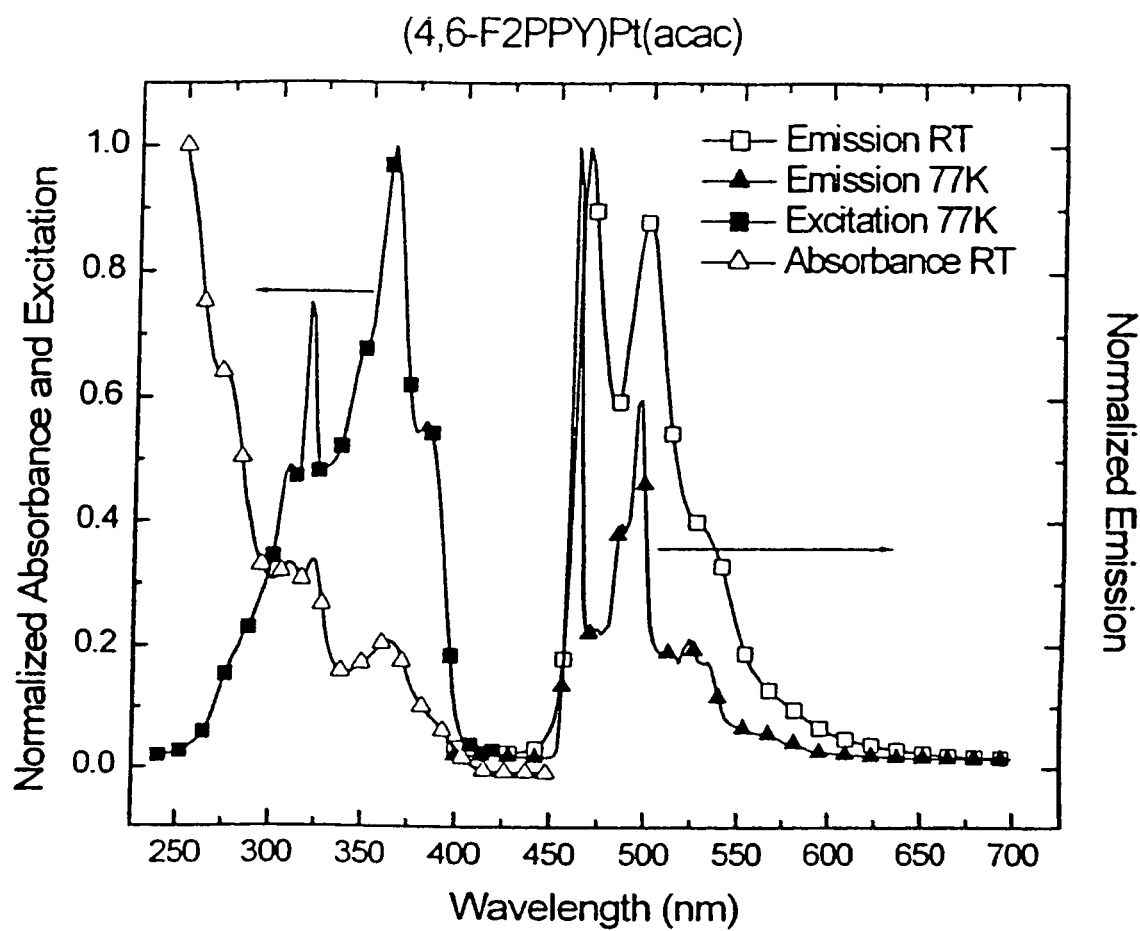
FIG. 13 is a plot depicting the photoluminescent emission spectra of (4,6-F$_2$ppy)Pt(acac) at room temperature (RT) and at 77 K. Also shown are the excitation spectra taken at 77 K and the absorbance spectra taken at room temperature for the same complex.
Figure 14:
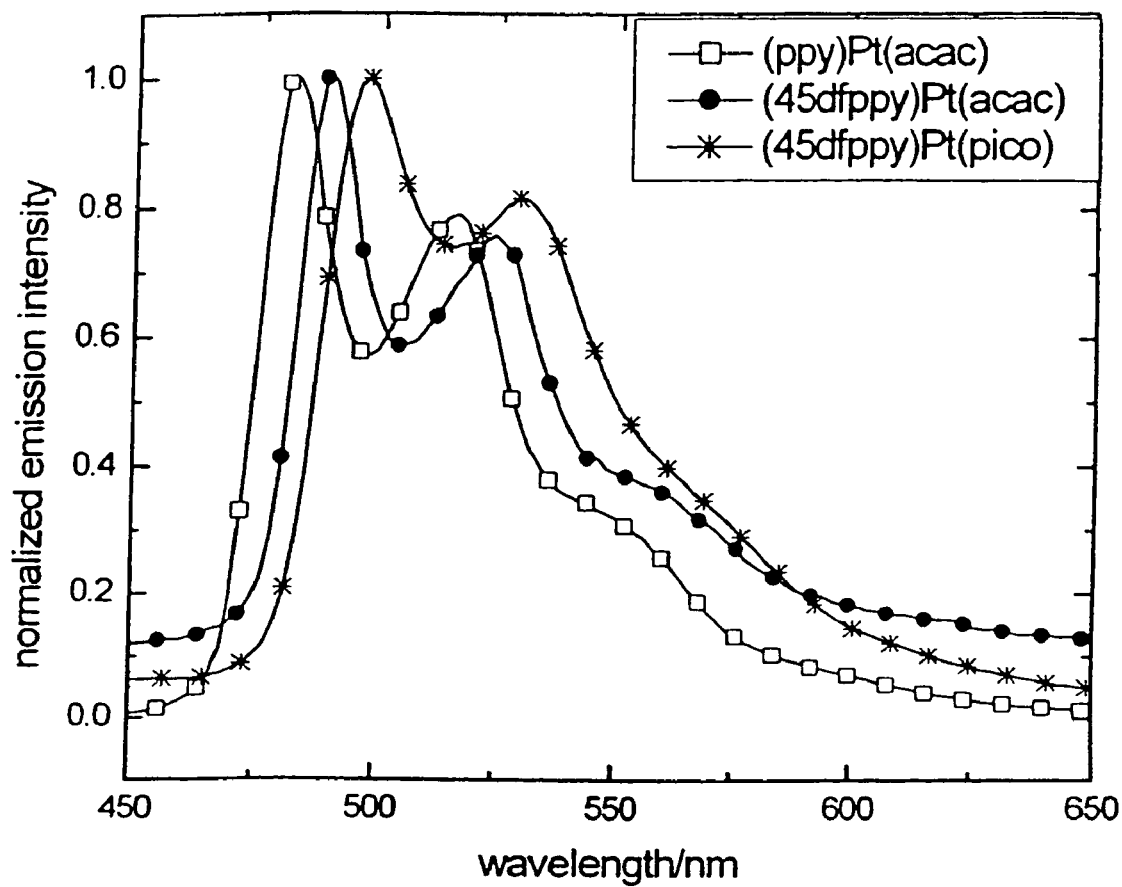
FIG. 14 illustrates the normalized photoluminescent emission spectra of (ppy)Pt(acac), (4,5 dfppy)Pt(acac), and (4,5 dfppy)Pt(pico).
Figure 15:
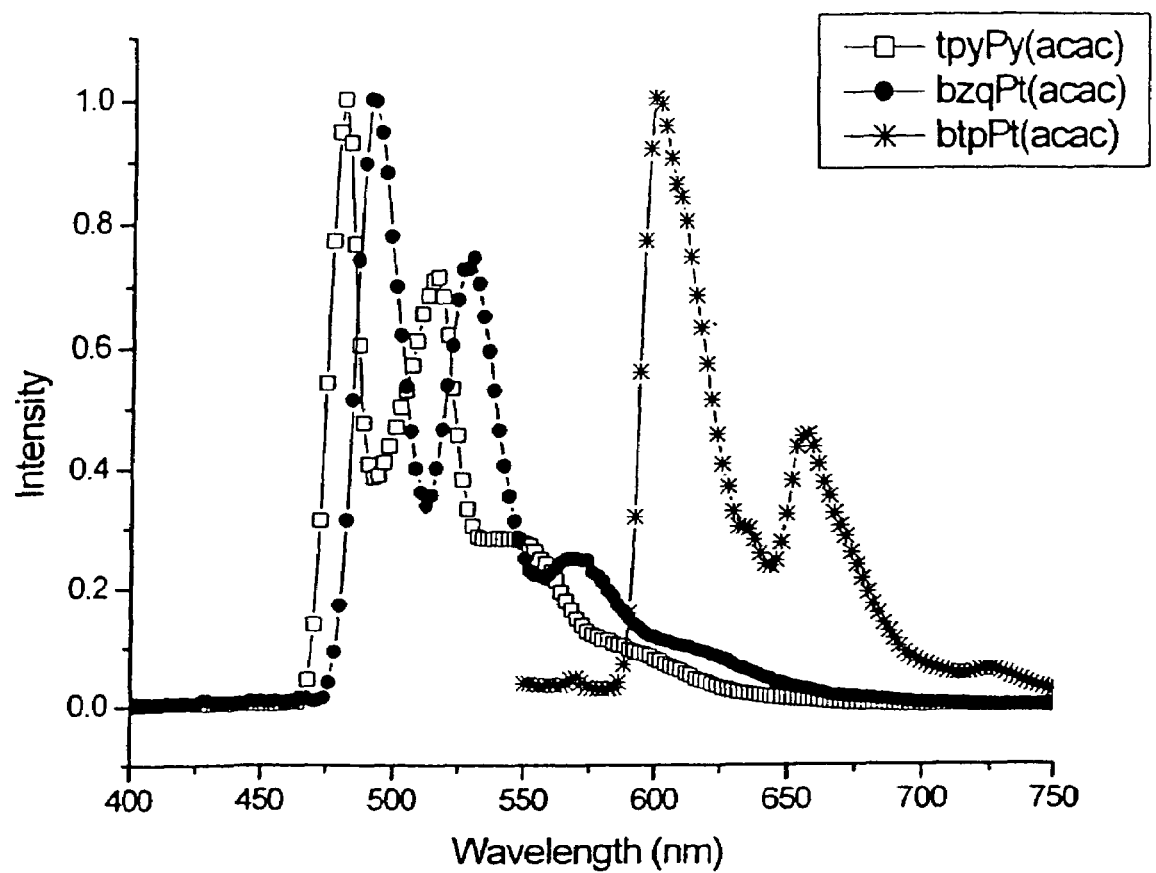
FIG. 15 illustrates the normalized photoluminescent emission spectra of typPy(acac), bzqPt(acac), and btpPt(acac).
Figure 16:
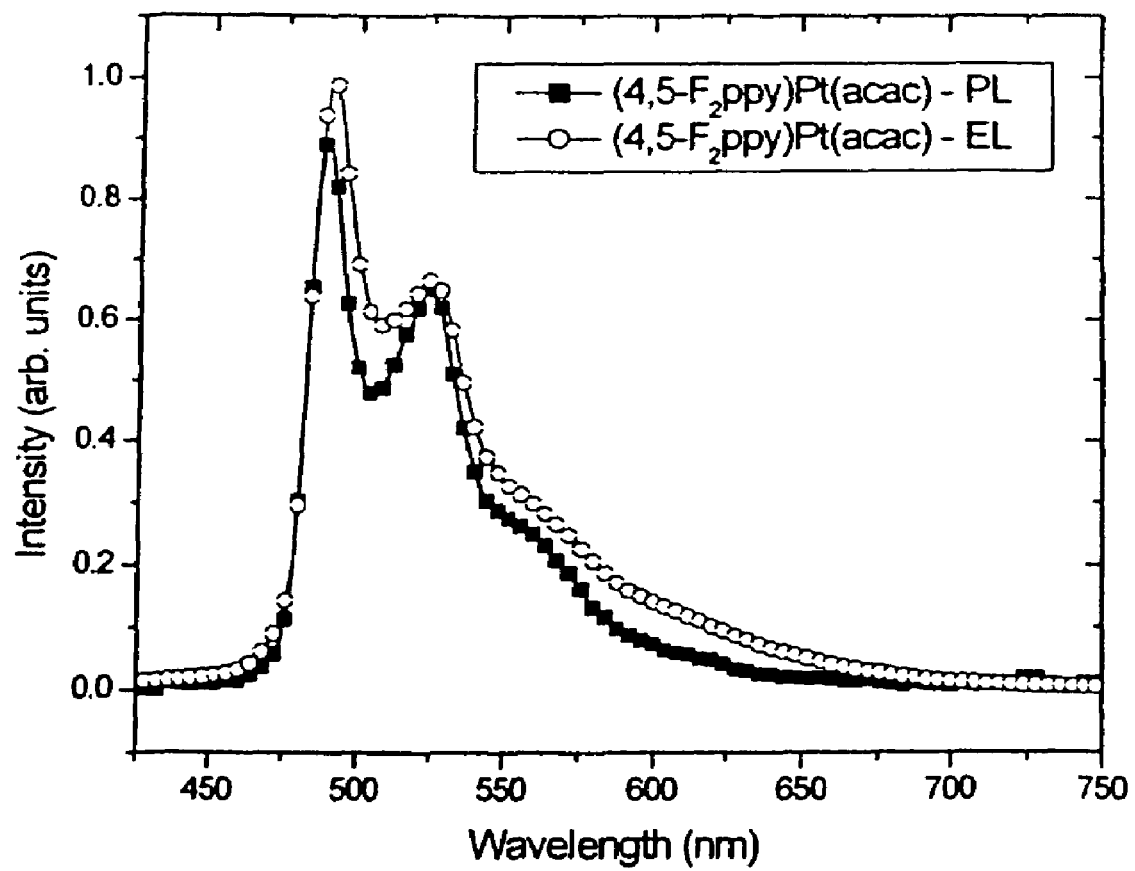
FIG. 16 illustrates the normalized electroluminescent emission spectra for OLEDs prepared with (2-(4,5-F$_2$phenyl)pyridinato)platinum(acetyl acetonate). The OLEDs had a ITO/PVK-PBD-dopant/Alq$_3$/Mg—Ag layer structure. The PVK layer was deposited as a single, homogeneous layer by spin coating. PVK=polyvinylcarbaozole and PBD=(4-biphenyl)(4-tertbutyl)oxidiazole. The Alq$_3$ and Mg—Ag layers were deposited by thermal evaporation. The OLED had an external efficiency of 1.3% and a turn on voltage of 5 Volts. The spectra of the EL output as well as the PL signal are shown.

Platinum(II) (2-phenylpyridinato-NC$^{2'}$) (acetyl acetonate) [Pt(ppy)(acac)]. 100 mg of Pt(Ppy)(μ-Cl)$_2$Pt(ppy) dimer, 25 mg of 2,4-pentanedione and 85 mg of anhydrous sodium carbonate were refluxed at 100° C. in 8 ml of 2-ethoxyethanol under inert gas atmosphere for 15 hours. Cooling to room temperature, addition of cold water and filtration yielded crude product that after drying and flash chromatography (silica/dichloromethane) gave bright yellow-green solid (36% yield). $^1$H NMR (360 MHz, acetone-d$_6$), ppm: 9.00 (d, 1H, J=5.8 Hz), 8.02 (dt, 1H, J 1.6, 7.4 Hz), 7.89 (d, 1H, J 7.9H), 7.57 (dd, 1H, J 1.6, 7.4 Hz), 7.51 (dd, 1H, J 1.6, 7.9 Hz), 7.32 (dt, 1H, J 1.6, 6.8 Hz), 7.11 (dt, 1H, J 1.6, 7.9 Hz), 7.04 (dt, 1H, J 1.6, 7.4 Hz), 5.55 (s, 1H), 1.96 (s, 3H), 1.95 (s, 3H). See FIG. 12, compound number 5. See also FIG. 9(*a*).

Platinum(II) (2-(p-tolyl)pyridinato-N,C$^{2'}$) (acetyl acetonate) [Pt(tpy)(acac)]. 100 mg of Pt(tpy)(μ-Cl)$_2$Pt(tpy) dimer, 25 mg of 2,4-pentanedione and 85 mg of anhydrous sodium carbonate were refluxed at 100° C. in 8 ml of 2-ethoxyethanol under inert gas atmosphere for 15 hours. Cooling to room temperature, addition of cold water and filtration yielded crude product that after drying and flash chromatography (silica/dichloromethane) gave bright yellow-green solid (42% yield). $^1$H NMR (360 MHz, CDCl$_3$), ppm: 8.94 (d, 1H, J=5.9 Hz), 7.74 (t, 1H, J=6.8 Hz), 7.53 (d, 1H, J=7.8 Hz), 7.39 (s, 1H), 7.30 (d, 1H, J=7.8 Hz), 7.04 (t, 1H, J=6.8 Hz), 6.88 (d, 1H, J=7.8 Hz), 5.45 (s, 1H), 2.00 (s, 3H), 1.98 (s, 3H), 1.95 (s, 3H). See FIG. 12, compound number 1. See also FIG. 9(*b*).

Platinum(II) (7,8-benzoqionolinato-N,C$^{3'}$) (acetyl acetonate) [Pt(bzq)(acac)]. 100 mg of Pt(bzq)(μCl)$_2$Pt(bzq) dimer, 25 mg of 2,4-pentanedione and 85 mg of anhydrous sodium carbonate were refluxed at 100° C. in 8 ml of 2-ethoxyethanol under inert gas atmosphere for 15 hours. Cooling to room temperature, addition of cold water and filtration yielded crude product that after drying and flash chromatography (silica/dichloromethane) gave bright yellow solid (27% yield). $^1$H NMR (360 MHz, acetone-d$_6$), ppm: 9.13 (d, 1H, J=5.4 Hz), 8.25 (d, 1H, J=8.3 Hz), 7.75 (m, 2H), 7.50-7.57 (m, 3H), 7.44 (dd, 1H, J 5.4, 5.4 Hz), 5.52 (s, 1H), 2.04 (s, 6H). See FIG. 12, compound number 2. See also FIG. 9(*c*).

Platinum(II) (2-benzylpyrinato-N,C2') (acetyl acetonate) [Pt(bzpy)(ocac)]. 100 mg of Pt(bzpy)(μ-Cl)$_2$Pt(bzpy) dimer, 25 mg of 2,4-pentanedione and 85 mg of anhydrous sodium carbonate were refluxed at 100° C. in 8 ml of 2-ethoxyethanol under inert gas atmosphere for 15 hours. Cooling to room temperature, addition of cold water and filtration yielded crude product that after drying and flash chromatography (silica/dichloromethane) gave bright yellowish green solid (20% yield). $^1$H NMR (500 MHz, CDCl$_3$), ppm: 8.88 (d, 1H), 7.71 (t, 1H), 7.35-7.43 (m, 2H), 7.13 (t, 1H), 6.98-7.02 (m, 2H), 6.91 (t, 1H), 5.49 (s, 1H), 4.16 (s, 2H), 1.96 (s, 3H), 1.95 (s, 3H).

Platinum(II) (2-(2'-thienyl)pyridinato-N,C$^{3'}$) (acetyl acetonate) [Pt(thpy)(acac)]. 100 mg of Pt(thpy)(μ-Cl)$_2$Pt (thpy) dimer, 25 mg of 2,4-pentanedione and 85 mg of anhydrous sodium carbonate were refluxed at 100° C. in 8 ml of 2-ethoxyethanol under inert gas atmosphere for 15 hours. Cooling to room temperature, addition of cold water and filtration yielded crude product that after drying and flash chromatography (silica/dichloromethane) gave bright orange solid (20% yield). $^1$H NMR (500 MHz, CDCl$_3$) ppm: 8.78 (d, 1H), 7.67 (t, 1H), 7.46 (d, 1H), 7.26 (d, 1H), 7.17 (d, 1H), 6.86 (t, 1H), 5.46 (s, 1H), 1.98 (s, 3H), 1.95 (s, 3H).

Platinum(II) (2-(2'-(4'5'-benzothienyl)pyridinato-N,C$^{3'}$) (acetyl acetonate) [Pt(btp)(acac)]. 100 mg of Pt(btp)(μ-Cl)$_2$Pt(btp) dimer, 25 mg of 2,4-pentanedione and 85 mg of anhydrous sodium carbonate were refluxed at 100° C. in 8 ml of 2-ethoxyethanol under inert gas atmosphere for 15 hours. Cooling to room temperature, addition of cold water and filtration yielded crude product that after drying and flash chromatography (silica/dichloromethane) gave orange-red solid (20% yield). $^1$H NMR (360 MHz, CDCl$_3$), ppm: 8.90 (d, 1H, J=5.9 Hz), 8.75-8.79 (m, 1H), 7.77-7.81 (m, 1H), 7.71 (dt, 1H, J 1.5, 7.8 Hz), 7.27-7.34 (m, 3H), 6.95 (dt, 1H, J 1.5, 6.8 Hz), 5.54 (s, 1H), 2.08 (s, 3H), 2.01 (s, 3H). See FIG. 12, compound number 3. See also FIG. 9(*e*).

Platinum(II) (2-(4',6'-difluorophenyl)pyridinato-N,C$^{2'}$) (acetyl acetonate) [Pt(4,6-F$_2$ ppy)(acac)]. 131 mg of Pt(4,6-F$_2$ ppy)(μ-Cl)$_2$Pt(4,6-F$_2$ ppy) dimer, 43 mg of 2,4-pentanedione and 109 mg of anhydrous sodium carbonate were refluxed at 100° C. in 10 ml of 2-ethoxyethanol under inert gas atmosphere for 15 hours. Cooling to room temperature, addition of cold water and filtration yielded crude product that after drying and flash chromatography (silica/dichloromethane) gave bright yellow solid. $^1$H NMR (360 MHz, acetone-d$_6$, ppm: 9.06 (dt, 1H, J 1.0, 5.9 Hz), 8.08-8.13 (m, 1H), 8.01 (dt, 1H, J 1.5, 8.3 Hz), 7.38-7.43 (m, 1H), 7.05 (dd, 1H, J 2.4, 9.3 Hz), 6.69-6.76 (m, 1H), 5.61 (s, 1H), 2.01 (s, 3H), 1.99 (s, 3H). See FIG. 12, compound number 4. See also FIG. 9(*d*).

Platinum(II) (2-(4',5'-difluorophenyl)pyridinato-N,C$^{2'}$) (acetyl acetonate) [Pt(4,5-F$_2$ ppy)(acac)]. 68 mg of Pt(4,5-F$_2$ ppy)(μ-Cl)$_2$Pt(4,5-F$_2$ ppy) dimer, 36 mg of 2-picolinoc acid and 57 mg of anhydrous sodium carbonate were refluxed at 100° C. in 5 ml of 2-ethoxyethanol under inert gas atmosphere for 15 hours. Cooling to room temperature, addition of cold water and filtration yielded crude product that after drying and flash chromatography (silica/dichloromethane) gave bright yellow solid. $^1$H NMR (360 MHz, acetone-d$_6$), ppm: 8.99 (d, 1H, J=5.7 Hz), 8.06 (dt, 1H, J 2.3, 8.0 Hz), 7.90 (d, 1H, J=8.0 Hz), 7.62-7.68 (m, 1H), 7.37 (tt, 1H, J 1.7, 5.7 Hz), 7.20-7.25 (m, 1H), 5.58 (s, 1H), 1.99 (s, 3H), 1.98 (s, 3H). See FIG. 12, compound number 6. See also FIG. 9(*f*).

Platinum(II) (2-(4',5'-difluorophenyl)pyridinato-N,C$^{2'}$) (2-picolinato) [Pt(4,5F$_2$ppy)(pico)]. 69 mg of Pt(4,5-F$_2$ ppy)(μ-Cl)$_2$Pt(4,5-F$_2$ ppy) dimer, 30 mg of 2-picolinoc acid and 52 mg of anhydrous sodium carbonate were refluxed at 100° C. in 5 ml of 2-ethoxyethanol under inert gas atmosphere for 15 hours. Cooling to room temperature, addition of cold water and filtration yielded crude product that after drying and flash chromatography (silica/dichloromethane) gave bright yellow solid. $^1$H NMR (500 MHz, CDCl$_3$), ppm: 9.15 (d, 1H, J=5.6 Hz), 9.05 (d, 1H, J=5.6 Hz), 8.08-8.21 (m, 2H), 7.89 (td, 1H, J 1.2, 8.0 Hz), 7.68-7.71 (m, 1H), 7.54 (d, 1H, J=8.0 Hz), 7.32-7.36 (m, 1H), 7.12-7.20 (m, 2H). See FIG. 12, compound number 7. See also FIG. 9(*g*).

Platinum(II) (2-(4'-cyanophenyl)pyridinato-N,C$^{2'}$) (acetyl acetonate) [Pt(cppy)(acac)]. 69 mg of Pt(cppy)μ-Cl)$_2$Pt(cf-ppy) dimer, 58 mg of 2-picolinoc acid and 52 mg of anhydrous sodium carbonate were refluxed at 100° C. in 5 ml of 2-ethoxyethanol under inert gas atmosphere for 15 hours. Cooling to room temperature, addition of cold water and filtration yielded crude product that after drying and flash chromatography (silica/dichloromethane) gave bright yellow solid. $^1$H NMR (360 MHz, acetone-d$_6$), ppm: 9.07 (dt, 1H, J 1.0, 5.9 Hz), 8.14 (dt, 1H, J 1.5, 7.8 Hz), 8.05 (dt, 1H, J 1.0, 8.3 Hz), 7.77-7.79 (m, 2H), 7.46-7.50 (m, 1H), 7.43 (dd, 1H, J 1.5, 8.3 Hz), 5.61 (s, 1H), 2.01 (s, 6H).

OLED preparation and testing. Polymer blend OLEDs were spun coat from chloroform solution on patterned pre-cleaned and oxygen plasma treated indium tin oxide (ITO) coated glass substrates and covered with vacuum-deposited aluminum(III) tris(8-hydroxyquinolinate) and/or Mg:Ag (10:1 weight ratio) cathode (500 Å) for the single-layer and heterostructure architectures, respectively. Typically, 7.5 ml of a chloroform solution contained 100 mg of PVK, 40 mg of PBD and 2.5 mg of (45F$_2$ ppy)Pt(acac). Chosen spincoating conditions (3000 RPM, 40 s, Specialty Coating Systems, Inc.) led to 1300±20 Å-thick PVK:PBD: dye films as determined by ellipsometry (Rudolph automatic ellipsometer equipped with a He:Ne laser). Prior to spinning, the solutions were filtered through a 0.2 μm filter. Tris(8-hydroxyquinoline) aluminum (III) (Sigma-Aldrich, Inc) (Alq$_3$) was sublimed prior to use. All measurements on the devices were carried out in air at-room temperature. Device current-voltage and light intensity characteristics were measured using the LabVIEW™ program by National Instruments with a Keithley 2400 SourceMeter/2000 Multimeter coupled to a Newport 1835-C Optical Meter. Electroluminescence spectra were recorded at room temperature on a PTI QuantaMaster™ Model C-60SE spectrofluorometer.

Other methods known to those skilled in the art, of fabricating OLEDs may be used.

Since the discovery that phosphorescent materials can be used as the emissive material in highly efficient OLEDs, there is now much interest in finding still more efficient electrophosphorescent materials and OLED structures containing such materials. High efficiency organic light emitting devices (OLEDs) using the phosphorescent dopant, fac tris(2-phenylpyridine)iridium (Ir(ppy)$_3$), have been demonstrated using several different conducting host materials. See, for example, M. A. Baldo et al., Nature, vol. 395, 151 (1998); D. F. O'Brien et al., Appl. Phys. Lett., vol. 74, 442 (1999); M. A. Baldo et al., Appl. Phys. Lett., vol. 75, 4 (1999); T. Tsutsui et al., Japanese. J. Appl. Phys., Part 2, vol. 38, L1502 (1999); C. Adachi et al., App. Phys. Lett., vol. 77, 904 (2000); M. J. Yang et al., Japanese J. Appl. Phys., Part 2, vol. 39, L828 (2000); and C. L. Lee et al., Appl. Phys. Lett., vol. 77, 2280 (2000). Since the triplet level of the metal-ligand charge transfer state of the green-emitting Ir(ppy)$_3$ is between 2.5 eV and 3.0 eV, deep blue fluorophores with a peak wavelength at about 400 nm, such as 4,4'-N,N'-dicarbazole-biphenyl (CBP), are likely candidates as triplet energy transfer and exciton confining media. Using 6% to 10%-Ir(ppy)$_3$ in CBP leads to efficient Ir(ppy)$_3$ phosphorescence. In addition to the energetic resonance between the dopant and the host, the control of charge carrier injection and transport in the host layers is believed to be necessary for achieving efficient formation of radiative excitons. High electrophosphorescence efficiency has been achieved using Ir(ppy)$_3$ doped into CBP along with a 2,9-dimethyl-4,7-diphenyl-phenanthroline (BCP) electron transport and exciton blocking layer. M. A. Baldo et al., Appl. Phys. Lett., vol. 75, 4 (1999). In that device, the doped CBP layer was found to readily transport holes.

The compound 4,4',4"-tris(3-methylphenylphenylamino)triphenylamine ("m-MTDATA") was disclosed for use as a hole injecting material in electroluminescent OLEDs in which fluorescence was obtained from an electron transporting layer comprised of tris(8-hydroxyquinoline)aluminum ("Alq$_3$"). See Shirota et al., Appl. Phys. Lett., vol. 65, no. 7, 807 (1994).

Four processes determine the overall efficiency of energy transfer between a host and a guest molecule: the rates of exciton relaxation on the guest and host, $k_G$ and $k_H$, respectively, and the forward and reverse triplet transfer rates between guest and host, $k_F$ and $k_R$, respectively. The rate equations, in the absence of exciton-formation processes, are $$\frac{dG}{dt} = -k_G G - k_R G + k_p H, \qquad (1)$$

$$\frac{dH}{dt} = -k_H H - k_p H + k_R G,$$

where G and H are the densities of guest and host triplet excitons. The solutions to equation (1) are biexponential decays of the form $$G, H = A_1 \exp[k_1 t] + A_2 \exp[-k_2 t], \qquad (2)$$

In various embodiments of the present invention, the materials used are (a) N$_1$N'-diphenyl-N$_1$bis(3-methylphenyl)-[1,1-biphenyl]-4,4'-diamine (TPD), (b) 2,9-dimethyl-4,7-diphenyl-1,10-phenanthroline(bathocuproine or BCP), (c) 4,4'-N,N'-dicarbzaole-biphenyl (CBP), (d) Alq$_3$, (e)fac tris (2-phenylpyridine) iridium [Ir(ppy)$_3$][14] and (f) 2,3,7,8,12,13,17,18-ocraethyl-21H,23H-porphine platinum(II) (PrOEP). Of these materials, TPD and CBP are predominantly hole-transport and Alq$_3$; and BCP are electron-transport materials. Two phosphors are also employed as guests, Irx(ppy)$_3$, which emits at ~510 nm which a phosphorescent lifetime of –0.4 μs, id and PrOEP, which emits at 650 nm with a phosphorescent lifetime: of –100 μs$^3$.

In accordance with the present invention, faster phosphorescent rates can produce better emission results. An embodiment of the present invention concerns, among other things, the following relationship: k_phos*exp(–delta_G/kT)>k_host. The k_phos is the phosphorescence rate, that is, in the present invention greater than about 1×10$^5$/sec and/or 1×10$^6$/sec. The delta_G is the difference in free energy, which in this case is substantially equal to the energy difference between the host and the guest triplets. The kT is the thermal energy and is about 0.025 eV at typical device operating temperatures. The k_host is the host decay rate; in certain embodiments of the present invention, the k_host is equivalent to the radiative and non-radiative decay rates, equaling less than about 5×10$^3$/sec. Thus, within the relationship identified, namely, k_phos*exp(delta_G/kT)>k_host, if k_phos is about 1×10$^5$/sec, kT is about 0.025 eV, and k_host is about 5×10$^3$/sec, then delta_G is less than about 0.075 eV. An outer boundary for delta_G in this particular case can be that delta_G is less than about 0.17 eV. The outerlimit decision can be made in reference to the type of host material being used due to such factors as stability. Also, hosts with larger triplet energy levels can increase the device voltage.

Further, in embodiments of the present invention, the overall triplet decay rate should not be too small in order to minimize other losses. In another embodiment of the present invention, k_phos is about 1×10$^6$/sec, k_host is about 1×10$^3$/sec and delta_G is less than about 0.17 eV. In another embodiment of the present invention, k_phos is about 1×10$^5$/sec, k_host is about 5×10$^3$/sec and delta_G is less than about 0.17 eV. In a preferred embodiment of the present invention, k_phos is about 1×10$^6$/sec, k_host is about 1×10$^3$/sec and delta_G is less than about 0.075 eV. Further embodiments can be based on this relationship.

In an embodiment of the present invention, FIG. 17 shows the molecular structures of the materials studied: (a) TPD (N,N'-diphenyl-N,N'-bis(3-merhylphenyl)-[1,1'-biphenyl]4, 4'-diamine), (b) BCP (2,9-dimethyl-4,7-diphenyl-1,10-phenanthroline), (c) CBP (4,4'-N,N'-dicarbazole-bipphenyl), (d) $Alq_3$ tris(8-hydroxyquinoline) aluminum, (e) $Ir(ppy)_3$ fac tris(2-phenylpyridine)iridium, and (f) PtOEP 2,3,7,8,12,13, 17,18-octaethyl-21H.23H-porphine platinum(II). FIG. 17(g) further shows the triplet dynamics in a guest host system of the present invention. FIG. 17(g) shows the rates of forward and back transfer, $k_F$ and $k_G$, respectively, which are determined by the Gibb's free energy change ($\Delta G$) and the molecular overlap. The rates of decay from the guest and host triplet states are labeled $k_G$ and $k_H$, respectively.

The simplified OLED structures of the present invention are demonstrated herein for OLED structures in which the organic hole trapping material is a phosphorescent emissive guest material for which the emission is produced from a triplet excited state of an organic molecule. Thus, while the representative embodiments of the present invention are illustrated and described herein as using a phosphorescent organic material as the emissive guest material in the electron transporting host material, the full scope of the present invention can also include a fluorescent material as the emissive material in the electron transporting host material.

Figure 18:
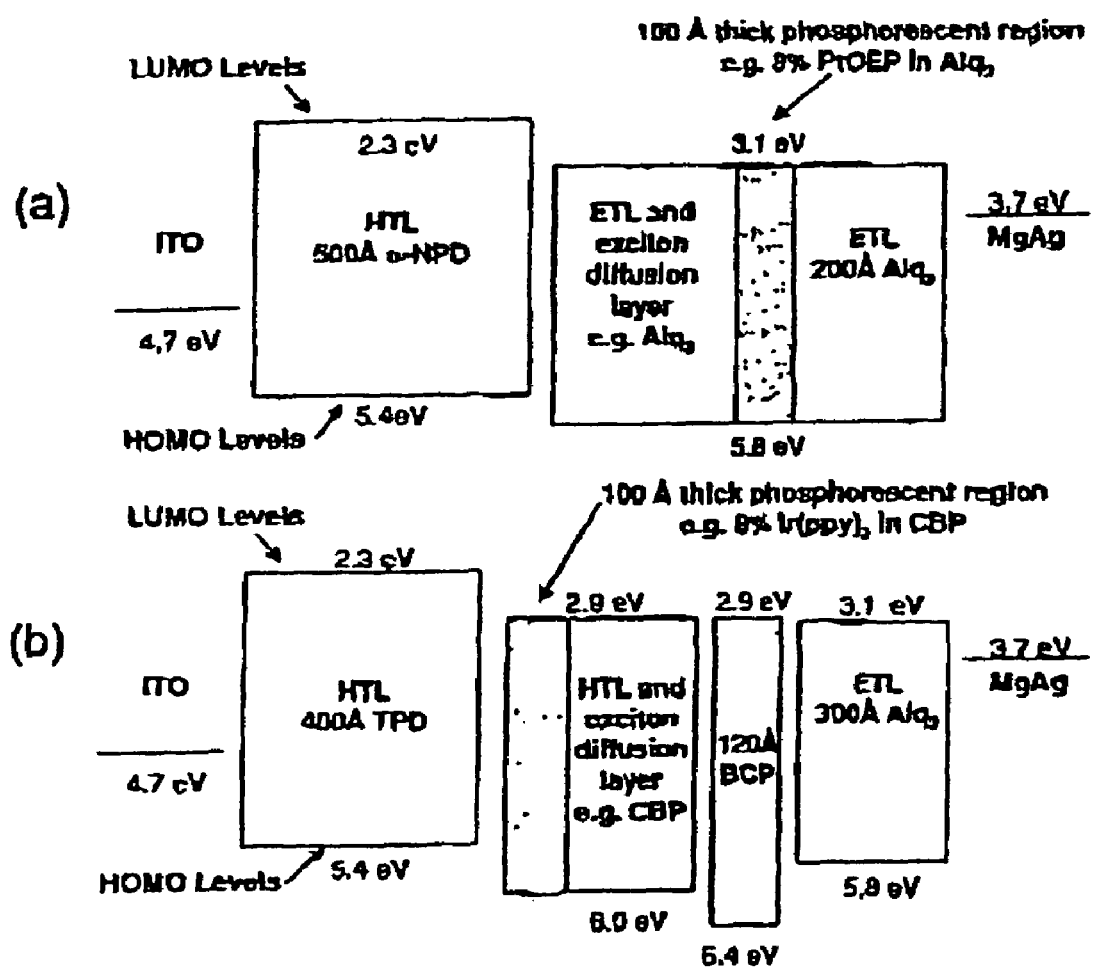
FIG. 18 shows the structure of the electroluminescent devices used to observe the transient response of triplet diffusion in organic host materials.

In FIG. 18, the structure of the electroluminescent devices is used to observe the transient response of triplet diffusion in organic host materials. Electron and hole transport layers are labeled ETL and HTL, respectively. The highest occupied molecular orbital (HOMO) obtained for each material corresponds to its ionization potential (IP). The lowest unoccupied molecular orbital (LUMO) is equal to the IP plus the optical energy gap, as determined from absorption spectra. Relative alignments of the energies in the fully assembled devices will differ from those shown. Two devices are shown: in FIG. 18(a) the host preferentially transports electrons and the exciton formation zone is at the interface between the host and α-NPD; in FIG. 18(b) the host preferentially transports holes and exciton formation is at the interface between the host and BCP. In both devices triplets are forced to diffuse through the host before reaching a phosphorescent dye. Singlets formed during electrical excitation cause fluorescence within the host, thus triplet dynamics are reflected in the delay between fluorescence and phosphorescence.

For electroluminescent devices employing $Alq_3$ as the host, the exciton-formation zone is located at the interface of the HTL and $Alq_3$. In the case of HTL host materials, the exciton-formation zone is at the interface between the HTL and BCP. To study exciton diffusion, undoped layers of the host material were inserted between the exciton-formation interface and a phosphorescent layer. As shown in FIG. 18, triplets are forced to diffuse through this undoped zone before being captured by the doped luminescent, or "triplet sensing," layer. Also shown in FIG. 18 are proposed energy levels for the host and guest materials. The electron energy levels referenced to vacuum are indicated by the lowest unoccupied molecular orbital (LUMO) and the energy levels of holes are given by the highest occupied molecular orbitals (HOMO), as determined from the ionization potential for each material. It may be assumed here that the HOMO-LUMO gap is equal to the optical energy gap, as determined from absorption spectra. Under this assumption, the LUMO does nor necessarily serve as the lowest conduction level for mobile electrons. Although not shown here, charge redistributions and polarization effects at the heterointerfaces are expected to alter the relative energy-level alignments when differing materials are brought into contact.

The triplet energies, measured from the highest energy peak of the PL spectra, and decay lifetimes are summarized in Table I. From the triplet energies, the free energy change $\Delta G$ on triplet transfer can be calculated for combinations of host and guest materials. Given the guest materials PtOEP and $Ir(ppy)_3$, it is possible to categorize several host and guest combinations based on the magnitude and sign of $\Delta G$ (see FIG. 17). In one embodiment of the present invention when $\Delta G \ll\ll 0$, the guest-host combinations where triplets on guest molecules are strongly confined include PtOEP in CBP and PtOEP in TPD. In these cases, the guest and host triplet energies are nonresonant; hence although $k_F \gg\gg k_R$, both rates are much smaller than their resonance maxima.

In another embodiment of the present invention when $\Delta G<0$, there are two examples of weak triplet confinement: PtOEP in $Alq_3$ and $Ir(ppy)_3$ in CBP. Here $k_F>k_R$, the system is close to resonance, and significant populations of both guest and host triplets exist. In yet another embodiment of the present invention when $\Delta G>0$, in films of $Ir(ppy)_3$ in TPD the triplets are expected to reside primarily on the host with $k_R>k_F$. In another embodiment of the present invention when $\Delta G\gg 0$, $Ir(ppy)_3$ in $Alq_3$ exhibits extremely inefficient phosphorescence due to $Alq_3$ quenching of $Ir(ppy)_3$ triplets (corresponding to $k_R>k_F$), and will not be considered further.

In another embodiment of the present invention, the efficiency of phosphorescence depends on the creation rates of triplets on the host and guest species. For example, it the bulk of excitons are formed on the guest molecular species, then efficient phosphorescence may be possible even though triplets are only weakly confined. Therefore, to understand a particular electrophosphorescent guest-host system, we need to know the site of exciton formation. This may be determined by analysis of the phosphorescent transients. The phosphorescent material in the structures of FIG. 18 can be displaced from the exciton formation zone, forcing triplets to diffuse across several hundred angstroms of organic material prior to recombination. To measure the diffusion time, we first apply a short electrical pulse and generate singlet and triplet excitons at the ETL/HTL interface. The formation of excitons follows the current transient and is observed by measuring transient fluorescence from singlets in the host material. Then after the electrical excitation has ceased, the delay between the fluorescence and the onset of phosphorescence is measured. Either charge or triplet diffusion may be responsible for the delay, but charge diffusion can be effectively "turned off" by applying reverse bias following the excitation pulse to discharge traps and sweep out the remaining charge. Therefore, if similar delayed phosphorescence is observed in the presence and absence of reverse bias, than charge trapping on guest molecules must be significant. See Table I.

TABLE I

Material triplet energies and room temperature triplet lifetimes.

| Material | Triplet energy (±0.1 eV) | Triplet lifetime |
|---|---|---|
| PtOEP | 1.9 | 1.10 ± 10 µs |
| $Ir(ppy)_3$ | 2.4 | 0.8 ± 0.1 µs |
| CBP | 2.6 | >1 s |
| BCP | 2.5 | <10 µs |
| TPD | 2.3 | 200 ± 50 µs |
| $Alq_3$ | 2.0 | 25 ± 15 µs |

Since the probability of triplet transfer is proportional to the product of the electron and hole transfer probabilities, it is expected that triplet diffusion occurs at a slower rate than charge transport. However, even in cases where charge diffusion dominates the phosphorescent decay, there still may be additional triplet diffusion time. For example, the delay in the triplet transport or the various species may diffuse over different distances prior to localization on a phosphorescent molecule. Hence, in those systems where delayed phosphorescence is eliminated by reverse bias, it can be concluded that charge trapping is significant, but it is possible that rapid triplet diffusion also occurs.

Unlike fluorescent guest-host systems, the phosphorescent systems summarized in Table II do not require energy transfer from guest to host (i.e. $\Delta G<0$). Given minimal triplet losses in the host, the only relaxation pathway may be phosphorescence from the guest, and, as is observed in $Ir(ppy)_3$ in TPD, the overall electroluminescent quantum efficiency of phosphorescent OLED's with $\Delta G<0$ can be as high as 3%. In such a system, the excitons reside primarily on the host and are eventually transferred to phosphorescent guest sites prior to emission. Although guest-host combinations with $\Delta G<0$ generally exhibit superior performance by minimizing losses at the host, systems with $\Delta G<0$ may be useful for high energy triplet emitters such as blue phosphors.

Similar to $Ir(ppy)_3$ in TPD, triplet diffusion from host to guest is observed for PtOEP in $Alq_3$. From transient analyses of exciton transport in $Alq_3$. From transient analyses of exciton transport in $Alq_3$, it is likely that the transport is dispersive with behavior similar to charge transport. Nevertheless, in approximating it as a nondispersive system, we obtain a diffusion coefficient of D $r=(8\pm5)\times10^{-8}$ $cm^{2/5}$ and triplet lifetime of $r=(25\pm15)$ $\mu s$.

and at least a further doubling of phosphorescent efficiency should be possible given the right host material.

The deposition techniques for any of the above-listed layers and materials are well-known in the art. For example, a representative method of depositing the OLED layers is by thermal evaporation or spin coating if a polymer LED is used; a representative method of depositing metal layers is by thermal or electron-beam evaporation; and a representative method of depositing indium tin oxide is by electron-beam evaporation or sputtering.

The present invention may also be used to provide stable, efficient, high brightness, monochromatic, multicolor, or full-color, flat panel displays of any size. The images created on such displays could be text or illustrations in full-color, in any resolution depending on the size of the individual OLEDs. Display devices of the present invention are therefore appropriate for an extremely wide variety of applications including billboards and signs, computer monitors, and telecommunications devices such as telephones, televisions, large area wall screens, theater screens and stadium screens. The structures described herein are included, for example, in a plurality of pixels in a light emitting device or as part of a single-pixel, flat panel backlight device. Moreover, the structures described herein may be used as part of a laser device. Because of the exceptionally high luminous efficiencies that are possible for phosphorescent-based OLEDs, as compared with OLEDs generally, and especially with respect to conventional inorganic LEDs, the phosphorescent-based OLEDs of the present invention may also be used as a light source for illumination applications. Such light sources could replace conventional incandescent or fluorescent lamps for certain types of illumination applications.

TABLE II

The electrophosphorescent quantum efficiencies and several properties of a range of material combinations.

| Guest (lifetime) | Host | $\Delta G$ ($\pm 0.1^{eV}$) | Host lifetime | Emission lifetime ($\mu s$) | Trapping on guest | El quantum efficiency |
|---|---|---|---|---|---|---|
| PtOEP ($110 \pm 10$ $\mu s$) | CBP | −0.7 | >1 s | 80 ± 5 | Yes | 6% |
|  | $Ir(ppy)_3$ | −0.5 | <0.1 $\mu s$ | 80 ± 5 | ? | 3% |
|  | TPD | −0.4 | 200 ± 50 $\mu s$ | 80 ± 5 | Yes | 3% |
|  | $Alq_3$ | −0.1 | 25 ± 15 $\mu s$ | 40 ± 5 | No | 3% |
| $Ir(ppy)_3$ ($0.8 \pm 0.1$ $\mu s$) | CBP | −0.2 | >1 s | 0.4 ± 0.50 | Yes | 8% |
|  | TPD | +0.1 | 200 ± 50 $\mu s$ | 15 ± 2 | No | 3% |
|  | $Alq_3$ | +0.4 | 25 ± 15 $\mu s$ | <0.1 | ? | <0.1% |

All the guest-host systems employing the green phosphor $Ir(ppy)_3$ exhibit weak triplet confinement on the phosphorescent guest, i.e., $\Delta G\sim 0$. Indeed, reverse transfer from $Ir(ppy)_3$ to CBP is undoubtedly responsible for some losses in luminescence efficiency and the decrease in phosphorescent lifetime from ~0.8 to ~0.4 $\mu s$. In spite of this, external quantum efficiencies as high as 8% have been obtained from $Ir(ppy)_3$ doped in CBP.[4] As confirmed by the transient studies here, these efficiencies are possible because a majority of excitons are formed directly on $Ir(Ppy)_3$ following charge trapping. The deep HOMO level of CBP, in particular, appears to encourage hole trapping on phosphorescent guest. But there remains significant room for improvement, Such phosphorescence-based OLEDs could be used, for example, in large planar light sources that produce illumination of a desired color.

If the host material is an electron transporter, then it is used as an electron transport layer (ETL) and employed in the structure of FIG. 18(a). Of the host materials used, $Alq_3$ and BCP films may serve as an ETL; the remaining materials are predominantly hole conductors and can be used in hole-transport layers (HTL's). For these materials, a wide-energy-gap bole and exciton-blocking material are required to contain the excitations within the HTL. For this purpose, we used BCP in structures shown in FIG. 18(b). BCP can conduct electrons but blocks holes from entering the ETL.

The devices were fabricated by thermal evaporation of the source materials under high vacuum (≈10⁻⁶ Torr). In successive evaporations, a hole-transport material was deposited on a precleaned glass substrate coated with ITO. This was followed by deposition of the host material. Since the host was also an HTL, a 120 Å thick BCP blocking layer was employed. All devices employed an $Alq_3$ ETL to separate the emissive region from the 1000-Å-thick 20:1 Mg:Ag cathode, thereby positioning the luminescent region more favorably within the microcavity created by the metal cathode. The devices were completed by depositing a 500-Å-thick layer of Ag to protect the Mg—Ag cathode from oxidation. Metal depositions were defined by a shadow mask with an array of 1-mm-diameter openings.

Transient measurements were obtained by applying a narrow (200-ns) voltage pulse to the device under test and coupling the emission into a streak camera. This pulse width is chosen to be less than the radiative rate of the phosphors and larger than the charging time of the OLED, which for a 50-'Ω load and a typical capacitance of 1 nF is about 50 ns. In some cases, the sample was placed under −10 V reverse bias following the electrical pulse. External EL quantum efficiency measurements were made by placing the completed OLED directly onto the surface of a calibrated silicon photodetector and capturing every photon emitted in the forward (viewing) direction. All measurements were performed in air, except for those at low-temperature which were performed in an evacuated closed-cycle refrigerator.

Figure 19:
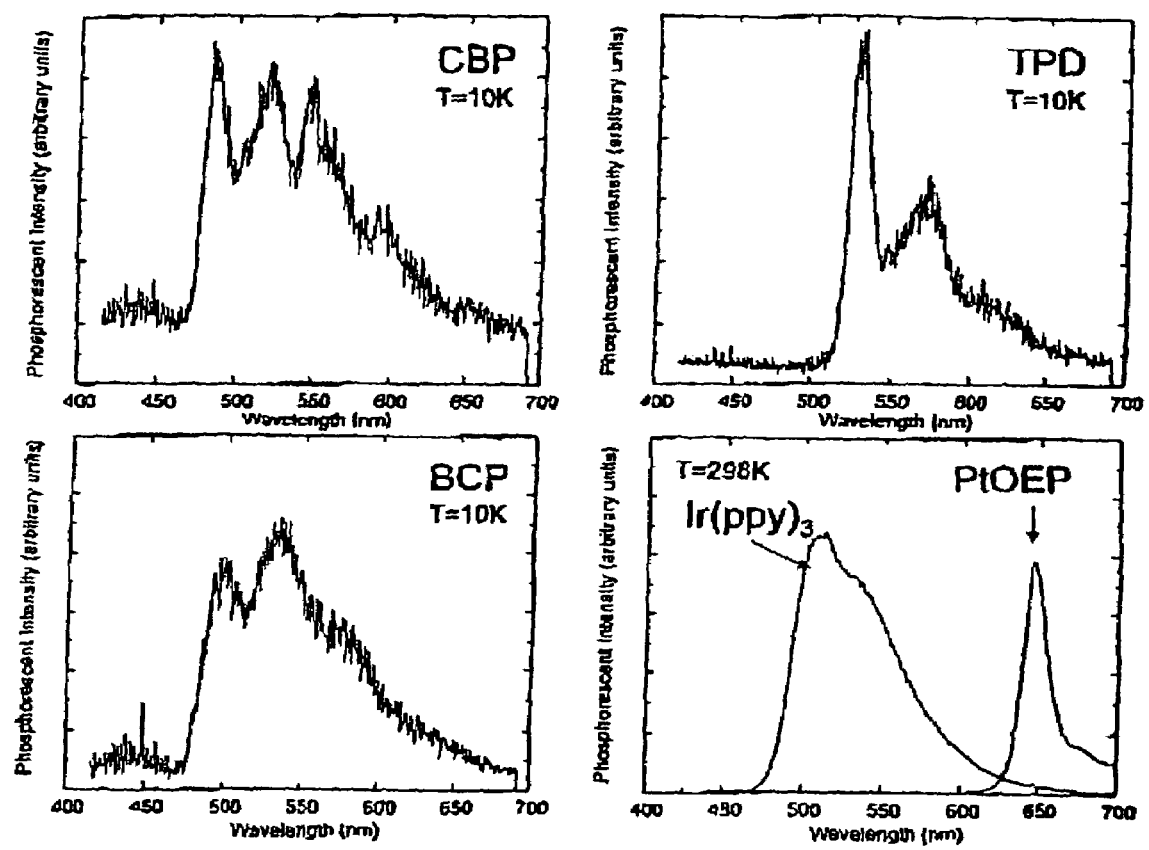
FIG. 19 shows the phosphorescent spectra of TPD, BCP, CBP and Ir(ppy)$_3$ with PtOEP according to the present invention.

The host materials, TPD, CBP, and $Alq_3$ are fluorescent and possess small or negligible phosphorescence at room temperature due to competing thermally activated nonradiative decay processes. In addition to intramolecular pathways, these nonradiative processes include triplet diffusion to defect sites followed by dissipative transitions. Reducing the temperature slows the rate of phonon-assisted decay and triplet diffusion, and the phosphorescent PL spectra for TPD, CBP, and BCP at T=10 K are shown in FIG. 19 together with the room-temperature spectra of PtOEP and $Ir(ppy)_3$. After extended sampling, it was possible to obtain the room-temperature phosphorescent spectra and lifetimes for TPD and CBP. These measurements were possible because the triplet lifetimes of these materials are relatively long at room temperature: 200±50 μs and >1 s, respectively. In fact, under ultraviolet excitation, weak orange CBP phosphorescence is visible to the naked eye at room temperature. In contrast, the triplet lifetime of BCP decreases rapidly as temperature increases from ~1 s at 10 K to <10 μs at room temperature, although we note that short triplet lifetimes may be dominated by energy transfer to physical or chemical defects.

No phosphorescence was observed from $Alq_3$ even at temperatures as low as ~10 K. In their study of hydroxyquinoline complexes, Ballardini et al., were similarly unsuccessful in observing phosphorescent emission from $Alq_3$, although they could observe the phosphorescent spectra of hydroxyquinoline complexes as Pb, Bi, Rh, Ir, and Pt. These latter materials all show triplet emission at 590-650 nm and while it is not certain that the triplet energy of $Alq_3$ also lies within this range, it seems likely that it is significantly red-shifted from the spectra of the other host materials in FIG. 19.

Figure 20:
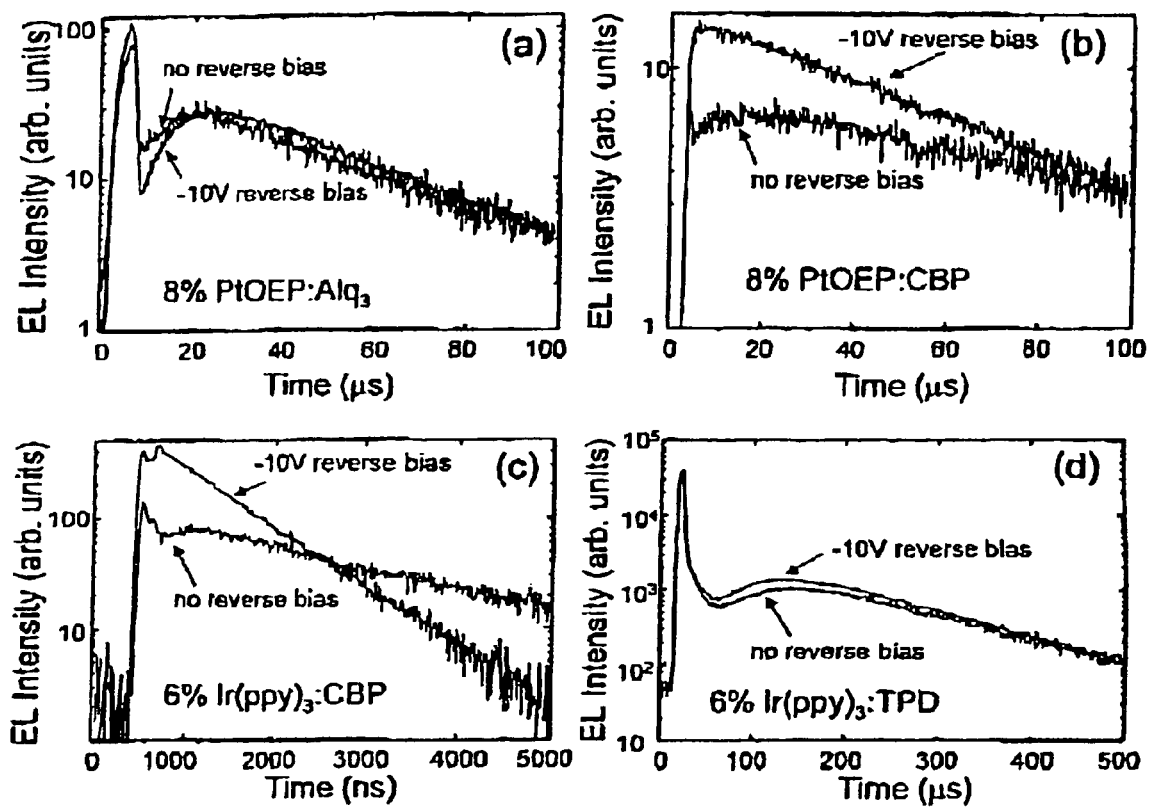
FIG. 20 shows the transient response of four phosphorescent guest-host systems according to the present invention.

In FIG. 20, the transient responses of four electrophosphorescent material systems are shown. The device in FIG. 20(a) consists of a 600-Å-thick $Alq_3$ diffusion layer and a phosphorescent sensing layer of 8% PtOEP doped in $Alq_3$ (8% PtOEP:$Alq_3$). The PtOEP: $Alq_3$ transients clearly exhibit delayed phosphorescence due to triplet diffusion in $Alq_3$ and also show minimal change when reverse bias is applied to the empty traps. However, in FIG. 20(b) we observe that a similar structure using a 8% PtLOEP:CEP emission layer fails to show delayed phosphorescence when reverse bias is applied. When reverse bias is absent, the decay lifetime is increased due to the transport of electrons across the 400-Å-thick diffusion layer, see FIG. 20(d). Here, the observed lifetime of $Ir(ppy)_3$ is ~15 μs, significantly longer than its natural radiative decay of 1 μs. Taken together with the apparent absence of charge trapping on $Ir(ppy)_3$ in TPD to $Ir(ppy)_3$ is the rate limiting step in $Ir(ppy)_3$ phosphorescence.

All systems exhibit delayed phosphorescence in the absence of reverse bias; however, only (a) PtOEP: $Alq_3$ and (d) $Ir(ppy)_3$=TPD delayed phosphorescence in the presence of a strong negative bias. Thus, we conclude that triplet energy transfer is present in these systems but that the other systems. (b) PtOEP:CBP and (c) $Ir(ppy)_3$: CBP, are dominated by charge trapping and exciton formation directly upon the phosphorescent molecular indeed, the deep HOMO level of CBP makes hole trapping on the guest likely when it is used as a host. In Sec. VII of the article entitled *Transient analysis of organic electrophosphoresence: I. Transient analysis of triplet energy transfer*, M. A. Baldo and S. R. Forrest, Physical Review B, vol. 62, no. 16, (2000), which is hereby incorporated by reference in its entirety, we discuss the relative merits of trapping and energy transfer as mechanisms for generating very high efficiency phosphorescent emission in OLEDs. But in the remainder of this and the following section we concentrate on those systems exhibiting energy transfer: notably, PtOEP: $Alq_3$ and $Ir(ppy)_3$: TPD.

In FIG. 20(d), the peak in the delayed phosphorescence of $Ir(ppy)_3$: TPD occurs over 100 μs after excitation. If we examine the transient of an $Ir(ppy)_3$: TPD device where there is no layer separating the excitron-formation interface from the luminescent zones, we find that delayed phosphorescence is absent and that the observed lifetime after electrical excitation is 15±2 μs (see FIG. 21(a)). Except for an initial peak containing some TPD fluorescence the decay is monoexponential and completely comprised of $Ir(Ppy)_3$ emission. The PL decay of 10% $Ir(ppy)_3$: TPD also exhibits long-lived differs in that the initial peak is larger than that found in the EL decay, and no emission is observed from TPD.

The data of FIGS. 20(d), 21(a), and 21(b) are to be compared with the natural phosphorescent lifetime of $Ir(ppy)_3$ which is only 1 μs. As expected from the relative phosphorescent spectra and lifetimes of TPD and $Ir(ppy)_3$, these data can be explained by triplets residing for extended periods on TPD molecules. The rate of forward transfer ($k_F$) is slow (~15 μs) and dominates the phosphorescent lifetime of $Ir(ppy)_3$ in TPD. We note that because the observed 15 μs $Ir(ppy)_3$ EL decay is also observed in the PL response, there must be significant populations of triplets in TPD after photoexcitation, i.e., $k_R \gg k_F$. The EL quantum efficiency of $Ir(ppy)_3$ in TPD is η~3%, providing evidence that efficient electrophosphorescence is possible even if it is energetically unfavorable for triplets to reside for an extended duration on the phosphor.

In FIG. 20, the transient response of four archetypal phosphorescent guest-host systems is shown. The PtOEP transients were recorded at λ=650±10 nm and the $Ir(ppy)_3$ transients at λ=530±30 nm. The initial peaks in the transient decays are host fluorescence at the wave lengths of interest they mark the formation of singlet excitons. Triplet energy transfer is demonstrated in (a) by PtOEP: $Alq_3$. These transients exhibit strong delayed phosphorescence due to triplet diffusion in Alq$_3$ and also show minimal change when reverse bias is applied to empty traps. This device had a 600-Å-tick Alq$_3$ diffusion layer and a phosphorescent sensing layer of 8% PtOEP in Alq$_3$. However, in (b) we observe that PtOEP: CBP fails to show delayed phosphorescence when reverse bias is applied, indicating that charge trapping on PtOEP is significant. This device had a 400-Å-thick CBP diffusion layer and a phosphorescent sensing layer of 8% PtOEP in CBP. Similarly, in (c) the transient response of Ir(ppy)$_3$:CBP also exhibits charge trapping on Ir(ppy)$_3$. This device had a 500-Å-thick CBP diffusion layer and a phosphorescent sensing layer of 6% Ir(ppy)$_3$ in CBP. Energy transfer to Ir(ppy)$_3$ is observed in Ir(ppy)$_3$: tpd (d). Here, the observed lifetime of Ir(ppy)$_3$ is 15 μs significantly longer than its natural radiative lifetime of 1 μs. Taken together with the apparent absence of charge trapping on Ir(ppy)$_3$ in TPD, this long lifetime indicates that energy transfer from TPD to Ir(ppy)$_3$ might be the rate limiting step in Ir(ppy)$_3$ phosphorescence. This device had a 200-Å-thick TPD diffusion layer and a phosphorescent sensing layer of 6% Ir(ppy)$_3$ in TPD. Note that the intensity of each transient measurement is arbitrary.

Figure 21:
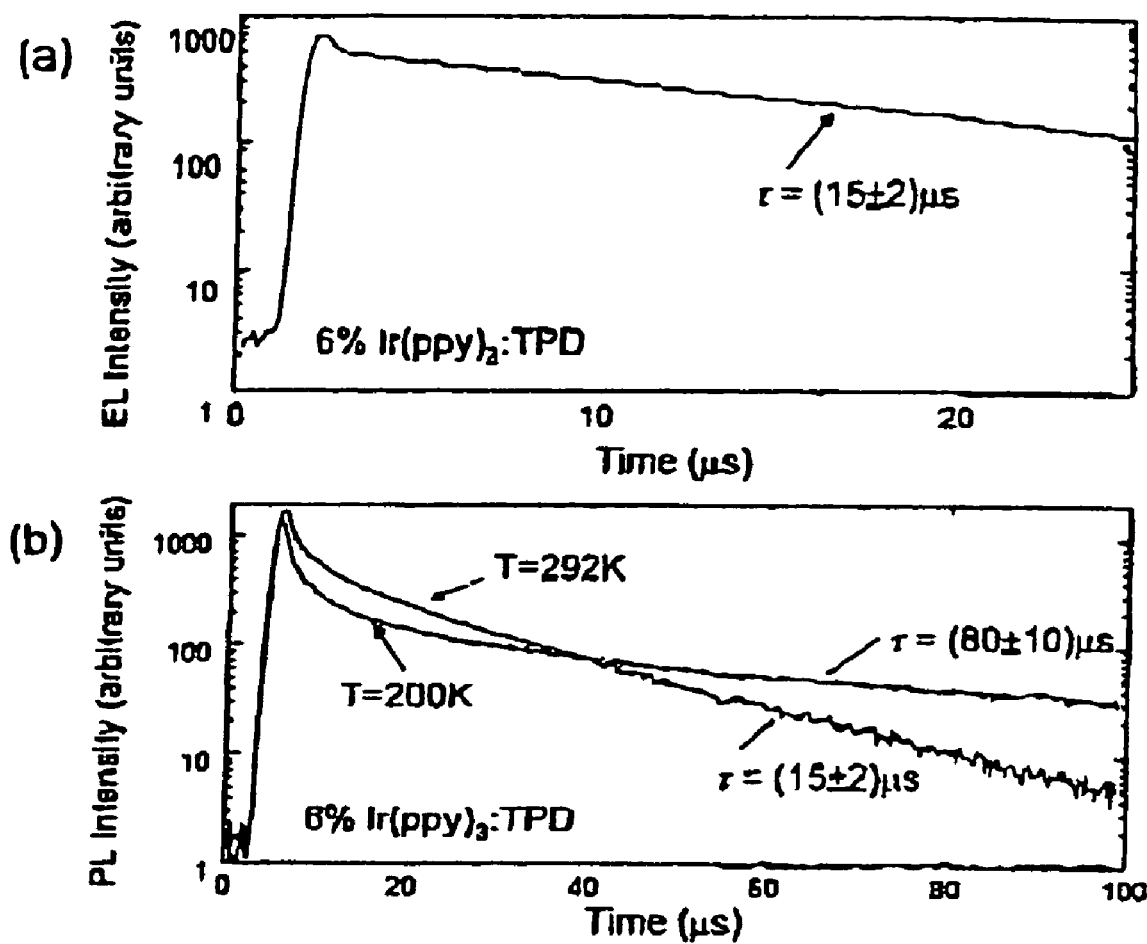
FIG. 21 shows the electroluminescent response of 8% Ir(ppy)$_3$ in TPD.

FIG. 21 shows (a) the electroluminescent response of 8% Ir(ppy)$_3$ in TPD. The device contains no diffusion layer yet the lifetime of Ir(ppy)$_3$ TPD is significantly longer (15 μs) than the natural radiative lifetime of Ir(ppy)$_3$ ($^-$1 μs). The initial peaks in the response is principally due to fluorescence from TPD at T=292 K and T=200 K. The lifetime increases at low temperatures, consistent with a thermally activated process. However, unlike the EL response, the initial transient in the photoluminescent response is comprised entirely of emission from photoexcited Ir(ppy)$_3$.

Figure 22:
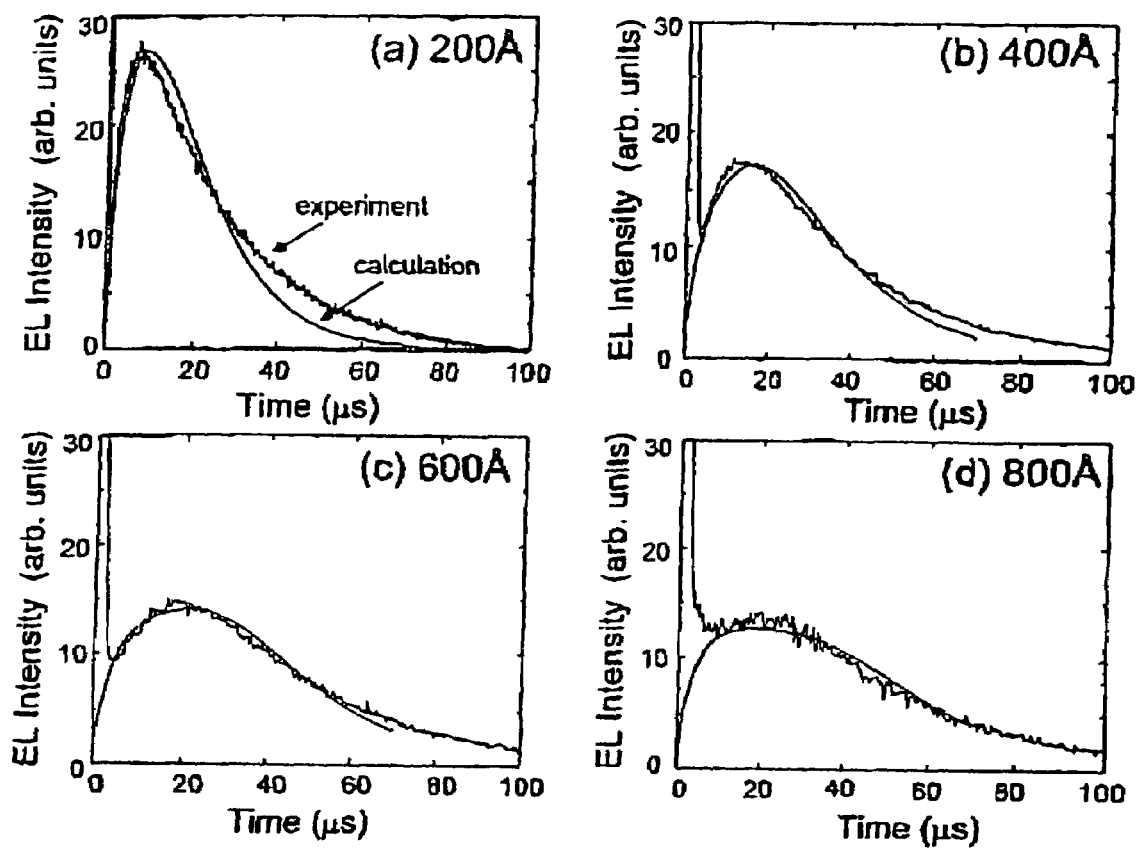
FIG. 22 shows the normalized phosphorescent transients for PtOEP in Alq$_3$ recorded at 650 nm for diffusion distances of (a) 200 Å, (b) 400 Å, (c) 600 Å and (d) 800 Å.

FIG. 22 shows the normalized, phosphorescent transients for PtOEP in Alq$_3$ recorded at 650 nm for diffusion distances of (a) 200 Å, (b) 400 Å, (c) 600 Å and (d) 300 Å. Also shown are the calculated transients (smooth curves) based on nondispersive diffusion of triplets given diffusion coefficient of D=(8±5)×10 μs cm$^{2/5}$, and a triplet exciton lifetime in Alq$_3$ of r=25±15 μs.

Figure 23:
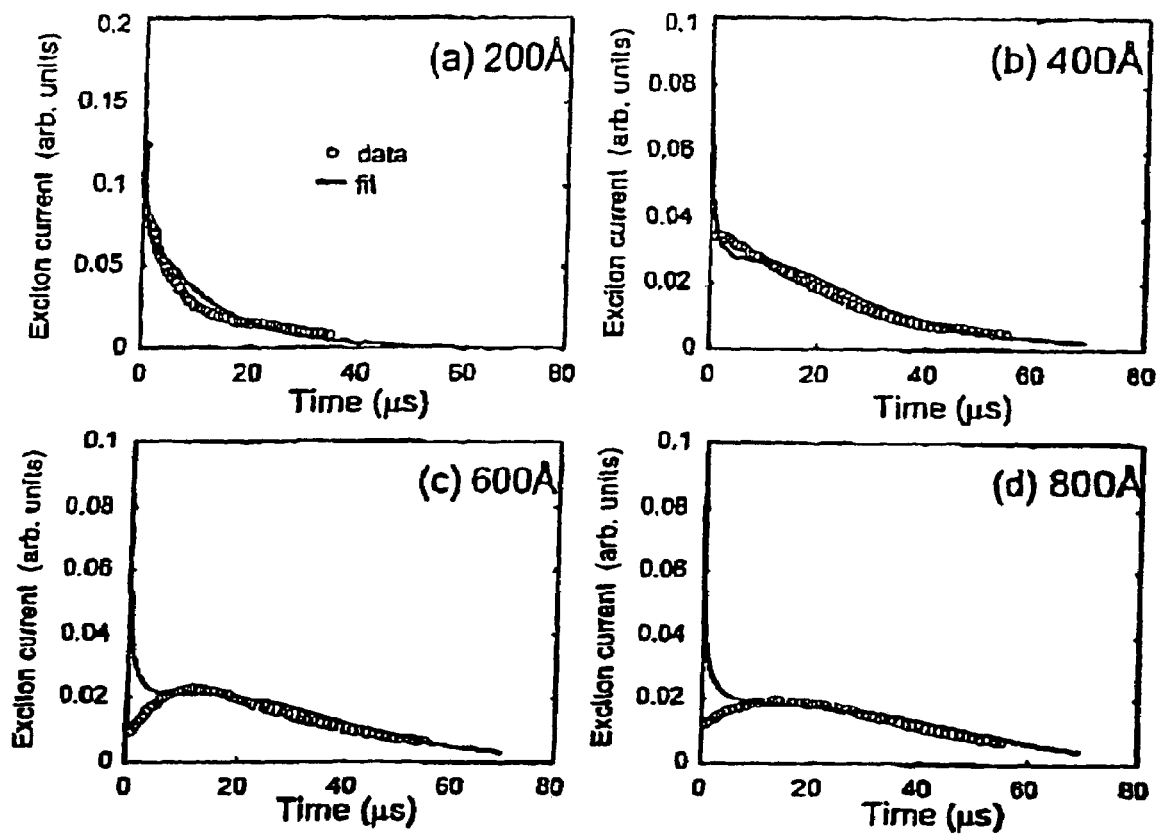
FIG. 23 shows the exciton current incident in the phosphorescent zone for diffusion distances (a) 200 Å, (b) 400 Å, (c) 600 Å and (d) 800 Å.

FIG. 23 shows the exciton current incident in the phosphorescent zone for diffusion distances (a) 200 Å, (b) 400 Å, (c) 600 Å and (d) 800 Å (points). The current is calculated (points) by deconvolving the phosphorescent decay of PtOEP from the traces in FIG. 22. Also shown are the best fits assuming nondispersive behavior, assuming that the concentration of exciton formation decreases exponentially with distance from the HTL/ETL interface with a characteristic length of L-120 Å (Ref. 21). The smooth curves in FIG. 22 are calculated from these fits by convolving them with the PtOEP phosphorescent decay.

Previous work has demonstrated the existence of triplet diffusion in Alq$_3$, and in FIGS. 22 and 23 we study the behavior of diffusing triplets as a function of time and distance. Layers consisting of 8% PtOEP: Alq$_3$ are used to detect the triplets via electrophorescence; but in contrast to the other devices grown in this work, here we vary the thickness of the Alq$_3$ spacer layer and observe the changes in the phosphorescent decay transient. FIG. 22 shows the normalized transient responses of PtOEP phosphorescence at λ,=650 nm for OLEDs with spacer layers of thickness (a) 200 Å, (b) 400 Å, (c) 600 Å, and (d) 800 Å. All traces exhibit delayed phosphorescence under reverse bias, demonstrating the presence of triplet diffusion.

These delayed responses are understood as convolutions of the rate of triplet arrival at the phosphorescent sensing layer with the phosphorescent decay of PtOEP. By deconvolving the phosphorescent lifetime of PtOEP from the observed decay, we can therefore extract the triplet exciton current entering the phosphorescent sensing layer of each device. The exciton current is calculated from the data of FIG. 22 by subtracting the initial fluorescent spikes, smoothing and then deconvolving the phosphorescent decay of PtOEP.

The triplet-exciton current, shown by the data points in FIG. 23, can be fitted to the diffusion equation:

$$\frac{d\varphi}{dt} = -\frac{\varphi}{T} D \frac{d^2\varphi}{dx^2} \tag{8}$$

As shown by the solid lines in FIG. 23, this fit is used to obtain values for the lifetime (r) of Alq$_3$ triplets and also their diffusion constant (D r). Finally, as a check, the predicted exciton currents are reconvolved with the PtOEP phosphorescent decay and compared to the measured transients of FIG. 22 (solid lines). For these fits, we assume that the exciton formation zone is the same in each device and that the exciton concentration decreases exponentially with distance from the HTL interface with a characteristic length of L~120 Å. The spikes at r~0 observed in the deconvolved exciton current are due to excess triplets formed within the phosphorescent zone and may indicate the presence of residual charge trapping.

From both FIGS. 22 and 23, we find that the simple theory provides a reasonable approximation to the observed transient decays of the PtOEP: Alq$_3$ system. Nevertheless, given a single value of D r, it is impossible to reproduce both the sharp initial increases in the phosphorescent transients and also their long tails. Thus, similar to charge transport, the data provide evidence for dispersive exciton transport, either due to the presence of exciton traps or a distribution in the diffusion coefficient arising from variation in molecular conformations within the amorphous Alq$_3$ film.

The data fall into two regimes: for short diffusion distances, D r determines the observed exciton currents, and at longer distances the currents are limited by the exciton lifetime r. From fits to devices with a spacer layer thickness of 200 Å or 400 Å we obtain a diffusion coefficient of D r=(8 200 or 400 Å∓5)×10$^{-8}$ cm$^{2/5}$, and from fits to the 600- and 800-Å devices, we obtain an exciton lifetime of r→25±15 μs taken together to yield a diffusion length of L$_d$=140±90 Å. This is less than the length calculated previously[2] at J=6.5 mA/cm$^2$, however, the current densities applied during the 200 m excitation pulses are significantly higher ($^-$2500 mA/cm$^2$). It is expected that the increased triplet-triplet annihilation and triplet-charge carrier quenching at high injection levels causes the observed reduction in diffusion length.

Previously, the single exciton diffusion coefficient in Alq$_3$ was measured to be D$_s$=(1.2±0.8)×10$^{-5}$ cm$^{2/5}$ (Ref. 22) and D$_s$=2.6×10$^{-4}$ cm$^{2/5}$ (Ref. 23). The diffusion coefficient of triplets is typically lower than that of singlets since both the donor and acceptor transitions are disallowed.

Another embodiment of the present invention includes an organic light emitting layer wherein the energy difference between the lowest triplet excited state of the guest material and a corresponding relaxed state of the guest material has a corresponding wavelength of about 420 nm to 480 nm for blue light emission.

Another embodiment of the present invention includes an organic light emitting layer wherein the energy difference between the lowest triplet excited state of the guest material and a corresponding relaxed state of the guest material has a corresponding wavelength of about 480 nm-510 nm for aqua-blue light emission.

Another embodiment of the present invention includes an organic light emitting layer wherein the host material has a bandgap with an energy difference corresponding to about 470 nm and the guest material has a lowest triplet excited state at an energy level at about 450 nm.

Another embodiment of the present invention includes an organic light emitting layer wherein a plurality of guest materials are dispersed in the host material.

According to the present invention, the peak in the phosphorescent blue emission is preferably produced at a wavelength of $\leq 470$ nm, more preferably at a wavelength of ~450 nm.

Those with skill in the art may recognize various modifications to the embodiments of the invention described and illustrated herein. Such modifications are intended to be covered by the spirit and scope of the present invention. That is, while the invention has been described in detail with reference to certain embodiments, it will be recognized by those skilled in the art that there are other embodiments of the invention within the spirit and scope of the claims.

What is claimed is:

1. A compound having a chemical structure represented by a formula selected from the group consisting of

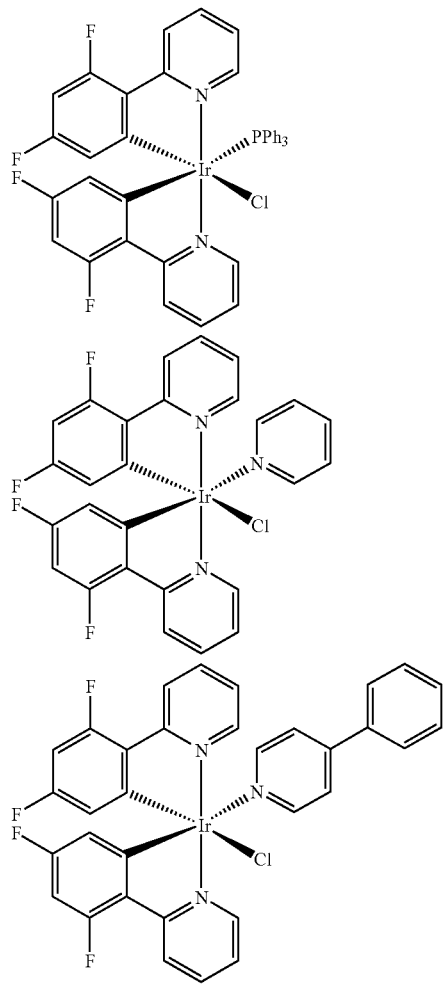

-continued

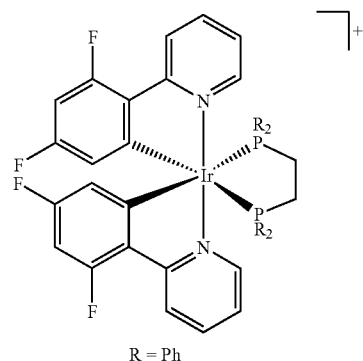

R = Ph

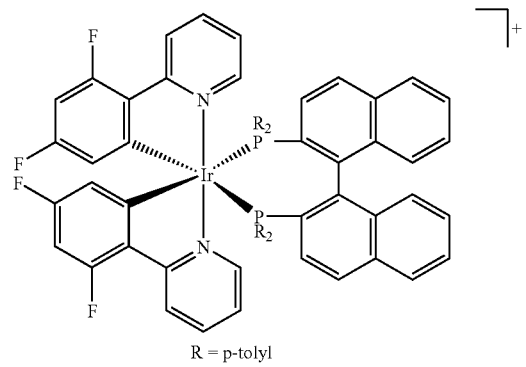

R = p-tolyl

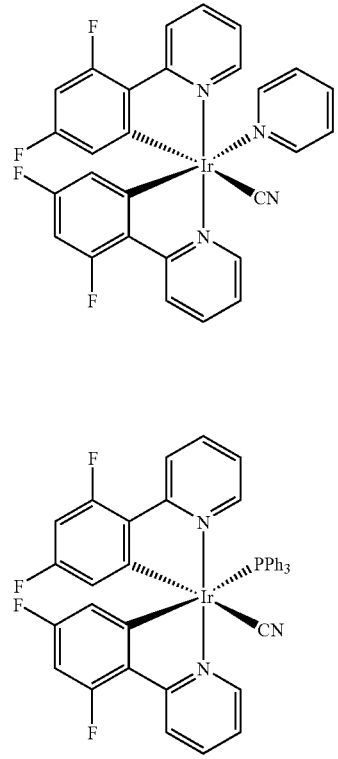

-continued

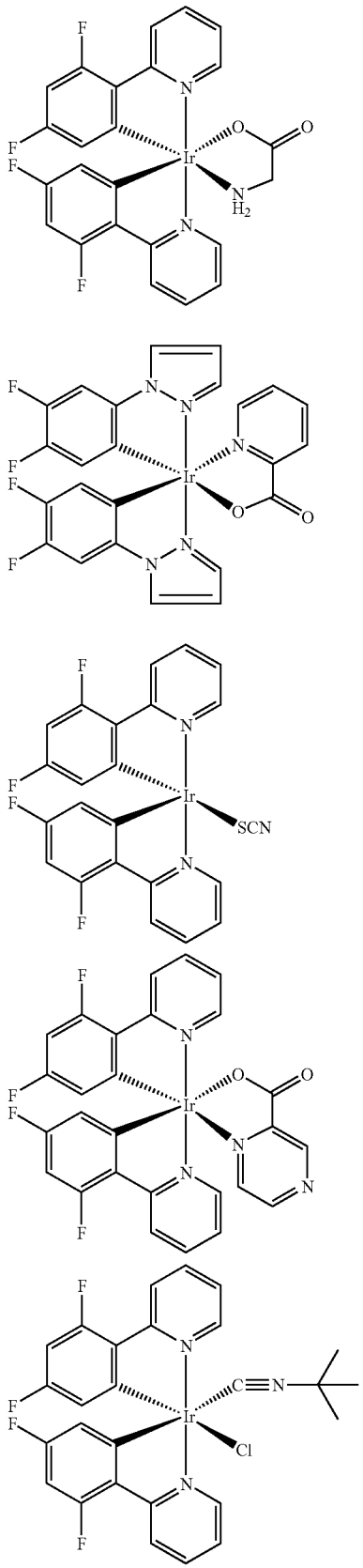

-continued
and

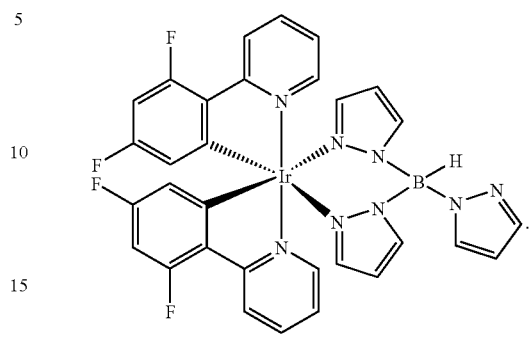

2. An organic light emitting device having an emissive layer comprising an organometallic compound, wherein the organometallic compound consists of
 a metal having an atomic number of at least 72;
 at least one mono-anionic, bidentate, carbon coordination ligand bound to the metal, and
 at least one non mono-anionic, bidentate, carbon coordination ligand bound to the metal,
 wherein the mono-anionic, bidentate, carbon coordination ligand has the structure

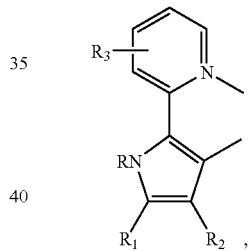

wherein R is halogen, alkyl, or aryl, and $R_1$, $R_2$ and $R_3$ are, independently, hydrogen, halogen, alkyl, or aryl, with the proviso that the at least one mono-anionic, bidentate, carbon-coordination ligand is substituted with at least one of an electron donating substituent and an electron withdrawing substituent.

3. The organic light emitting device of claim 2, wherein R is halogen.

4. The organic light emitting device of claim 2, wherein R is alkyl.

5. The organic light emitting device of claim 2, wherein R is aryl.

6. The organic light emitting device of claim 2, wherein the metal is selected from the group consisting of Os, Ir, Pt and Au.

7. The organic light emitting device of claim 6, wherein the metal is selected from the group consisting of Ir and Pt.

8. The organic light emitting device of claim 2, wherein the non mono-anionic, bidentate, carbon coordination ligand is selected from the group consisting of

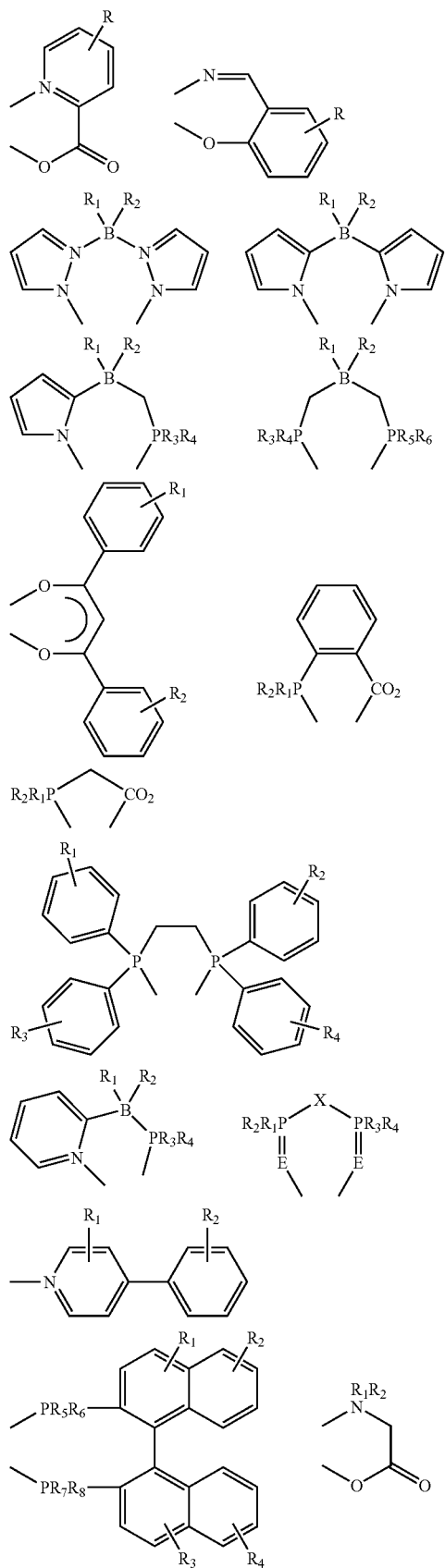

-continued

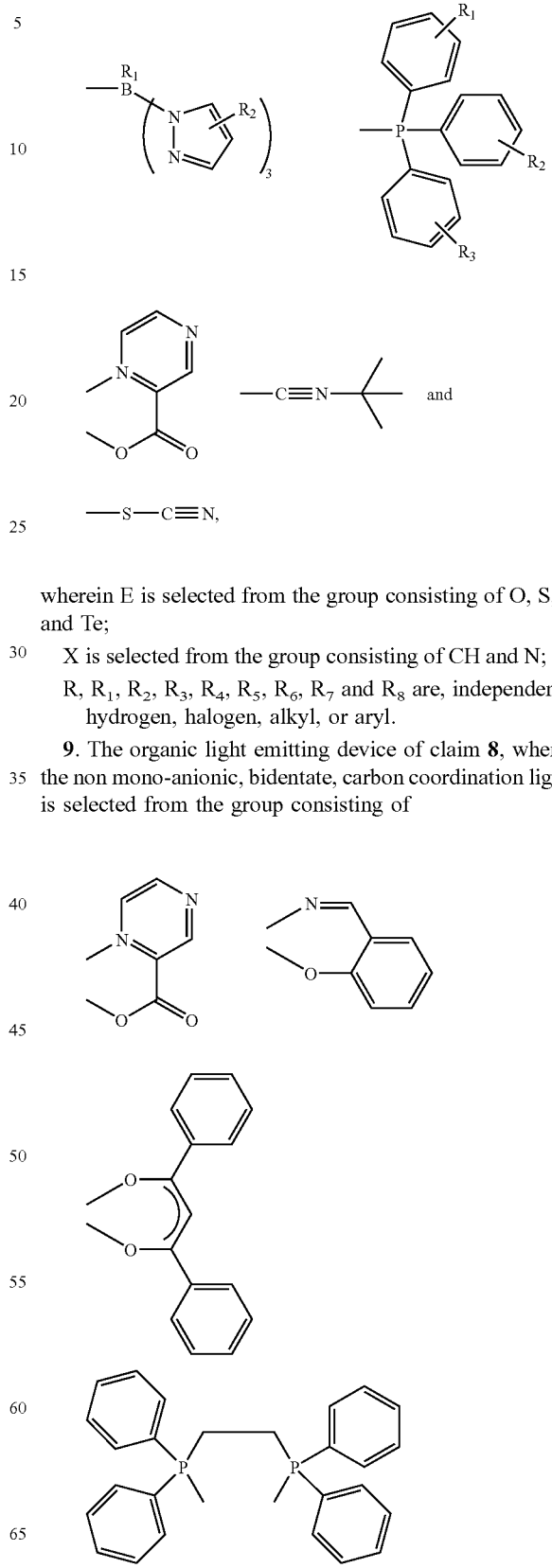

wherein E is selected from the group consisting of O, S, Se and Te;

X is selected from the group consisting of CH and N; and

R, $R_1$, $R_2$, $R_3$, $R_4$, $R_5$, $R_6$, $R_7$ and $R_8$ are, independently, hydrogen, halogen, alkyl, or aryl.

9. The organic light emitting device of claim 8, wherein the non mono-anionic, bidentate, carbon coordination ligand is selected from the group consisting of -continued
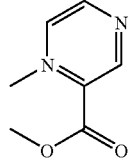 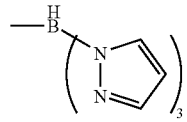
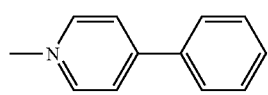
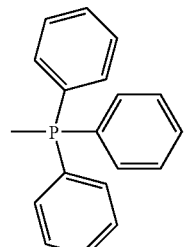 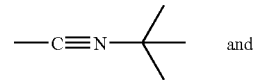 and
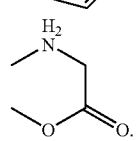
* * * * *